(12) United States Patent
Abelman et al.

(10) Patent No.: US 7,423,045 B2
(45) Date of Patent: Sep. 9, 2008

(54) ABCA1 ELEVATING COMPOUNDS

(75) Inventors: Matthew Abelman, Mountain View, CA (US); Robert Jiang, Milpitas, CA (US); Jeff Zablocki, Mountain View, CA (US); Dmitry Koltun, Foster City, CA (US)

(73) Assignee: CV Therapeutics, Inc., Palo Alto, CA (US)

( * ) Notice: Subject to any disclaimer, the term of this patent is extended or adjusted under 35 U.S.C. 154(b) by 0 days.

(21) Appl. No.: 11/477,745

(22) Filed: Jun. 28, 2006

(65) Prior Publication Data

US 2007/0010544 A1 Jan. 11, 2007

Related U.S. Application Data

(60) Provisional application No. 60/694,741, filed on Jun. 28, 2005.

(51) Int. Cl.
*A61K 31/4741* (2006.01)
*C07D 491/06* (2006.01)

(52) U.S. Cl. .................. 514/285; 546/62; 546/70; 546/22; 544/60; 544/125; 544/361; 514/228.2; 514/232.8; 514/253

(58) Field of Classification Search .................. 514/285, 514/228.2, 232.8, 253; 546/62, 70, 22; 544/60, 544/125, 361

See application file for complete search history.

(56) References Cited

U.S. PATENT DOCUMENTS

| 3,845,770 | A | 11/1974 | Theeuwes et al. |
| 4,326,525 | A | 4/1982 | Swanson et al. |
| 4,902,514 | A | 2/1990 | Barclay et al. |
| 4,992,445 | A | 2/1991 | Lawter et al. |
| 5,001,139 | A | 3/1991 | Lawter et al. |
| 5,023,252 | A | 6/1991 | Hseih |
| 5,616,345 | A | 4/1997 | Geoghegan et al. |
| 6,900,219 | B2 | 5/2005 | Ibrahim et al. |

OTHER PUBLICATIONS

Sabitha, G. et al.: Bismuth(III) chloride-catalyzed intramolecular hetero-diels-alder reactions: a novel synthesis of hexahydrodibenzo[b,h] [1,6]naphthyridines. Tetrahedron Lett. vol. 43, pp. 1573-1575, 2002.*
Zhang D. et al.: "A Solid-phase approach to tetrahydrochromano[4,3-b]quinolines" Synlett, vol. 7, 2001, pp. 1173-1175, XP002406448 Compounds 3-3', scheme 2, p. 1174.
Yadav, J.S et al.: "LPDE-catalyzed Intramolecular Cyclization of Arylimines: a Facile Synthesis of Tetrahydrochromanoquinolines" Synlett, vol. 6, 2002, pp. 993-995, Xp002406449 Coumpounds 2-3, scheme on p. 993.
Anniyappan, M. et al.: "Triphenylphosphonium Percholorate as an Efficient Catalyst for Mono- and Bis-intramolecular Imino Diels-Alder Reactions: Synthesis of Tetrahydrochromanoquinolines" Tetrahedron Letters, vol. 44, No. 18, 2003, pp. 3653-3658, XP002406450, Compounds 3-4 (a-j), scheme 1, p. 3653. Table 1, p. 3654.
Jones, W. et al.: "Intramolecular Cyclization of Aromatic Imines: an Approach to tetrahydrochromano[4,3-b]quinolines" Tetrahedron Letter, vol. 41, No. 14, 2000, pp. 2309-2312, Xp002406451 Compounds 303'(a-f), scheme 2, p. 2311.
Sabitha, G. et al.: "Bismuth (III) Chloride-catalyzed Intramolecular Hetero Diels-Alder Reaction: Application to the Synthesis of tetrahydrochromano[4,3-b]quinoline Derivatives" Synthesis, vol. 13, 2001, pp. 1979-1984, XP002406452, Coumpounds 4-4' (a-h), scheme 1, p. 1979, Table on p. 1980. Compounds 6-6' (a-b), scheme 2, p. 1980.
Sabitha, G. et al.: "Stereoselective Synthesis of Octahydro-3bH-[1,3]dioxolo[4",5":4',5']f intramolecular hetero-Diels-Alder Reactions Catalyzed by Bismuth(III)Chloride", Tetrahedron Letters, vol. 43, No. 22, 2002, pp. 4029-4032, XP002406453, Compounds 3-3', scheme 1, p. 4029 and Table 1, p. 4031.
Wright, G.C. et al.: "A Study of the Catalytic Reductive Products of 2,3-dihydro-6-methoxy-3-(6-nitroveratrylidene)-4H-benzopyran-4-one", Journal of Heterocyclic Chemistry, vol. 13, 1976, pp. 1182-1185, CP002406454, Compounds 2 and 7, scheme 1, p. 1181.
Joseph S.B. and Tontonoz, P. (2003) *Current Opinion in Pharmacology*, 3:192-197.
Brewer H.B. et al. (2004) *Arterioscler. Thromb. Vasc. Biol.*, 24:1755-1760.
Cheung, Marian C et al.; *Arterioscler., Thromb., Vasc. Biol.* (2001), 21(8), 1320-1326.
Remington's Pharmaceutical Sciences, Mace Publishing Co., Philadelphia, PA 17th Ed. (1985) (G.S. Banker & C.T. Rhodes, Eds.)—Book.
"Modern Pharmaceutics", Marcel Dekker, Inc. 3rd Ed. (G.S. Banker & C.T. Rhodes, Eds.).—Book.
Smith et al., *J. Biol. Chem.*, 271:30647-30655 (1996).
Francis et al., *J. Clin. Invest.*, 96, 78-87 (1995).
Kritharides et al Thrombo Vasc Biol 18, 1589-1599,1998.

* cited by examiner

*Primary Examiner*—Charanjit S Aulakh
(74) *Attorney, Agent, or Firm*—Michael J. Beck; J. Elin Hartrum

(57) ABSTRACT

The present invention provides compounds useful for increasing cellular ATP binding cassette transporter ABCA1 production in mammals, and to methods of using such compounds in the treatment of coronary artery diseases, dyslipidemias and metabolic syndrome. The invention also relates to methods for the preparation of such compounds, and to pharmaceutical compositions containing them.

20 Claims, No Drawings

ABCA1 ELEVATING COMPOUNDS

CROSS REFERENCE TO RELATED APPLICATIONS

This application claims priority to U.S. Provisional Patent Application Ser. No. 60/694,741, filed Jun. 28, 2005, the complete disclosure of which is hereby incorporated by reference.

FIELD OF THE INVENTION

The present invention relates to compounds useful for increasing cellular ATP binding cassette transporter ABCA1 production in mammals, and to methods of using such compounds in the treatment of coronary artery diseases, dyslipidiemias and metabolic syndrome. The invention also relates to methods for the preparation of such compounds, and to pharmaceutical compositions containing them.

BACKGROUND OF THE INVENTION

Cholesterol is essential for the growth and viability of higher organisms. It is a lipid that modulates the fluidity of eukaryotic membranes, and is the precursor to steroid hormones such as progesterone, testosterone, and the like. Cholesterol can be obtained from the diet, or synthesized internally in the liver and intestine. Cholesterol is transported in body fluids to tissues by lipoproteins, which are classified according to increasing density. For example, low density lipoprotein cholesterol (LDL) is responsible for transport of cholesterol to and from the liver and to peripheral tissue cells, where LDL receptors bind LDL, and mediate its entry into the cell.

Although cholesterol is essential to many biological processes in mammals, elevated serum levels of LDL cholesterol are undesirable, in that they are known to contribute to the formation of atherosclerotic plaques in arteries throughout the body, which may lead, for example, to the development of dyslipidemia and coronary artery diseases. Conversely, elevated levels of high density lipoprotein cholesterol (HDL-C) have been found, based upon human clinical data and animal model systems, to protect against development of coronary diseases. Low high density lipoprotein (HDL) is also a risk factor and marker for the development of metabolic syndrome and insulin resistance.

In general, excess cholesterol is removed from the body by a pathway involving HDL. Cholesterol is "effluxed" from cells by one of two processes—either by transfer to mature HDL, or an active transfer to apolipoprotein A-1 (Apo A-I). Transfer to mature HDL may involve both active and passive transfer mechanism. Transfer to Apo A-I and the generation of nascent HDL is mediated by ABCA1. In this process, lipid-poor HDL precursors acquire phospholipid and cholesterol forming nascent HDL which can then converted to mature HDL through the action of multiple plasma enzymes and the acquisition of cholesterol from peripheral tissues. HDL cholesterol is eventually transported to the liver where it is either recycled or excreted as bile. This process is often referred to as "reverse cholesterol transport".

One method of treatment aimed at reducing the risk of formation of atherosclerotic plaques in arteries relates to modifying plasma lipid and lipoprotein levels to desirable levels. Such methods includes diet changes, and/or treatment with drugs such as derivatives of fibric acid (clofibrate, gemfibrozil, and fenofibrate), nicotinic acid, and HMG-CoA reductase inhibitors, such as mevinolin, mevastatin, pravastatin, simvastatin, fluvastatin, rosuvastatin, and lovastatin, which reduce plasma LDL cholesterol levels by either inhibiting the intracellular synthesis of cholesterol or inhibiting the uptake via LDL receptors. In addition, bile acid-binding resins, such as cholestyramine, colestipol and probucol decrease the level of LDL-cholesterol by reducing intestinal uptake and increasing the catabolism of LDL-cholesterol in the liver. Nicotinic acid through a poorly defined mechanism increase HDL levels and decreases triacylglycerol levels.

Another method of reducing the risk of formation of atherosclerotic plaques involves increasing the rate of cholesterol efflux from tissues and the formation of nascent HDL by increasing ABCA1 gene expression. The nuclear hormone receptor LXR is a key physiologic modulator of ABCA1 expression, and effectors of the LXR receptor may be used to pharmacologically increase ABCA1 activity. In addition to regulating ABCA1, LXR has been shown to at least partially regulate LXR target genes identified in macrophages, liver, intestine and other sites, which serve to orchestrate a concerted physiological response to excess sterol deposition. These include at least three other members of the ABC transporter family. Two of which have been identified as agents for another rare genetic disorder of sterol metabolism termed sitosterolemia. Another has been implicated as potential transporter of cellular cholesterol to mature and maturing HDL.

Unfortunately, systemic administration of potent full LXR ligands causes increased plasma triglycerides and liver lipid deposition due to the induction of several gene products involved in the synthesis of fats. Lipogenic genes in the liver are highly induced by LXR activation either directly, or via LXR induced transcription of the sterol regulatory protein SREBP1c. Selective LXR activation in macrophages, however, may have a protective role in reverse cholesterol transport while avoiding the pitfalls of inducing lipid bio-synthetic genes in the liver.

Additional advantages may be afforded by selectively interfering with the LXR enhancer/promoter transcription complex with LXR ligands that increase transcription of the subset of LXR target genes involved in cholesterol transport, but not the lipid bio-synthetic target genes. Tissue selective and/or unique partial LXR agonists may also provide the beneficial induction of ABCA1 (and other target genes) in macrophages and other non-hepatic tissues, while causing no or limited induction of SREBP1c and other lipogenic genes in the liver. See, for example Joseph S. B. and Tontonoz, P. (2003) *Current Opinion in Pharmacology*, 3:192-197 and Brewer H. B. et al. (2004) *Arterioscler. Thromb. Vasc. Biol.*, 24:1755-1760.

It is desired to provide alternative therapies aimed at reducing the risk of formation of atherosclerotic plaques in arteries, especially in individuals deficient in the removal of cholesterol from artery walls via the HDL pathway. HDL cholesterol levels are a steady state measurement determined by the relative rates of HDL production and HDL clearance. Multiple enzymes and mechanisms contribute to both production and clearance. One method of increasing HDL levels would be to increase the expression of ABCA1 and the generation of nascent HDL resulting in increased HDL production. Accordingly, it is desired to provide compounds that are stimulators of the expression of ABCA1 in mammals both to increase cholesterol efflux and to raise HDL cholesterol levels in blood. This would be useful for the treatment of various disease states and dyslipidemias characterized by low HDL levels, such as coronary artery disease and metabolic syndrome.

It has also been shown that a combination of a drug that decreases LDL cholesterol levels and a drug that increases HDL cholesterol is beneficial; see, for example, *Arterioscler., Thromb., Vasc. Biol.* (2001), 21(8), 1320-1326, by Marian C. Cheung et al. Accordingly, it is also desired to provide a combination of a compound that stimulates the expression of ABCA1 with a compound that lowers LDL cholesterol levels.

It should be noted it has also been shown that raising production in macrophages locally reduces cholesterol deposition in coronary arteries without significantly raising plasma HDL cholesterol and without effecting cholesterol production by the liver. In this instance, raising ABCA1 expression is beneficial even in the absence of increased HDL cholesterol such that selective non-hepatic upregulation of ABCA1 may have beneficial effects on coronary artery disease in the absence of measurable effects on plasma lipid and lipoprotein levels.

SUMMARY OF THE INVENTION

It is an object of this invention to provide compounds capable of increasing ABCA1 expression. Accordingly, in a first aspect, the invention relates to compounds of Formula I:

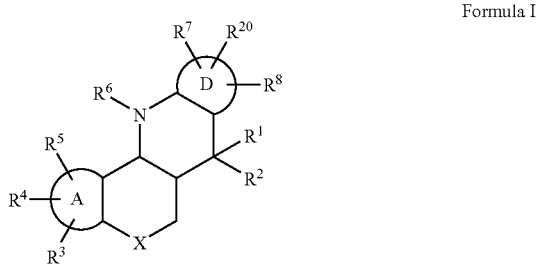

Formula I wherein:

$R^1$ and $R^2$ are independently optionally substituted lower alkyl, optionally substituted aryl, optionally substituted alkenyl, optionally substituted heteroaryl, or optionally substituted heterocyclyl; or $R^1$ and $R^2$ when taken together with the carbon atom to which they are attached represent a 5 or 6 membered carbocyclic or heterocyclic ring;

$R^3$, $R^4$ and $R^5$ are independently hydrogen, hydroxyl, optionally substituted lower alkyl, optionally substituted alkenyl, optionally substituted alkynyl, optionally substituted lower alkoxy, optionally substituted aryl, optionally substituted heteroaryl, optionally substituted heterocyclyl, cyano, halo, —$SO_2$—$NR^9R^{10}$, or —$C(O)R^{11}$, in which $R^9$ and $R^{10}$ are independently hydrogen, optionally substituted lower alkyl, optionally substituted aryl, optionally substituted heteroaryl, optionally substituted heterocyclyl, or may joint to form a 5 or 6 membered optionally substituted heterocyclic ring, and $R^{11}$ is —OH or optionally substituted lower alkoxy;

$R^6$ is hydrogen, optionally substituted lower alkyl, optionally substituted cycloalkyl, —$C(O)R^{12}$, or —$S(O)_2R^{13}$, in which $R^{12}$ is optionally substituted lower alkyl, lower alkoxy or —$NR^{14}R^{15}$, in which $R^{13}$, $R^{14}$, and $R^{15}$ are independently hydrogen, optionally substituted lower alkyl, optionally substituted aryl, optionally substituted heteroaryl, or optionally substituted heterocyclyl, or $R^{14}$ and $R^{15}$ may join to form a 5 or 6 membered optionally substituted heterocyclic ring;

$R^7$ is hydrogen, hydroxyl, optionally substituted lower alkyl, optionally substituted alkenyl, optionally substituted alkynyl, optionally substituted alkoxy, optionally substituted aryl, optionally substituted heteroaryl, optionally substituted heterocyclyl, or —$NR^{14}R^{15}$; and $R^8$ is hydrogen, cyano, optionally substituted lower alkyl, optionally substituted heterocyclyl, optionally substituted phenyl, —$C(O)R^{11}$, —$C(O)R^{14}$, —$SR^{13}$, —$OR^{14}$, —$NR^9S(O)_2R^{10}$, —$NR^{14}C(O)NR^{14}R^{15}$, —$C(O)NR^{14}R^{15}$, —$CH_2C(O)R^{11}$, —$S(O)_2R^{13}$, —$B(OH)_2$, —$C(CF_3)_2OH$, —$CH_2P(O)(R^{11})_2$, halo, —$NHC(O)R^{14}$, —$N[(CH_2)_2]_2SO_2$, or —$S(O)_2NR^9R^{10}$; or $R^7$ and $R^8$ may join together to form an optionally substituted 5 or 6 membered heterocyclic or heteroaryl ring;

$R^{20}$ is hydrogen, cyano, hydroxyl, halo, optionally substituted lower alkyl, optionally substituted alkenyl, optionally substituted alkynyl, optionally substituted alkoxy, optionally substituted aryl, optionally substituted heteroaryl, optionally substituted heterocyclyl, —$NR^{14}R^{15}$, —$C(O)R^{11}$, —$C(O)R^{14}$, —$SR^{14}$, —$OR^{14}$, —$C(S)R^{11}$, —$C(S)R^{14}$, —$NR^9S(O)_2R^{10}$, —$NR^{14}C(O)NR^{14}R^{15}$, —$C(O)NR^{14}R^{15}$, —$C(S)NR^{14}R^{15}$, —$CH_2C(O)R^{11}$, —$S(O)_2R^{13}$, $B(OH)_2$, —$C(CF_3)_2OH$, —$CH_2P(O)(R^{11})_2$, —$NHC(O)CH_3$, —$N[(CH_2)_2]_2SO_2$, or —$S(O)_2 NR^9R^{10}$;

A and D are independently 5 or 6 membered monocyclic heterocyclic, monocyclic heteroaryl, or monocyclic aryl rings; and X is oxygen, sulfur, —S(O)—, —$S(O)_2$— or —$NR^{16}$—, in which $R^{16}$ is hydrogen, optionally substituted lower alkyl, optionally substituted aryl, —$C(O)R^{12}$, or —$S(O)_2R^{13}$.

In a second aspect, the invention relates to a method for using the compounds of Formula I in the treatment of a disease or condition in a mammal that can be treated with a compound that elevates serum levels of HDL-C, comprising administering to a mammal in need thereof a therapeutically effective dose of a compound of Formula I. Such diseases include, but are not limited to, diseases of the artery, in particular coronary artery disease, metabolic syndrome and diabetes.

In a third aspect, the invention relates to a method for using the compounds of Formula I in the treatment of a disease or condition in a mammal that can be treated with a compound that promotes cholesterol efflux from cells, comprising administering to a mammal in need thereof a therapeutically effective dose of a compound of Formula I. Such diseases include, but are not limited to, diseases of the artery, in particular coronary artery disease.

In a fourth aspect, the invention relates to a method for using the compounds of Formula I in the treatment of a disease or condition characterized by low HDL-C in a mammal that can be treated with a compound that elevates serum levels of HDL-C, comprising administering to a mammal in need thereof a therapeutically effective dose of a compound of Formula I. Such diseases include, but are not limited to, diseases of the artery, in particular coronary artery disease, and diabetes.

A fifth aspect of this invention relates to pharmaceutical formulations, comprising a therapeutically effective amount of a compound of Formula I and at least one pharmaceutically acceptable excipient.

A sixth aspect of this invention relates to methods of preparing the compounds of Formula I.

At present, preferred compounds of the invention include, but are not limited to:

2-(2-bromo-7,7-dimethyl(7,12,12a,6a-tetrahydrochromano[4,3-b]quinolin-9-yl))-1,1,1,3,3,3-hexafluoropropan-2-ol;

2-((6aS,12aR)-2-bromo-7,7-dimethyl(7,12,12a,6a-tetrahydrochromano[4,3-b]quinolin-9-yl))-1,1,1,3,3,3-hexafluoropropan-2-ol;

2-((12aS,6aS)-2-bromo-7,7-dimethyl(7,12,12a,6a-tetrahydrochromano[4,3-b]quinolin-9-yl))-1,1,1,3,3,3-hexafluoropropan-2-ol;

2-(2-bromo-7,7-dimethyl-7,12,12a,6a-tetrahydrochromano[4,3-b]quinolin-9-yl)acetic acid;

2-bromo-7,7-dimethyl-7,12,12a,6a-tetrahydrochromano[4,3-b]quinoline-9-carboxamide;

methyl 2-bromo-10-methoxy-7,7-dimethyl-7,12,12a,6a-tetrahydrochromano[4,3-b]quinoline-9-carboxylate;

1,1,1,3,3,3-hexafluoro-2-(2-methoxy-7,7-dimethyl(7,12,12a,6a-tetrahydrochromano[4,3-b]quinolin-9-yl))propan-2-ol;

1,1,1,3,3,3-hexafluoro-2-(4-methoxy-7,7-dimethyl(7,12,12a,6a-tetrahydrochromano[4,3-b]quinolin-9-yl))propan-2-ol;

2-[7,7-dimethyl-2-(trifluoromethoxy)(7,12,12a,6a-tetrahydrochromano[4,3-b]quinolin-9-yl)]-1,1,1,3,3,3-hexafluoropropan-2-ol;

2-[(12aS,6aS)-7,7-dimethyl-2-(trifluoromethoxy)(7,12,12a,6a-tetrahydrochromano[4,3-b]quinolin-9-yl)]-1,1,1,3,3,3-hexafluoropropan-2-ol;

3-methylbut-2-enyl (6aS,12aR)-9-(dihydroxyboramethyl)-7,7-dimethyl-7,12,12a,6a-tetrahydrochromano[4,3-b]quinoline-3-carboxylate;

3-methylbut-2-enyl 9-(dihydroxyboramethyl)-7,7-dimethyl-7,12,12a,6a-tetrahydrochromano[4,3-b]quinoline-3-carboxylate;

3-methylbut-2-enyl 7,7-dimethyl-9-[2,2,2-trifluoro-1-hydroxy-1-(trifluoromethyl)ethyl]-7,12,12a,6a-tetrahydrochromano[4,3-b]quinoline-3-carboxylate;

3-methylbut-2-enyl 7,7-dimethyl-9-[2,2,2-trifluoro-1-hydroxy-1-(trifluoromethyl)ethyl]-7,12,12a,6a-tetrahydrochromano[4,3-b]quinoline-2-carboxylate;

7,7-dimethyl-9-[2,2,2-trifluoro-1-hydroxy-1-(trifluoromethyl)ethyl]-7,12,12a,6a-tetrahydrochromano[4,3-b]quinoline-3-carboxylic acid;

3-methylbut-2-enyl 9-(dihydroxyboramethyl)-7,7-dimethyl-7,12,12a,6a-tetrahydrochromano[4,3-b]quinoline-2-carboxylate;

7,7-dimethyl-9-[2,2,2-trifluoro-1-hydroxy-1-(trifluoromethyl)ethyl]-7,12,12a,6a-tetrahydrochromano[4,3-b]quinoline-2-carboxylic acid;

9-(dihydroxyboramethyl)-7,7-dimethyl-7,12-dihydro-6H-chromeno[4,3-b]quinoline-3-carboxylic acid;

1,1,1,3,3,3-hexafluoro-2-(4,7,7-trimethyl(7,12,12a,6a-tetrahydrochromano[4,3-b]quinolin-9-yl))propan-2-ol;

4-methoxy-7,7-dimethyl-9-(1,2,3,4-tetraazol-5-yl)-7,12,12a,6a-tetrahydrochromano[4,3-b]quinoline;

4-((6aS,12aR)-4-methoxy-7,7-dimethyl-7,12,12a,6a-tetrahydrochromano[4,3-b]quinolin-9-yl)-1,4-thiazaperhydroine-1,1-dione;

4-(4-methoxy-7,7-dimethyl-7,12,12a,6a-tetrahydrochromano[4,3-b]quinolin-9-yl)-1,4-thiazaperhydroine-1,1-dione;

2-(4-ethoxy-7,7-dimethyl(7,12,12a,6a-tetrahydrochromano[4,3-b]quinolin-9-yl))-1,1,1,3,3,3-hexafluoropropan-2-ol;

4-methoxy-7,7-dimethyl-7,12,12a,6a-tetrahydrochromano[4,3-b]quinoline-9-carboxamide;

1,1,1,3,3,3-hexafluoro-2-(1-methoxy-7,7-dimethyl(7,12,12a,6a-tetrahydrochromano[4,3-b]quinolin-9-yl))propan-2-ol;

2-[7,7-dimethyl-4-(3-methylbut-2-enyloxy)(7,12,12a,6a-tetrahydrochromano[4,3-b]quinolin-9-yl)]-1,1,1,3,3,3-hexafluoropropan-2-ol;

2-(4-methoxy-7,7-dimethyl-7,12,12a,6a-tetrahydrochromano[4,3-b]quinolin-9-yl)acetic acid;

3-((6aS,12aR)-4-methoxy-7,7-dimethyl-7,12,12a,6a-tetrahydrochromano[4,3-b]quinolin-9-yl)propanoic acid;

3-((12aR,6aR)-4-methoxy-7,7-dimethyl-7,12,12a,6a-tetrahydrochromano[4,3-b]quinolin-9-yl)propanoic acid;

4,7,7-trimethyl-7,12,12a,6a-tetrahydrochromano[4,3-b]quinoline-9-carboxamide;

4-ethoxy-7,7-dimethyl-7,12,12a,6a-tetrahydrochromano[4,3-b]quinoline-9-carboxamide;

4,7,7-trimethyl-7,12,12a,6a-tetrahydrochromano[4,3-b]quinoline;

(12aS)-4,7,7-trimethyl-7,12,12a,6a-tetrahydrochromano[4,3-b]quinoline;

1,1,1,3,3,3-hexafluoro-2-(4-methoxy-7,7-dimethyl(7,12,12a,6a-tetrahydrochromano[4,3-b]quinolin-9-yl))propan-2-ol;

2-((6aR)-4-methoxy-7,7-dimethyl(7,12,12a,6a-tetrahydrochromano[4,3-b]quinolin-9-yl))-1,1,1,3,3,3-hexafluoropropan-2-ol;

methyl (2E)-3-{7,7-dimethyl-9-[2,2,2-trifluoro-1-hydroxy-1-(trifluoromethyl)ethyl](7,12,12a,6a-tetrahydrochromano[4,3-b]quinolin-2-yl)}prop-2-enoate;

(2E)-3-{7,7-dimethyl-9-[2,2,2-trifluoro-1-hydroxy-1-(trifluoromethyl)ethyl](7,12,12a,6a-tetrahydrochromano[4,3-b]quinolin-2-yl)}—N,N-dimethylprop-2-enamide;

(6aS,12aR)-4-methoxy-7,7-dimethyl-7,12,12a,6a-tetrahydrochromano[4,3-b]quinoline;

(12aS,6aS)-4-methoxy-7,7-dimethyl-7,12,12a,6a-tetrahydrochromano[4,3-b]quinoline;

3-{7,7-dimethyl-9-[2,2,2-trifluoro-1-hydroxy-1-(trifluoromethyl)ethyl](7,12,12a,6a-tetrahydrochromano[4,3-b]quinolin-2-yl)}—N,N-dimethylpropanamide;

methyl 3-{7,7-dimethyl-9-[2,2,2-trifluoro-1-hydroxy-1-(trifluoromethyl)ethyl]-7,12,12a,6a-tetrahydrochromano[4,3-b]quinolin-2-yl}propanoate;

4-ethoxy-7,7-dimethyl-9-(trifluoromethyl)-7,12,12a,6a-tetrahydrochromano[4,3-b]quinoline;

1-(4-ethoxy-7,7-dimethyl-7,12,12a,6a-tetrahydrochromano[4,3-b]quinolin-9-yl)ethan-1-one;

1-(1-methoxy-7,7-dimethyl-7,12,12a,6a-tetrahydrochromano[4,3-b]quinolin-9-yl)ethan-1-one;

1-methoxy-7,7-dimethyl-9-(trifluoromethy;1)-7,12,12a,6a-tetrahydrochromano[4,3-b]quinoline;

1-methoxy-7,7-dimethyl-7,12,12a,6a-tetrahydrochromano[4,3-b]quinoline-9-carboxamide;

(6aS,12aR)-4-methoxy-7,7-dimethyl-9-(methylethyl)-7,12,12a,6a-tetrahydrochromano[4,3-b]quinoline;

(12aS,6aS)-4-methoxy-7,7-dimethyl-9-(methylethyl)-7,12,12a,6a-tetrahydrochromano[4,3-b]quinoline;

(6aS,12aR)-9-fluoro-4-methoxy-7,7-dimethyl-7,12,12a,6a-tetrahydrochromano[4,3-b]quinoline;

(12aS,6aS)-4-methoxy-7,7-dimethyl-7,12,12a,6a-tetrahydrochromano[4,3-b]quinoline-9-carboxylic acid;

4-fluoro-7,7-dimethyl-7,12,12a,6a-tetrahydrochromano[4,3-b]quinoline-9-carboxamide;

1,1,1,3,3,3-hexafluoro-2-(4-fluoro-7,7-dimethyl(7,12,12a,6a-tetrahydrochromano[4,3-b]quinolin-9-yl))propan-2-ol;

((6aS,12aR)-4-methoxy-7,7-dimethyl(7,12,12a,6a-tetrahydrochromano[4,3-b]quinolin-9-yloxy))trifluoromethane;

(12aS,6aR)-1-methoxy-7,7-dimethyl-7,12,12a,6a-tetrahydrochromano[4,3-b]quinoline;

(12aS,6aR)-1-methoxy-7,7-dimethyl-9-(methylethyl)-7,12,12a,6a-tetrahydrochromano[4,3-b]quinoline;
(12aS,6aR)-9-fluoro-1-methoxy-7,7-dimethyl-7,12,12a,6a-tetrahydrochromano[4,3-b]quinoline;
(12aS,6aR)-9-ethoxy-1-methoxy-7,7-dimethyl-7,12,12a,6a-tetrahydrochromano[4,3-b]quinoline;
(12aS,6aR)-1-methoxy-7,7-dimethyl-7,12,12a,6a-tetrahydrochromano[4,3-b]quinoline-9-carboxylic acid;
10-(1H-1,2,3,4-tetraazol-5-yl)(12aS,6aR)-1-methoxy-7,7-dimethyl-7,12,12a,6a-tetrahydrochromano[4,3-b]quinoline;
((12aS,6aR)-1-methoxy-7,7-dimethyl(7,12,12a,6a-tetrahydrochromano[4,3-b]quinolin-9-yloxy))trifluoromethane;
amino(4-methoxy-7,7-dimethyl(7,12,12a,6a-tetrahydrochromano[4,3-b]quinolin-9-yl))methane-1-thione;
{[(4-methoxy-7,7-dimethyl(7,12,12a,6a-tetrahydrochromano[4,3-b]quinolin-9-yl))methyl]sulfonyl}methylamine;
methylethyl 3-(4-methoxy-7,7-dimethyl-7,12,12a,6a-tetrahydrochromano[4,3-b]quinolin-9-yl)benzoate;
methylethyl 3-(4-methoxy-7,7-dimethyl-7,12-dihydro-6H-chromeno[4,3-b]quinolin-9-yl)benzoate;
(12aS,6aR)-1-methoxy-7,7-dimethyl-9-(1,3-oxazol-5-yl)-7,12,12a,6a-tetrahydrochromano[4,3-b]quinoline;
(12aS,6aR)-1-methoxy-7,7-dimethyl-7,12,12a,6a-tetrahydrochromano[4,3-b]quinoline-10-carbonitrile;
2-((6aS,12aR)-1-bromo-4-methoxy-7,7-dimethyl(7,12,12a,6a-tetrahydrochromano[4,3-b]quinolin-9-yl))-1,1,1,3,3,3-hexafluoropropan-2-ol;
2-((6aS,12aR)-2-bromo-4-methoxy-7,7-dimethyl(7,12,12a,6a-tetrahydrochromano[4,3-b]quinolin-9-yl))-1,1,1,3,3,3-hexafluoropropan-2-ol;
2-((12aR,6aR)-2-bromo-4-methoxy-7,7-dimethyl(7,12,12a,6a-tetrahydrochromano[4,3-b]quinolin-9-yl))-1,1,1,3,3,3-hexafluoropropan-2-ol;
2-(2,4-difluoro-7,7-dimethyl(7,12,12a,6a-tetrahydrochromano[4,3-b]quinolin-9-yl))-1,1,1,3,3,3-hexafluoropropan-2-ol;
2-(2,4-dichloro-7,7-dimethyl(7,12,12a,6a-tetrahydrochromano[4,3-b]quinolin-9-yl))-1,1,1,3,3,3-hexafluoropropan-2-ol;
2-(2-chloro-4,7,7-trimethyl(7,12,12a,6a-tetrahydrochromano[4,3-b]quinolin-9-yl))-1,1,1,3,3,3-hexafluoropropan-2-ol;
2-((6aS,12aR)-7,7-dimethyl(7,12,12a,6a-tetrahydrochromano[4,3-b]quinolin-9-yl))-1,1,1,3,3,3-hexafluoropropan-2-ol;
(12aS,6aR)-1-methoxy-7,7-dimethyl-9-(1,2,3,4-tetraazol-5-yl)-7,12,12a,6a-tetrahydrochromano[4,3-b]quinoline;
4-((12aS,6aR)-1-methoxy-7,7-dimethyl-7,12,12a,6a-tetrahydrochromano[4,3-b]quinolin-9-yl)-1,4-thiazaperhydroine-1,1-dione;
(12aS,6aR)-1-methoxy-7,7-dimethyl-9-(1,2,3-thiadiazol-4-yl)-7,12,12a,6a-tetrahydrochromano[4,3-b]quinoline;
1-methoxy-7,7-dimethyl-9-(4-methyl(1,2,4-triazol-3-yl))-7,12,12a,6a-tetrahydrochromano[4,3-b]quinoline;
9-bromo-4-methoxy-7,7-dimethyl-7,12,12a,6a-tetrahydrochromano[4,3-b]quinoline;
4-methoxy-7,7-dimethyl-9-(1,2,3,4-tetraazol-5-ylmethyl)-7,12,12a,6a-tetrahydrochromano[4,3-b]quinoline;
2-((12aS,6aR)-4-methoxy-7,7-dimethyl-2-phenyl(7,12,12a,6a-tetrahydrochromano[4,3-b]quinolin-9-yl))-1,1,1,3,3,3-hexafluoropropan-2-ol;
1-bromo-9-ethoxy-4-methoxy-7,7-dimethyl-7,12,12a,6a-tetrahydrochromano[4,3-b]quinoline;
1-bromo-4-methoxy-7,7-dimethyl-9-(1,3-oxazol-5-yl)-7,12,12a,6a-tetrahydrochromano[4,3-b]quinoline;

1-(1-bromo-4-methoxy-7,7-dimethyl-7,12,12a,6a-tetrahydrochromano[4,3-b]quinolin-9-yl)ethan-1-one;
1-bromo-4-methoxy-7,7-dimethyl-7,12,12a,6a-tetrahydrochromano[4,3-b]quinoline-9-carboxamide;
amino(1-bromo-4-methoxy-7,7-dimethyl(7,12,12a,6a-tetrahydrochromano[4,3-b]quinolin-9-yl))methane-1-thione;
1-bromo-4-methoxy-7,7-dimethyl-9-(methylethoxy)-7,12,12a,6a-tetrahydrochromano[4,3-b]quinoline;
(12aS,6aR)-1-methoxy-7,7-dimethyl-9-(1,2,3,4-tetraazol-5-ylmethyl)-7,12,12a,6a-tetrahydrochromano[4,3-b]quinoline;
(12aS,6aR)-9-bromo-1-methoxy-7,7-dimethyl-7,12,12a,6a-tetrahydrochromano[4,3-b]quinoline;
(12aS,6aR)-9-bromo-4-methoxy-7,7-dimethyl-7,12,12a,6a-tetrahydrochromano[4,3-b]quinoline;
(12aS,6aS)-9-bromo-4-methoxy-7,7-dimethyl-7,12,12a,6a-tetrahydrochromano[4,3-b]quinoline;
9-(tert-butyl)-1-methoxy-7,7-dimethyl-7,12,12a,6a-tetrahydrochromano[4,3-b]quinoline;
{[(1-methoxy-7,7-dimethyl(7,12,12a,6a-tetrahydrochromano[4,3-b]quinolin-9-yl))methyl]sulfonyl}methylamine;
diethoxy[(1-methoxy-7,7-dimethyl(7,12,12a,6a-tetrahydrochromano[4,3-b]quinolin-9-yl))methyl]phosphino-1-one;
[(2-chloro-4-methoxy-7,7-dimethyl(7,12,12a,6a-tetrahydrochromano[4,3-b]quinolin-9-yl))methyl]diethoxyphosphino-1-one;
4-((12aS,6aS)-1-methoxy-7,7-dimethyl-7,12,12a,6a-tetrahydrochromano[4,3-b]quinolin-9-yl)benzenecarbonitrile;
(12aS,6aS)-1-methoxy-7,7-dimethyl-9-[4-(trifluoromethyl)phenyl]-7,12,12a,6a-tetrahydrochromano[4,3-b]quinoline;
(12aS,6aS)-1-methoxy-7,7-dimethyl-9-phenyl-7,12,12a,6a-tetrahydrochromano[4,3-b]quinoline;
(12aS,6aR)-9-ethynyl-1-methoxy-7,7-dimethyl-7,12,12a,6a-tetrahydrochromano[4,3-b]quinoline;
ethyl 4-((12aS,6aS)-1-methoxy-7,7-dimethyl-7,12,12a,6a-tetrahydrochromano[4,3-b]quinolin-9-yl)benzoate;
4-((12aS,6aS)-1-methoxy-7,7-dimethyl-7,12,12a,6a-tetrahydrochromano[4,3-b]quinolin-9-yl)benzenesulfonamide;
[4-((12aS,6aS)-1-methoxy-7,7-dimethyl-7,12,12a,6a-tetrahydrochromano[4,3-b]quinolin-9-yl)phenyl]methan-1-ol;
(12aS,6aR)-9-(4-fluorophenyl)-4-methoxy-7,7-dimethyl-7,12,12a,6a-tetrahydrochromano[4,3-b]quinoline;
1-(2-chloro-4-methoxy-7,7-dimethyl(7,12,12a,6a-tetrahydrochromano[4,3-b]quinolin-9-yl))-2-methoxybenzene;
1-(4-fluoro-7,7-dimethyl-7,12,12a,6a-tetrahydrochromano[4,3-b]quinolin-9-yl)ethan-1-one;
4-fluoro-7,7-dimethyl-9-(methylethoxy)-7,12,12a,6a-tetrahydrochromano[4,3-b]quinoline;
(12aS)-4-fluoro-7,7-dimethyl-9-(methylethoxy)-7,12,12a,6a-tetrahydrochromano[4,3-b]quinoline;
4-fluoro-9-(2-methoxyphenyl)-7,7-dimethyl-7,12-dihydro-6H-chromeno[4,3-b]quinolin-12-ol;
(2-chloro-4-methoxy-7,7-dimethyl(7,12,12a,6a-tetrahydrochromano[4,3-b]quinolin-9-yl))[(4-methylphenyl)sulfonyl]amine;
4-((12aS,6aR)-1-methoxy-7,7-dimethyl-7,12,12a,6a-tetrahydrochromano[4,3-b]quinolin-9-yl)benzoic acid;
ethyl 4-((12aS,6aR)-1-methoxy-7,7-dimethyl-7,12,12a,6a-tetrahydrochromano[4,3-b]quinolin-9-yl)benzoate;
4-((12aS,6aR)-1-methoxy-7,7-dimethyl-7,12,12a,6a-tetrahydrochromano[4,3-b]quinolin-9-yl)benzamide;
(12aS,6aR)-9-(4-fluorophenyl)-1-methoxy-7,7-dimethyl-7,12,12a,6a-tetrahydrochromano[4,3-b]quinoline;

(12aS,6aR)-1-methoxy-7,7-dimethyl-9-(2-methyl(1,3-thiazol-4-yl))-7,12,12a,6a-tetrahydrochromano[4,3-b]quinoline;

(12aS,6aR)-1-methoxy-7,7-dimethyl-9-pyrazol-3-yl-7,12,12a,6a-tetrahydrochromano[4,3-b]quinoline;

ethyl 2-((12aS,6aR)-1-methoxy-7,7-dimethyl-7,12,12a,6a-tetrahydrochromano[4,3-b]quinolin-9-yl)-1,3-oxazole-4-carboxylate;

((12aS,6aR)-1-methoxy-7,7-dimethyl(7,12,12a,6a-tetrahydrochromano[4,3-b]quinolin-9-yl))-4-methoxybenzene;

methyl 3-((12aS,6aR)-1-methoxy-7,7-dimethyl-7,12,12a,6a-tetrahydrochromano[4,3-b]quinolin-9-yl)benzoate;

3-[4-((12aS,6aR)-1-methoxy-7,7-dimethyl-7,12,12a,6a-tetrahydrochromano[4,3-b]quinolin-9-yl)phenyl]propanoic acid;

(2E)-3-[4-((12aS,6aR)-1-methoxy-7,7-dimethyl(7,12,12a,6a-tetrahydrochromano[4,3-b]quinolin-9-yl))phenyl]prop-2-enoic acid;

(6aS,12aR)-7-methoxy-13,13-dimethyl-6,13,12a,6a-tetrahydrobenzothiazolo[6,7-b]chromano[3,4-e]pyridine;

(6aS,12aR)-7-methoxy-13,13-dimethyl-6,13,12a,6a-tetrahydro-1H-chromano[3,4-e]indazolo[6,7-b]pyridine;

(6aS,12aR)-7-methoxy-2,13,13-trimethyl-6,13,12a,6a-tetrahydrobenzothiazolo[5,4-b]chromano[3,4-e]pyridine;

(12bS,6aR)-12-methoxy-6,6-dimethyl-6,13,12b,6a-tetrahydrochromano[4,3-b]1,2,5-thiadiazolo[3,4-h]quinoline;

ethyl 1-((6aR,12aS)-6a,7,12,12a-tetrahydro-1-methoxy-7,7-dimethyl-6H-chromeno[4,3-b]quinolin-9-yl)-5-methyl-1H-pyrazole-4-carboxylate;

(6aR,12aS)-6a,7,12,12a-tetrahydro-N-(2-hydroxyethyl)-1-methoxy-7,7-dimethyl-6H-chromeno[4,3-b]quinoline-9-carboxamide;

1-((6aR,12aS)-6a,7,12,12a-tetrahydro-1-methoxy-7,7-dimethyl-6H-chromeno[4,3-b]quinolin-9-yl)-5-methyl-1H-pyrazole-4-carboxylic acid;

((6aR,12aS)-6a,7,12,12a-tetrahydro-4-methoxy-7,7-dimethyl-6H-chromeno[4,3-b]quinolin-9-yl)(morpholino)methanone;

((6aS,12aS)-6a,7,12,12a-tetrahydro-4-methoxy-7,7-dimethyl-6H-chromeno[4,3-b]quinolin-9-yl)(morpholino)methanone;

((6aR,12aS)-6a,7,12,12a-tetrahydro-1-methoxy-7,7-dimethyl-6H-chromeno[4,3-b]quinolin-9-yl)(1,1-dione-1,4-thiazaperhydroin-yl)methanone;

(6aR,12aS)-6a,7,12,12a-tetrahydro-1-methoxy-7,7-dimethyl-9-(methylsulfonyl)-6H-chromeno[4,3-b]quinoline; and (6aR,12aS)-9-(4-fluorophenylsulfonyl)-6a,7,12,12a-tetrahydro-1-methoxy-7,7-dimethyl-6H-chromeno[4,3-b]quinoline.

(6aR,12aS)-6a,7,12,12a-tetrahydro-1-methoxy-N,N,7,7-tetramethyl-6H-chromeno[4,3-b]quinoline-9-carboxamide;

2-((6aR,12aS)-6a,7,12,12a-tetrahydro-1-methoxy-7,7-dimethyl-6H-chromeno[4,3-b]quinolin-9-ylsulfonyl)acetic acid;

((6aR,12aS)-6a,7,12,12a-tetrahydro-1-methoxy-7,7-dimethyl-6H-chromeno[4,3-b]quinolin-9-yl)(4-tert-butyl-carboxylate-piperazin-1-yl)methanone;

((6aR,12aS)-6a,7,12,12a-tetrahydro-1-fluoro-7,7-dimethyl-6H-chromeno[4,3-b]quinolin-9-yl)(4-tert-butyl-carboxylate-piperazin-1-yl)methanone;

((6aR,12aS)-6a,7,12,12a-tetrahydro-1-methoxy-7,7-dimethyl-6H-chromeno[4,3-b]quinolin-9-yl)(piperazin-1-yl)methanone;

((6aS,12aS)-6a,7,12,12a-tetrahydro-4-methoxy-7,7-dimethyl-6H-chromeno[4,3-b]quinolin-9-yl)(1,1-dione-1,4-thiazaperhydroin-yl)methanone;

((6aR,12aS)-6a,7,12,12a-tetrahydro-4-methoxy-7,7-dimethyl-6H-chromeno[4,3-b]quinolin-9-yl)(1,1-dione-1,4-thiazaperhydroin-yl)methanone;

((6aR,12aS)-1-fluoro-6a,7,12,12a-tetrahydro-7,7-dimethyl-6H-chromeno[4,3-b]quinolin-9-yl)(piperazin-1-yl)methanone;

2-((6aR,12aS)-1-fluoro-6a,7,12,12a-tetrahydro-7,7-dimethyl-6H-chromeno[4,3-b]quinolin-9-yl)oxazole-4-carboxylic acid;

((6aR,12aS)-1-methoxy-6a,7,12,12a-tetrahydro-7,7-dimethyl-6H-chromeno[4,3-b]quinolin-9-yl)(4-ethanesulfonylpiperazin-1-yl)methanone;

((6aS,12aS)-4-methoxy-6a,7,12,12a-tetrahydro-7,7-dimethyl-6H-chromeno[4,3-b]quinolin-9-yl)(4-ethanesulfonylpiperazin-1-yl)methanone;

((6aR,12aS)-4-methoxy-6a,7,12,12a-tetrahydro-7,7-dimethyl-6H-chromeno[4,3-b]quinolin-9-yl)(4-ethanesulfonylpiperazin-1-yl)methanone;

ethyl 1-((6aR,12aS)-6a,7,12,12a-tetrahydro-1-methoxy-7,7-dimethyl-6H-chromeno[4,3-b]quinolin-9-yl)-1H-pyrazole-4-carboxylate;

1-((6aR,12aS)-6a,7,12,12a-tetrahydro-1-methoxy-7,7-dimethyl-6H-chromeno[4,3-b]quinolin-9-yl)-1H-pyrazole-4-carboxylic acid;

1-((6aR,12aS)-6a,7,12,12a-tetrahydro-1-methoxy-7,7-dimethyl-6H-chromeno[4,3-b]quinolin-9-yl)—N,N-dimethyl-1H-pyrazole-4-carboxamide;

1-((6aR,12aS)-6a,7,12,12a-tetrahydro-1-methoxy-7,7-dimethyl-6H-chromeno[4,3-b]quinolin-9-yl)-1H-pyrazole-4-((1,1-dione-1,4-thiazaperhydroin-yl)methanone);

((6aS,12aS)-4-fluoro-6a,7,12,12a-tetrahydro-7,7-dimethyl-6H-chromeno[4,3-b]quinolin-9-yl)(4-ethanesulfonylpiperazin-1-yl)methanone;

1-((6aR,12aS)-6a,7,12,12a-tetrahydro-1-methoxy-7,7-dimethyl-6H-chromeno[4,3-b]quinolin-9-yl)-5-methyl-1H-pyrazole-4-((4-ethanesulfonylpiperazin-1-yl)methanone);

1-((6aR,12aS)-6a,7,12,12a-tetrahydro-1-methoxy-7,7-dimethyl-6H-chromeno[4,3-b]quinolin-9-yl)1-5-methyl-1H-pyrazole-4-((1,1-dione-1,4-thiazaperhydroin-yl)methanone);

2-((6aR,12aS)-1-fluoro-6a,7,12,12a-tetrahydro-7,7-dimethyl-6H-chromeno[4,3-b]quinolin-9-yl)oxazole-(4-(4-ethanesulfonylpiperazin-1-yl)methanone);

2-((6aR,12aS)-1-fluoro-6a,7,12,12a-tetrahydro-7,7-dimethyl-6H-chromeno[4,3-b]quinolin-9-yl)oxazole-(4-(1,1-dione-1,4-thiazaperhydroin-yl)methanone);

1-((6aR,12aS)-6a,7,12,12a-tetrahydro-1-fluoro-7,7-dimethyl-6H-chromeno[4,3-b]quinolin-9-yl)-5-methyl-1H-pyrazole-4-((4-ethanesulfonylpiperazin-1-yl)methanone);

1-((6aR,12aS)-6a,7,12,12a-tetrahydro-1-fluoro-7,7-dimethyl-6H-chromeno[4,3-b]quinolin-9-yl)1-5-methyl-1H-pyrazole-4-((1,1-dione-1,4-thiazaperhydroin-yl)methanone);

2-((6aR,12aS)-6a,7,12,12a-tetrahydro-4-methoxy-7,7-dimethyl-6H-chromeno[4,3-b]quinolin-9-yl)oxazole-4-carboxylic acid;

2-((6aR,12aS)-1-methoxy-6a,7,12,12a-tetrahydro-7,7-dimethyl-6H-chromeno[4,3-b]quinolin-9-yl)oxazole-(4-(4-ethanesulfonylpiperazin-1-yl)methanone);

2-((6aR,12aS)-1-methoxy-6a,7,12,12a-tetrahydro-7,7-dimethyl-6H-chromeno[4,3-b]quinolin-9-yl)oxazole-(4-(1,1-dione-1,4-thiazaperhydroin-yl)methanone);

(6aR,12aS)-2-bromo-6a,7,12,12a-tetrahydro-4-methoxy-7,7-dimethyl-9-(oxazol-5-yl)-6H-chromeno[4,3-b]quinoline;

(6aS,12aS)-2-bromo-6a,7,12,12a-tetrahydro-4-methoxy-7,7-dimethyl-9-(oxazol-5-yl)-6H-chromeno[4,3-b]quinoline;

(6aR,12aS)-methyl 2-bromo-6a,7,12,12a-tetrahydro-4-methoxy-7,7-dimethyl-6H-chromeno[4,3-b]quinoline-9-carboxylate;

(6aS,12aS)-methyl 2-bromo-6a,7,12,12a-tetrahydro-4-methoxy-7,7-dimethyl-6H-chromeno[4,3-b]quinoline-9-carboxylate;

(6aR,12aS)-methyl 6a,7,12,12a-tetrahydro-1-methoxy-7,7,12-trimethyl-6H-chromeno[4,3-b]quinoline-9-carboxylate;

2-((6aR,12aS)-6a,7-dihydro-1-methoxy-7,7-dimethyl-6H-chromeno[4,3-b]quinolin-12(12aH)-yl)acetic acid;

(6aR,12aS)-6a,7,12,12a-tetrahydro-12-isopropyl-1-methoxy-7,7-dimethyl-6H-chromeno[4,3-b]quinoline;

2-((6aS,12aS)-6a,7-dihydro-1-methoxy-7,7-dimethyl-6H-chromeno[4,3-b]quinolin-12(12aH)-yl)acetic acid;

ethyl 2-((6aS,12aS)-6a,7-dihydro-1-methoxy-7,7-dimethyl-6H-chromeno[4,3-b]quinolin-12(12aH)-yl)acetate;

ethyl 2-((6aR,12aS)-6a,7-dihydro-1-methoxy-7,7-dimethyl-6H-chromeno[4,3-b]quinolin-12(12aH)-yl)acetate;

(6aR,12aS)-12-benzyl-6a,7,12,12a-tetrahydro-1,9-dimethoxy-7,7-dimethyl-6H-chromeno[4,3-b]quinoline;

(6aR,12aS)-6a,7,12,12a-tetrahydro-4-methoxy-7,7-dimethyl-9-(oxazol-5-yl)-2-(1H-pyrazol-4-yl)-6H-chromeno[4,3-b]quinoline;

(6aS,12aS)-6a,7,12,12a-tetrahydro-4-methoxy-7,7-dimethyl-9-(oxazol-5-yl)-2-(1H-pyrazol-4-yl)-6H-chromeno[4,3-b]quinoline;

(6aR,12aS)-methyl 6a,7,12,12a-tetrahydro-4-methoxy-7,7-dimethyl-2-(1H-pyrazol-4-yl)-6H-chromeno[4,3-b]quinoline-9-carboxylate;

(6aR,12aS)-methyl 6a,7,12,12a-tetrahydro-4-methoxy-7,7-dimethyl-2-(3,5-dimethylisoxazol-4-yl)-6H-chromeno[4,3-b]quinoline-9-carboxylate;

(6aS,12aS)-12-ethyl-6a,7,12,12a-tetrahydro-1-methoxy-7,7-dimethyl-6H-chromeno[4,3-b]quinoline;

(6aR,12aS)-2-bromo-6a,7,12,12a-tetrahydro-4-methoxy-7,7-dimethyl-9-(1H-tetrazol-5-yl)-6H-chromeno[4,3-b]quinoline;

(6aR,12aS)-6a,7,12,12a-tetrahydro-4-methoxy-7,7-dimethyl-2-(3,5-dimethylisoxazol-4-yl)-9-(oxazol-5-yl)-6H-chromeno[4,3-b]quinoline.

(6aR,12aS)-12-cyclohexyl-6a,7,12,12a-tetrahydro-1-methoxy-7,7-dimethyl-6H-chromeno[4,3-b]quinoline;

(6aS,12aS)-12-cyclohexyl-6a,7,12,12a-tetrahydro-1-methoxy-7,7-dimethyl-6H-chromeno[4,3-b]quinoline.

diethyl ((6aR, 12aS)-2-bromo-6a,7,12,12a-tetrahydro-4-methoxy-7,7-dimethyl-6H-chromeno[4,3-b]quinolin-9-yl)methylphosphonate;

(6aS,12aS)-2-bromo-6a,7,12,12a-tetrahydro-4-methoxy-7,7-dimethyl-9-(1H-tetrazol-5-yl)-6H-chromeno[4,3-b]quinoline;

methyl 3-((6aS,12aR)-6a,7-dihydro-1-methoxy-7,7-dimethyl-6H-chromeno[4,3-b]quinolin-12(12aH)-yl)propanoate;

methyl 3-((6aR,12aR)-6a,7-dihydro-1-methoxy-7,7-dimethyl-6H-chromeno[4,3-b]quinolin-1 2(12aH)-yl)propanoate;

(6aR,12aS)-12-propyl-6a,7,12,12a-tetrahydro-1-methoxy-7,7-dimethyl-6H-chromeno[4,3-b]quinoline;

(6aS,12aS)-12-propyl-6a,7,12,12a-tetrahydro-1-methoxy-7,7-dimethyl-6H-chromeno[4,3-b]quinoline;

(6aR,12aS)-12-butyl-6a,7,12,12a-tetrahydro-1-methoxy-7,7-dimethyl-6H-chromeno[4,3-b]quinoline;

(6aS,12aS)-12-butyl-6a,7,12,12a-tetrahydro-1-methoxy-7,7-dimethyl-6H-chromeno[4,3-b]quinoline;

(6aS,12aS)-6a,7,12,12a-tetrahydro-1,9-dimethoxy-7,7,12-trimethyl-6H-chromeno[4,3-b]quinoline; and 1-((6aS,12aS)-6a,7,12,12a-tetrahydro-2-iodo-4-methoxy-7,7-dimethyl-6H-chromeno[4,3-b]quinolin-9-yl)-5-methyl-1H-pyrazole-4-carboxylic acid;

1-((6aR,12aS)-6a,7,12,12a-tetrahydro-2-iodo-4-methoxy-7,7-dimethyl-6H-chromeno[4,3-b]quinolin-9-yl)-5-methyl-1H-pyrazole-4-carboxylic acid;

diethyl ((6aS,12aS)-2-bromo-6a,7,12,12a-tetrahydro-4-methoxy-7,7-dimethyl-6H-chromeno[4,3-b]quinolin-9-yl)methylphosphonate;

diethyl (6a,7,12,12a-tetrahydro-1-methoxy-7,7-dimethyl-6H-chromeno[4,3-b]quinolin-9-yl)methylphosphonate;

diethyl ((6aR,12aS)-6a,7,12,12a-tetrahydro-4-methoxy-7,7-dimethyl-2-(1H-pyrazol-4-yl)-6H-chromeno[4,3-b]quinolin-9-yl)methylphosphonate; and (6aR,12aS)-6a,7,12,12a-tetrahydro-4-methoxy-7,7-dimethyl-2-(1H-pyrazol-4-yl)-6H-chromeno[4,3-b]quinoline-9-carbonitrile.

DEFINITIONS AND GENERAL PARAMETERS

The term "alkyl" refers to a monoradical branched or unbranched saturated hydrocarbon chain having from 1 to 20 carbon atoms. This term is exemplified by groups such as methyl, ethyl, n-propyl, iso-propyl, n-butyl, iso-butyl, t-butyl, n-hexyl, n-decyl, tetradecyl, and the like.

The term "substituted alkyl" refers to:

1) an alkyl group as defined above, having from 1 to 7 substituents, for example 1 to 3 substituents, selected from the group consisting of alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, phosphate, thiocarbonyl, aminosulfinyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, phosphate, quaternary amino, nitro, —SO$_3$H, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, quaternary amino, cyano, —SO$_3$H, and —S(O)$_n$R, where R is alkyl, aryl, or heteroaryl and n is 0, 1 or 1; or 2) an alkyl group as defined above that is interrupted by 1-5 atoms or groups independently chosen from oxygen, sulfur and —N(R$_a$)$_v$—, where v is 1 or 2 and R$_a$ is chosen from hydrogen, alkyl, cycloalkyl, alkenyl, cycloalkenyl, alkynyl, aryl, heteroaryl and heterocyclyl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, quaternary amino, cyano, —SO$_3$H, and —S(O)$_n$R, where R is alkyl, aryl, or heteroaryl and n is 0, 1 or 2; or 3) an alkyl group as defined above that has both from 1 to 5 substituents as defined above and is also interrupted by 1-5 atoms or groups as defined above.

The term "lower alkyl" refers to a monoradical branched or unbranched saturated hydrocarbon chain having from 1 to 6 carbon atoms. Groups such as methyl, ethyl, n-propyl, isopropyl, n-butyl, iso-butyl, t-butyl, n-hexyl, and the like exemplify this term.

The term "substituted lower alkyl" refers to lower alkyl as defined above having 1 to 7 substituents, for example 1 to 3 substituents, as defined for substituted alkyl, or a lower alkyl group as defined above that is interrupted by 1-5 atoms as defined for substituted alkyl, or a lower alkyl group as defined above that has both from 1 to 5 substituents as defined above and is also interrupted by 1-5 atoms as defined above.

The term "alkylene" refers to a diradical of a branched or unbranched saturated hydrocarbon chain, for example having from 1 to 20 carbon atoms, for example 1-10 carbon atoms, more for example 1-6 carbon atoms. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

The term "lower alkylene" refers to a diradical of a branched or unbranched saturated hydrocarbon chain, for example having from 1 to 6 carbon atoms.

The term "substituted alkylene" refers to:
(1) an alkylene group as defined above having from 1 to 5 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, phosphate, thiocarbonyl, aminosulfinyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, quaternary amino, nitro, —SO$_3$H, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, quaternary amino, cyano, —SO$_3$H, and —S(O)$_n$R, where R is alkyl, aryl, or heteroaryl and n is 0, 1 or 2; or
(2) an alkylene group as defined above that is interrupted by 1-5 atoms or groups independently chosen from oxygen, sulfur and —N(R$_a$)$_v$—, where v is 1 or 2 and R$_a$ is chosen from hydrogen, alkyl, cycloalkyl, alkenyl, cycloalkenyl, alkynyl, aryl, heteroaryl, heterocyclyl carbonyl, carboxyester, carboxyamide and sulfonyl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, quaternary amino, cyano, —SO$_3$H, and —S(O)$_n$R, where R is alkyl, aryl, or heteroaryl and n is 0, 1 or 2; or
(3) an alkylene group as defined above that has both from 1 to 5 substituents as defined above and is also interrupted by 1-20 atoms as defined above. Examples of substituted alkylenes are chloromethylene (—CH(Cl)—), aminoethylene (—CH(NH$_2$)CH$_2$—), methylaminoethylene (—CH(NH$_2$)CH$_2$—), 2-carboxypropylene isomers(—CH$_2$CH(CO$_2$H)CH$_2$—), ethoxyethyl (—CH$_2$CH$_2$O—CH$_2$CH$_2$—), ethylmethylaminoethyl (—CH$_2$CH$_2$N(CH$_3$)CH$_2$CH$_2$—), 1-ethoxy-2-(2-ethoxy-ethoxy)ethane (—CH$_2$CH$_2$O—CH$_2$CH$_2$—OCH$_2$CH$_2$—OCH$_2$CH$_2$—), and the like.

The term "aralkyl" refers to an aryl group covalently linked to an alkylene group, where aryl and alkylene are defined herein. "Optionally substituted aralkyl" refers to an optionally substituted aryl group covalently linked to an optionally substituted alkylene group. Such aralkyl groups are exemplified by benzyl, phenylethyl, 3-(4-methoxyphenyl)propyl, and the like.

The term "alkoxy" refers to the group R—O—, where R is optionally substituted alkyl or optionally substituted cycloalkyl, or R is a group —Y-Z, in which Y is optionally substituted alkylene and Z is optionally substituted alkenyl, optionally substituted alkynyl; or optionally substituted cycloalkenyl, where alkyl, alkenyl, alkynyl, cycloalkyl and cycloalkenyl are as defined herein. Preferred alkoxy groups are optionally substituted alkyl-O— and include, by way of example, methoxy, ethoxy, n-propoxy, isopropoxy, n-butoxy, tert-butoxy, sec-butoxy, n-pentoxy, n-hexoxy, 1,2-dimethylbutoxy, trifluoromethoxy, and the like.

The term "alkylthio" refers to the group R—S—, where R is as defined for alkoxy.

The term "alkenyl" refers to a monoradical of a branched or unbranched unsaturated hydrocarbon group for example having from 2 to 20 carbon atoms, more for example 2 to 10 carbon atoms and even more for example 2 to 6 carbon atoms and having 1-6, for example 1, double bond (vinyl). Preferred alkenyl groups include ethenyl or vinyl (—CH=CH$_2$), 1-propylene or allyl (—CH$_2$CH=CH$_2$), isopropylene, (—C(CH$_3$)=CH$_2$), bicyclo[2.2.1]heptene, and the like. In the event that alkenyl is attached to nitrogen, the double bond cannot be alpha to the nitrogen.

The term "lower alkenyl" refers to alkenyl as defined above having from 2 to 6 carbon atoms.

The term "substituted alkenyl" refers to an alkenyl group as defined above having from 1 to 5 substituents, and for example 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, quaternary amino, cyano, halogen, hydroxy, keto, phosphate, thiocarbonyl, aminosulfinyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO$_3$H, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, quaternary amino, —SO$_3$H, and —S(O)$_n$R, where R is alkyl, aryl, or heteroaryl and n is 0, 1 or 2.

The term "alkynyl" refers to a monoradical of an unsaturated hydrocarbon, for example having from 2 to 20 carbon atoms, more for example 2 to 10 carbon atoms and even more for example 2 to 6 carbon atoms and having at least 1 and for example from 1-6 sites of acetylene (triple bond) unsaturation. Preferred alkynyl groups include ethynyl, (—C≡CH), propargyl (or prop-1-yn-3-yl, —CH$_2$C≡CH), and the like. In the event that alkynyl is attached to nitrogen, the triple bond cannot be alpha to the nitrogen.

The term "substituted alkynyl" refers to an alkynyl group as defined above having from 1 to 5 substituents, and for example 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, quaternary amino, halogen, hydroxy, keto, phosphate, thiocarbonyl, aminosulfinyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO₃H, —SO-alkyl, —SO-aryl, —SO-heteroaryl, —SO₂-alkyl, SO₂-aryl and —SO₂-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, $CF_3$, amino, substituted amino, cyano, quaternary amino, —SO₃H, and —S(O)$_n$R, where R is alkyl, aryl, or heteroaryl and n is 0, 1 or 2.

The term "aminocarbonyl" refers to the group —C(O)NRR where each R is independently hydrogen, alkyl, aryl, heteroaryl, heterocyclyl or where both R groups are joined to form a heterocyclic or heteroaryl group (e.g., morpholino). Unless otherwise constrained by the definition, all substituents may optionally be further substituted by 1-3 substituents chosen from alkyl, carboxy, carboxyalkyl, aminocarbonyl, hydroxy, alkoxy, halogen, $CF_3$, amino, substituted amino, cyano, quaternary amino, —SO₃H, and —S(O)$_n$R, where R is alkyl, aryl, or heteroaryl and n is 0, 1 or 2.

The term "aminothiocarbonyl" or "aminosulfinyl" refers to the group —C(S)NRR where each R is independently hydrogen, alkyl, aryl, heteroaryl, heterocyclyl or where both R groups are joined to form a heterocyclic group (e.g., morpholino). Unless otherwise constrained by the definition, all substituents may optionally be further substituted by 1-3 substituents chosen from alkyl, carboxy, carboxyalkyl, aminocarbonyl, hydroxy, alkoxy, halogen, $CF_3$, amino, substituted amino, cyano, quaternary amino, —SO₃H, and —S(O)$_n$R, where R is alkyl, aryl, or heteroaryl and n is 0, 1 or 2.

The term "aaminosulfonyl" refers to the group —S(O)₂NRR where each R is independently hydrogen, alkyl, aryl, heteroaryl, heterocyclyl or where both R groups are joined to form a heterocyclic group (e.g., morpholino). Unless otherwise constrained by the definition, all substituents may optionally be further substituted by 1-3 substituents chosen from alkyl, carboxy, carboxyalkyl, aminocarbonyl, hydroxy, alkoxy, halogen, $CF_3$, amino, substituted amino, cyano, quaternary amino, —SO₃H, and —S(O)$_n$R, where R is alkyl, aryl, or heteroaryl and n is 0, 1 or 2.

The term "acylamino" refers to the group —NRC(O)R where each R is independently hydrogen, alkyl, aryl, heteroaryl, or heterocyclyl. Unless otherwise constrained by the definition, all substituents may optionally be further substituted by 1-3 substituents chosen from alkyl, carboxy, carboxyalkyl, aminocarbonyl, hydroxy, alkoxy, halogen, $CF_3$, amino, substituted amino, cyano, quaternary amino, —SO₃H, and —S(O)$_n$R, where R is alkyl, aryl, or heteroaryl and n is 0, 1 or 2.

The term "acyloxy" refers to the groups —O(O)C-alkyl, —O(O)C-cycloalkyl, —O(O)C-aryl, —O(O)C-heteroaryl, and —O(O)C-heterocyclyl. Unless otherwise constrained by the definition, all substituents may be optionally further substituted by alkyl, carboxy, carboxyalkyl, aminocarbonyl, hydroxy, alkoxy, halogen, $CF_3$, amino, substituted amino, cyano, quaternary amino, —SO₃H, or —S(O)$_n$R, where R is alkyl, aryl, or heteroaryl and n is 0, 1 or 2.

The term "aryl" refers to an aromatic carbocyclic group of 6 to 20 carbon atoms having a single ring (e.g., phenyl) or multiple rings (e.g., biphenyl), or multiple condensed (fused) rings (e.g., naphthyl or anthryl). Preferred aryls include phenyl, naphthyl and the like.

Unless otherwise constrained by the definition for the aryl substituent, such aryl groups can optionally be substituted with from 1 to 5 substituents, for example 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, phosphate, thiocarbonyl, aminothiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO₃H, —SO-alkyl, —SO-aryl,—SO-heteroaryl, —SO₂-alkyl, SO₂-aryl and —SO₂-heteroaryl. Unless otherwise constrained by the definition, all substituents may optionally be further substituted by 1 to 3 substituents chosen from alkyl, carboxy, carboxyalkyl, aminocarbonyl, hydroxy, alkoxy, halogen, $CF_3$, amino, substituted amino, cyano, quaternary amino, —SO₃H, and —S(O)$_n$R, where R is alkyl, aryl, or heteroaryl and n is 0, 1 or 2.

The term "aryloxy" refers to the group aryl- O—wherein the aryl group is as defined above, and includes optionally substituted aryl groups as also defined above. The term "arylthio" refers to the group R—S—, where R is as defined for aryl.

The term "amino" refers to the group —NH₂.

The term "substituted amino" refers to the group —NRR where each R is independently selected from the group consisting of hydrogen, alkyl, cycloalkyl, carboxyalkyl (for example, benzyloxycarbonyl), aryl, heteroaryl and heterocyclyl provided that both R groups are not hydrogen, or a group —Y-Z, in which Y is optionally substituted alkylene and Z is alkenyl, cycloalkenyl, or alkynyl. Unless otherwise constrained by the definition, all substituents may optionally be further substituted by 1-3 substituents chosen from alkyl, carboxy, carboxyalkyl, aminocarbonyl, hydroxy, alkoxy, halogen, $CF_3$, amino, substituted amino, cyano, quaternary amino, —SO₃H, and —S(O)$_n$R, where R is alkyl, aryl, or heteroaryl and n is 0, 1 or 2.

The term "quaternary amino" refers to the group —NRRR where each R is as defined for substituted amino. Any two of the R substituents may be joined to form a heterocyclic group as defined further herein.

The term "carboxyalkyl" refers to the groups —C(O)O-alkyl, —C(O)O-cycloalkyl, where alkyl and cycloalkyl, are as defined herein, and may be optionally further substituted by alkyl, alkenyl, alkynyl, alkoxy, halogen, $CF_3$, amino, substituted amino, cyano, quaternary amino, —SO₃H, or —S(O)$_n$R, in which R is alkyl, aryl, or heteroaryl and n is 0, 1 or 2.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, bicyclo[2.2.1]heptane, 1,3,3-trimethylbicyclo[2.2.1]hept-2-yl, (2,3,3-trimethylbicyclo[2.2.1]hept-2-yl), or cyclic alkyl groups to which is fused an aryl group, for example indane, and the like.

The term "substituted cycloalkyl" refers to cycloalkyl groups having from 1 to 5 substituents, and for example 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, phosphate, thiocarbonyl, aminothiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, quaternary amino, —SO₃H, —SO-alkyl, —SO-aryl,—SO-heteroaryl, —SO₂-alkyl, SO₂-aryl and —SO₂-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, $CF_3$, amino, substituted amino, cyano, quaternary amino, —$SO_3H$, and —$S(O)_nR$, where R is alkyl, aryl, or heteroaryl and n is 0, 1 or 2.

The term "halogen" or "halo" refers to fluoro, bromo, chloro, and iodo.

The term "acyl" denotes a group —C(O)R, in which R is hydrogen, optionally substituted alkyl, optionally substituted cycloalkyl, optionally substituted heterocyclyl, optionally substituted aryl, and optionally substituted heteroaryl.

The term "heteroaryl" refers to an aromatic group (i.e., unsaturated) comprising 1 to 15 carbon atoms and 1 to 4 heteroatoms selected from oxygen, nitrogen and sulfur within at least one ring.

Unless otherwise constrained by the definition for the heteroaryl substituent, such heteroaryl groups can be optionally substituted with 1 to 5 substituents, for example 1 to 3 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, phosphate, thiocarbonyl, aminothiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, substituted amino, quaternary amino, —$SO_3H$, —SO-alkyl, —SO-aryl, —SO-heteroaryl, —$SO_2$-alkyl, $SO_2$-aryl and —$SO_2$-heteroaryl.

Unless otherwise constrained by the definition, all substituents may optionally be further substituted by 1-3 substituents chosen from alkyl, carboxy, carboxyalkyl, aminocarbonyl, hydroxy, alkoxy, halogen, $CF_3$, amino, substituted amino, cyano, quaternary amino, —$SO_3H$, and —$S(O)_nR$, where R is alkyl, aryl, or heteroaryl and n is 0, 1 or 2. Such heteroaryl groups can have a single ring (e.g., pyridyl or furyl) or multiple condensed rings (e.g., indolizinyl, benzothiazolyl, or benzothienyl).

Examples of heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, tetrazole and the like as well as N-alkoxy-nitrogen containing heteroaryl compounds.

The term "heteroaralkyl" refers to a heteroaryl group covalently linked to an alkylene group, where heteroaryl and alkylene are defined herein. "Optionally substituted heteroaralkyl" refers to an optionally substituted heteroaryl group covalently linked to an optionally substituted alkylene group. Such heteroaralkyl groups are exemplified by 3-pyridylmethyl, quinolin-8-ylethyl, 4-methoxythiazol-2-ylpropyl, and the like.

The term "heteroaryloxy" refers to the group heteroaryl-O—.

The term "heterocyclyl" refers to a monoradical saturated or partially unsaturated group having a single ring or multiple condensed rings, having from 1 to 40 carbon atoms and from 1 to 10 hetero atoms, for example 1 to 4 heteroatoms, selected from nitrogen, sulfur, phosphorus, and/or oxygen within the ring wherein said sulfur and phosphorous can be in the following oxidation states —S—, —S(O)—, —S(O)2- and —P—, —P(O)—, and —P(O)2-, respectively.

Unless otherwise constrained by the definition for the heterocyclic substituent, such heterocyclic groups can be optionally substituted with 1 to 5, and for example 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, phosphate, thiocarbonyl, aminosulfinyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, quaternary amino, —$SO_3H$, —SO-alkyl, —SO-aryl, —SO-heteroaryl, —$SO_2$-alkyl, $SO_2$-aryl and —$SO_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, $CF_3$, amino, substituted amino, cyano, quaternary amino, —$SO_3H$, and —$S(O)_nR$, where R is alkyl, aryl, or heteroaryl and n is 0, 1 or 2. Heterocyclic groups can have a single ring or multiple condensed rings. Preferred heterocyclics include, but are not limited to, tetrahydrofuranyl, morpholino, and piperidinyl.

The term "thiol" refers to the group —SH.

The term "substituted alkylthio" refers to the group —S-substituted alkyl.

The term "heteroarylthiol" refers to the group —S-heteroaryl wherein the heteroaryl group is as defined above including optionally substituted heteroaryl groups as also defined above.

The term "sulfinyl" refers to a group —S(O)R, in which R is alkyl, aryl, or heteroaryl. "Substituted sulfinyl" refers to a group —S(O)R, in which R is substituted alkyl, substituted aryl, or substituted heteroaryl, as defined herein.

The term "sulfonyl" refers to a group —$S(O)_2R$, in which R is alkyl, aryl, or heteroaryl. "Substituted sulfonyl" refers to a group —$S(O)_2R$, in which R is substituted alkyl, substituted aryl, or substituted heteroaryl, as defined herein.

The term "keto" refers to a group —C(O)—. The term "thiocarbonyl" or "sulfinyl" refers to a group C(S)—. The term "carboxy" refers to a group —C(O)—OH.

"Optional" or "optionally" means that the subsequently described event or circumstance may or may not occur, and that the description includes instances where said event or circumstance occurs and instances in which it does not.

The term "compound of Formula I" is intended to encompass the compounds of the invention as disclosed, and the pharmaceutically acceptable salts, pharmaceutically acceptable esters, and prodrugs of such compounds. Additionally, the compounds of the invention may possess one or more asymmetric centers, and can be produced as a racemic mixture or as individual enantiomers or diastereoisomers. The number of stereoisomers present in any given compound of Formula I depends upon the number of asymmetric centers present (there are $2^n$ stereoisomers possible where n is the number of asymmetric centers). The individual stereoisomers may be obtained by resolving a racemic or non-racemic mixture of an intermediate at some appropriate stage of the synthesis, or by resolution of the compound of Formula I by conventional means. The individual stereoisomers (including individual enantiomers and diastereoisomers) as well as racemic and non-racemic mixtures of stereoisomers are encompassed within the scope of the present invention, all of which are intended to be depicted by the structures of this specification unless otherwise specifically indicated.

"Isomers" are different compounds that have the same molecular formula.

"Stereoisomers" are isomers that differ only in the way the atoms are arranged in space.

"Enantiomers" are a pair of stereoisomers that are non-superimposable mirror images of each other. A 1:1 mixture of a pair of enantiomers is a "racemic" mixture. The term "(±)" is used to designate a racemic mixture where appropriate.

"Diastereoisomers" are stereoisomers that have at least two asymmetric atoms, but which are not mirror-images of each other.

The absolute stereochemistry is specified according to the Cahn-Ingold-Prelog R—S system. When the compound is a pure enantiomer, the stereochemistry at each chiral carbon may be specified as either R or S. Resolved compounds whose absolute configuration is unknown are designated (+) or (−) depending on the direction (dextro- or laevorotary) in which they rotate the plane of polarized light at the wavelength of the sodium D line.

The term "therapeutically effective amount" refers to that amount of a compound of Formula I that is sufficient to effect treatment, as defined below, when administered to a mammal in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "treatment" or "treating" means any treatment of a disease in a mammal, including:
(i) preventing the disease, that is, causing the clinical symptoms of the disease not to develop;
(ii) inhibiting the disease, that is, arresting the development of clinical symptoms; and/or
(iii) relieving the disease, that is, causing the regression of clinical symptoms.

In many cases, the compounds of this invention are capable of forming acid and/or base salts by virtue of the presence of amino and/or carboxyl groups or groups similar thereto. The term "pharmaceutically acceptable salt" refers to salts that retain the biological effectiveness and properties of the compounds of Formula I, and which are not biologically or otherwise undesirable. Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Specific examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

A compound that is an agonist with high intrinsic efficacy evokes the maximal effect of which the biological system is capable. These compounds are known as "full agonists". They are able to elicit the maximum possible effect without occupying all the receptors, if the efficiency of coupling to the effector process is high. In contrast, "partial agonists" evoke a response but cannot evoke the maximal response of which the biological system is capable. They may have reasonable affinity but low intrinsic efficacy.

The term "therapeutically effective amount" refers to that amount of a compound of Formula I that is sufficient to effect treatment, as defined below, when administered to a mammal in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "coronary artery disease" means a chronic disease in which there is arteriosclerosis of the coronary arteries.

The term "atherosclerosis" refers to a form of arteriosclerosis in which deposits of yellowish plaques containing cholesterol, lipoid material, and lipophages are formed within the intima and inner media of large and medium-sized arteries.

The term "treatment" or "treating" means any treatment of a disease in a mammal, including:
(i) preventing the disease, that is, causing the clinical symptoms of the disease not to develop;
(ii) inhibiting the disease, that is, arresting the development of clinical symptoms; and/or
(iii) relieving the disease, that is, causing the regression of clinical symptoms.

Nomenclature

The compounds of the invention are numbered according to the following scheme:

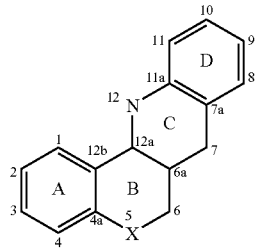

The naming and numbering of the compounds of the invention is illustrated with a representative compound of Formula I:

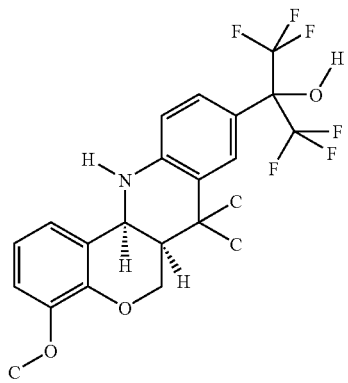

in which A and D are phenyl, $R^1$ and $R^2$ are methyl, $R^3$ is 3-methoxy, $R^4$, $R^5$, $R^6$, and $R^7$ are hydrogen, $R^8$ is 1,1,1,3,3,3-hexafluoro-2-hydroxypropan-2-yl, which is named 2-((12aS,6aR)-4-methoxy-7,7-dimethyl(7,12,12a,6a-tetrahydrochromano[4,3-b]quinolin-9-yl))-1,1,1,3,3,3-hexafluoropropan-2-ol. In the above structure, the BC cis ring juncture is indicated as (12aS, 6aR) as drawn, however, it is understood that this also represents (12aR, 6aS) cis compound, since these compounds are racemic. When a specific enantiomer is intended the naming convention will be indicated, for example, as (12aS*, 6aR*).

DETAILED DESCRIPTION OF THE INVENTION

Synthesis of the Compounds of Formula I

The compounds of Formula I in which X is oxygen may be prepared as shown in Reaction Scheme I.

REACTION SCHEME I

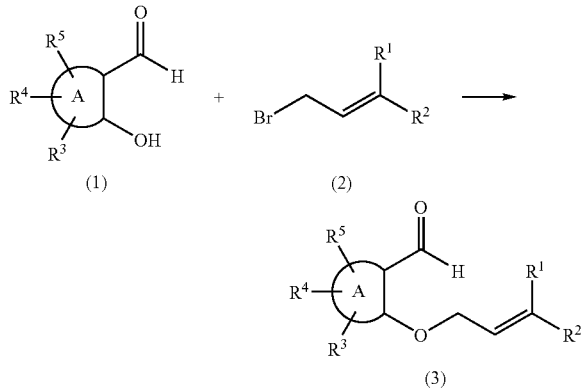

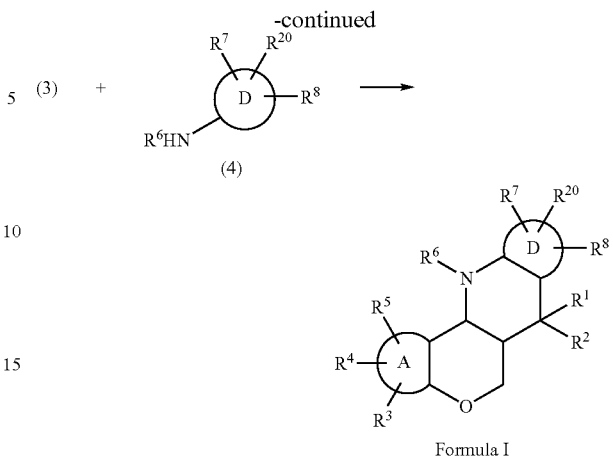

Formula I

Step 1

In general, the compound of formula (1) is reacted with a compound of formula (1) in a polar solvent, for example N,N-dimethylformamide, in the presence of a base, preferably an inorganic base, for example, potassium carbonate, at room temperature, for about 12-72 hours, preferably about 48 hours. When the reaction is substantially complete, the product of formula (3) is isolated by conventional means and used with no further purification.

Step 2

In general, the compound of formula (3) is reacted with a compound of formula (4) in an inert solvent, for example acetonitrile, in the presence of a catalytic amount of a strong acid, for example, trifluoroacetic acid. The reaction is conducted at room temperature or at about 50-100° C., preferably about 80° C., for about 4-24 hours, preferably about 12 hours. When the reaction is substantially complete, the product of Formula I is isolated using conventional means, for example, chromatography on silica gel or neutral alumina, and may be used without further purification.

Conventional heating is required for the preparation of the compound of Formula in which $R^6$ is optionally substituted less hindered lower alkyl, —C(O)$R^{12}$, or S(O)$_2R^{12}$. As before, the compound of formula (3) is generally reacted with the compound of formula (2) in an inert solvent, such as DMF, in the presence of a catalytic amount of a strong acid, for example, trifluoroacetic acid. The reaction is conducted at about 50-100° C., preferably about 90° C., for about 4-48 hours, preferably about 24 hours, and then isolated and purified as discussed above.

Microwave irradiation is useful for the preparation of the compound of Formula I in which $R^6$ is an optionally substituted hindered substituent, for example a cyclohexyl group. The compounds of formula (2) and (3) are subjected to the same reaction conditions as before, however, the reaction is conducted using microwave irradiation at about 100-220° C., preferably about 180° C., for about 5-60 minutes, preferably about 20 minutes.

Further Substitution on the D Ring

In those instances where $R^8$ or $R^{20}$ is a halogen, preferably bromo, the D ring can be further substituted by carrying out a Suzuki coupling, as shown in Reaction Scheme II.

REACTION SCHEME II

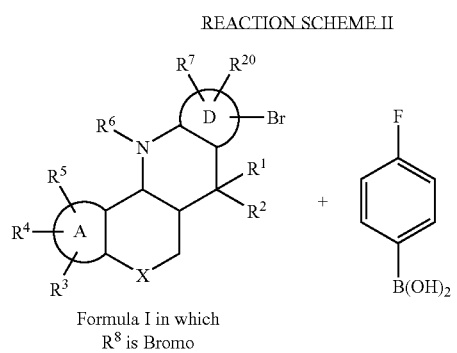

Formula I in which
R⁸ is Bromo

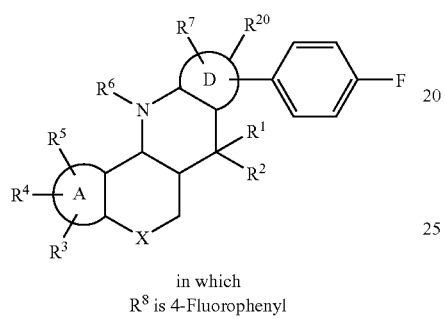

in which
R⁸ is 4-Fluorophenyl

As shown above, the compound of Formula I in which R⁸ is bromo is reacted with an appropriately substituted boronic acid derivative, for example with 4-fluorophenylboronic acid, in an aqueous solvent mixture, for example acetonitrile/aqueous sodium carbonate. The reaction is typically conducted in the presence of a catalyst, for example dichlorobis-(triphenylphosphine) palladium(II), at a temperature of about 150° C., under irradiation in a microwave, for about 10 minutes to about 1 hour. When the reaction is substantially complete, the product of Formula I is isolated by conventional means, for example by partitioning the crude reaction mixture between ethyl acetate/aqueous sodium hydroxide, separating the organic layer, removing the solvent under reduced pressure, followed by chromatography of the residue, preferably preparatory TLC.

In those instances where the R⁷, R⁸, or R²⁰ moiety has a terminal carboxylic acid group, the D ring can be further substituted to provide an aminocarbonyl linking moiety as shown in Reaction Scheme III.

REACTION SCHEME III

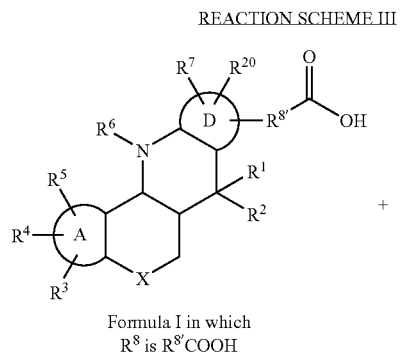

Formula I in which
R⁸ is R⁸'COOH

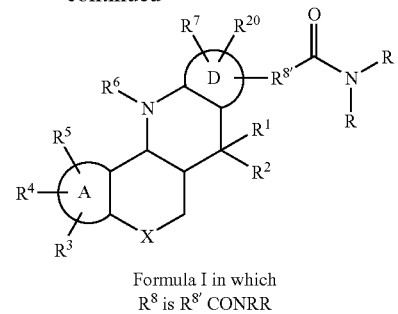

Formula I in which
R⁸ is R⁸' CONRR

In Reaction Scheme III, R⁸ is depicted as the D ring substituent having the terminal acidic moiety and R⁸' is the portion of R⁸ linking the terminal acid group with the D ring. The acidic compound of formula I is reacted with a primary or secondary amine in a polar solvent, for example N,N-dimethylformamide (DMF), in the presence of a coupling reagent, for example, EDCI, and a base, preferably an organic base, for example, triethylamine, at room temperature, for about 12-72 hours, preferably about 48 hours. When the reaction is substantially complete, the product of formula I is isolated by conventional means, for example, aqueous work up and chromatography on silica gel, and may be used without further purification.

It will be appreciated by those of skill in the art that a terminal carbocylic acid group can be easily achieved by hydrolyzing an analogous compound having terminal ethyl ester.

Terminal R⁷, R⁸, or R²⁰ cyano groups can also be further substituted to provide a tetrazole substituent as shown in Reaction Scheme IV.

REACTION SCHEME IV

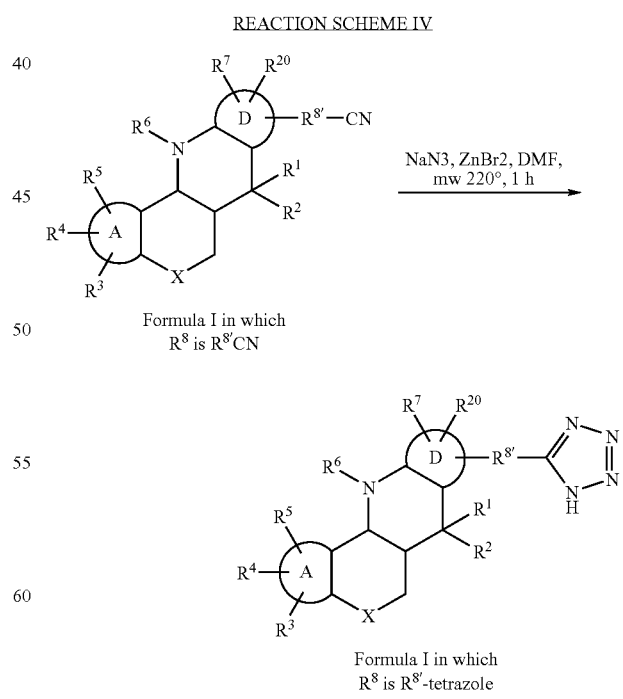

In this method, the cyano compound of formula I is reacted with sodium azide and zinc bromide in a polar solvent, for example DMF. The reaction mixture is subjected to microwave irradiation at 220° C. for 30 minutes to an hour and then cooled to room temperature. When the reaction is substantially complete, the product of formula I is isolated by conventional means, for example, aqueous work up and chromatography on silica gel, and may be used without further purification.

Terminal $R^7$, $R^8$, or $R^{20}$ thio groups can also be further substituted to provide a sulfonyl substituent as shown in Reaction Scheme V.

REACTION SCHEME V

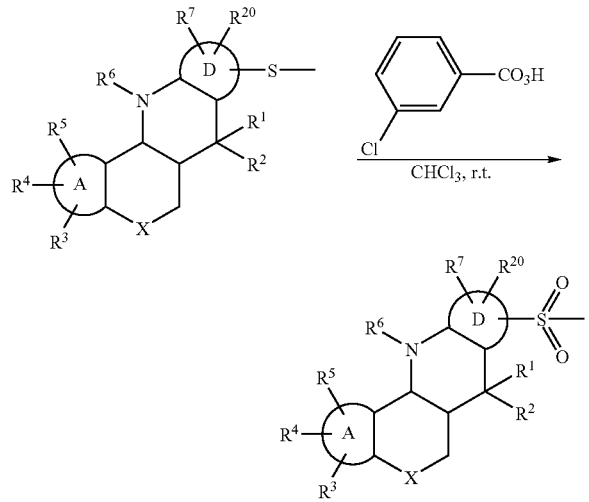

In this method, a cooled (0° C.) solution of the $R^8$ thio compound of formula I in anhydrous chloroform is reacted with 3-chloroperoxybenzoic acid. The reaction mixture is typically stirred at 0° C. for 5-10 minutes and then the ice bath removed. After about 30 minutes to an hour of stirring at room temperature, the reaction is substantially completed and the product of formula I is isolated by conventional means. Generally isolation and purification may be accomplished by filtering through a layer of dry sodium sulfate (top) and silica gel (bottom), followed aqueous work up and chromatography on silica gel.

It will be appreciated that the above substitutions and modification can be made to the D ring prior to formation of the compound of formula I, i.e., by modification of the compound of formula (4) prior to reaction with the formula (3) compound in Step 2 of Reaction Scheme I. An example of this is presented in Reaction Scheme VI.

REACTION SCHEME VI

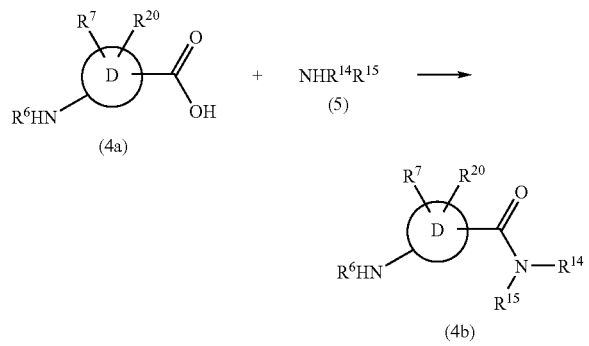

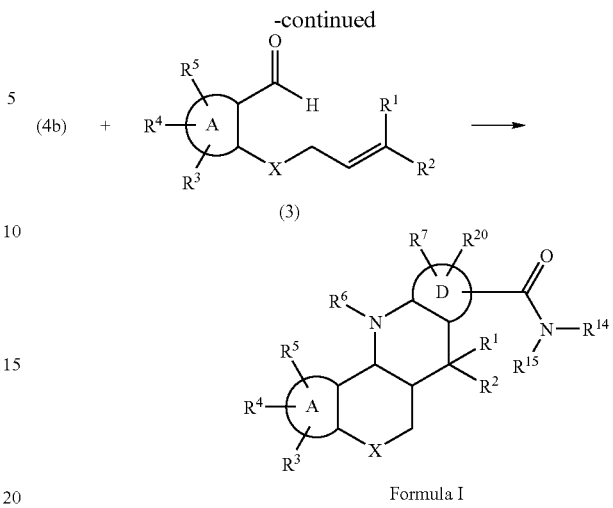

Formula I

Step 1

In general, an acidic variant of the formula (4) compound, compound (4a) is reacted with an amine of formula (5) in a polar solvent, for example DMF, in the presence of a coupling reagent, for example, EDCI, and a base, preferably an organic base, for example, triethylamine, at room temperature, for about 12-72 hours, preferably about 48 hours. When the reaction is substantially complete, the aminocarboxy substituted product of formula (4b), also a formula (4) compound, is isolated by conventional means, for example, aqueous work up and chromatography on silica gel, and may be used without further purification.

Step 2

The compound of formula (4a) is then reacted with a compound of formula (3) in an inert solvent, for example DMF, in the presence of a catalytic amount of a strong acid, for example, trifluoroacetic acid. The reaction is conducted at room temperature or at about 50-100° C., preferably about 80-90° C., or under microwave irradiation at about 150-240° C., preferably about 180° C., for about 10-40 minutes, preferably about 20 minutes. When the reaction is substantially complete, the product of Formula I is isolated using conventional means, for example, chromatography on silica gel or reverse-phase HPLC, and may be used without further purification.

Further Substitution on the A Ring

In those instances where $R^3$, $R^4$ or $R^5$ is a halogen, preferably iodo or bromo, the A ring can be further substituted by carrying out a Heck reaction, or as shown in Reaction Scheme VII.

REACTION SCHEME VII

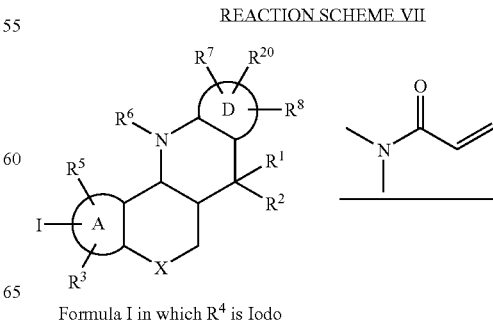

Formula I in which $R^4$ is Iodo

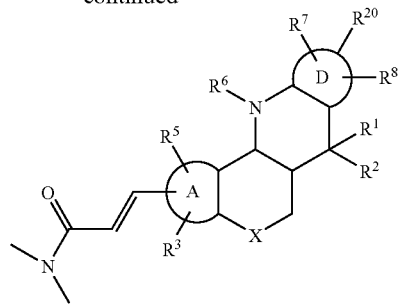

Formula I in which R⁴ is N,N-dimethylprop-2-enamide

As shown above, the compound of Formula I in which $R_4$ is iodo is reacted with dimethylacrylamide in an inert solvent, for example N,N-dimethylformamide, in the presence of a quarternary base, for example tetrabutylammonium chloride, a catalyst, for example palladium(II) diacetate, and a tertiary base, for example triethylamine. The mixture is heated to a temperature of about 60-100° C., for about 4-24 hours. When the reaction is substantially complete, the product of Formula I is isolated by conventional means.

If desired, the acrylamide derivative can then be reduced to an N,N-dimethyl-propanamide derivative by conventional reduction, for example with a mixture of nickel chloride/sodium borohydride. The reduction is typically carried out in an aqueous solvent, for example methanol/water, at about room temperature.

Alternatively, the A ring can be further substituted by reacting the halogenated compound with a boronic acid derivative of the desired R⁴ substituent, or as shown in Reaction Scheme VIII.

REACTION SCHEME VIII

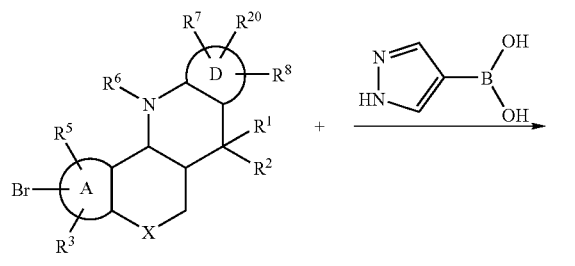

Formula I in which R⁴ is Bromo

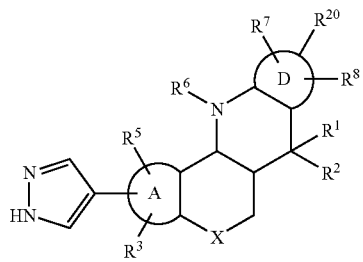

Formula I in which R⁴ is 1H-pyrazol-4-yl

As shown above, the compound of Formula I in which R⁴ is bromo or iodo is reacted with an appropriately substituted boronic acid derivative, for example with aromatic boronic acid or heterocyclic boronic acid, in an aqueous solvent mixture, for example dimethoxyethane (DME)/aqueous sodium carbonate. The reaction is typically conducted in the presence of a catalyst, for example dichlorobis-(triphenylphosphine) palladium(II), at a temperature of about 150° C., under irradiation in a microwave, for about 10 minutes to about 1 hour. When the reaction is substantially complete, the product of Formula I is isolated by conventional means, for example by filtrating through celite, partitioning the crude reaction mixture between ethyl acetate/aqueous lithium hydroxide, separating the organic layer, removing the solvent under reduced pressure, followed by chromatography of the residue, preferably preparatory TLC or reverse phase HPLC.

UTILITY, TESTING AND ADMINISTRATION

General Utility

The compounds of Formula I stimulate the expression of ABCA1 in mammalian cells, and may thereby increase cholesterol efflux and raise HDL levels in plasma. Thus, the compounds of Formula I are useful for treating conditions treatable by increasing ABCA1 expression including, but not limited to, coronary artery disease, dyslipidiemia and metabolic syndrome and may also be useful in treating other conditions related to high cholesterol/low HDL levels in mammals.

Testing

Activity testing is conducted as described in those patents and patent applications referenced above, and in the Examples below, and by methods apparent to one skilled in the art.

Pharmaceutical Compositions

The compounds of Formula I are usually administered in the form of pharmaceutical compositions. This invention therefore provides pharmaceutical compositions that contain, as the active ingredient, one or more of the compounds of Formula I, or a pharmaceutically acceptable salt or ester thereof, and one or more pharmaceutically acceptable excipients, carriers, including inert solid diluents and fillers, diluents, including sterile aqueous solution and various organic solvents, permeation enhancers, solubilizers and adjuvants. The compounds of Formula I may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. 17$^{th}$ Ed. (1985) and "Modern Pharmaceutics", Marcel Dekker, Inc. 3$^{rd}$ Ed. (G. S. Banker & C. T. Rhodes, Eds.).

Administration

The compounds of Formula I may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

One mode for administration is parental, particularly by injection. The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection, but less preferred in the context of the present invention. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the compound of Formula I in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Oral administration is another route for administration of the compounds of Formula I. Administration may be via capsule or enteric coated tablets, or the like. In making the pharmaceutical compositions that include at least one compound of Formula I, the active ingredient is usually diluted by an excipient and/or enclosed within such a carrier that can be in the form of a capsule, sachet, paper or other container. When the excipient serves as a diluent, in can be a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents.

The compositions of the invention can be formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902514; and 5,616,345. Another formulation for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. Nos. 5,023,252, 4,992, 445 and 5,001,139. Such patches may be constructed for continuous, pulsatile, or on demand delivery of pharmaceutical agents.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds of Formula I are effective over a wide dosage range and is generally administered in a pharmaceutically effective amount. Preferably, for oral administration, each dosage unit contains from 10 mg to 2 g of a compound of Formula I, more preferably from 10 to 700 mg, and for parenteral administration, preferably from 10 to 700 mg of a compound of Formula I, more preferably about 50-200 mg. It will be understood, however, that the amount of the compound of Formula I actually administered will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Preparation of a Compound of Formula (3)

A. Preparation of a Compound of Formula (3) in which A is Phenyl, $R^1$ and $R^2$ are Methyl, $R^3$ is 2-Methoxy $R^4$ and $R^5$ are Hydrogen, and X is Oxygen

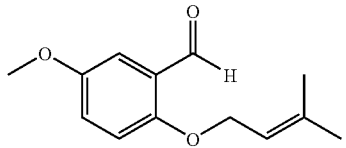

To a solution of 2-hydroxy-5-methoxybenzaldehyde (7.6 g, 50 mmol) in dry N,N-dimethylformamide (100 mL) was added potassium carbonate (10.4 g), followed by 1-bromo-3-methylbut-2-ene (10.0 g, 67 mmol). The mixture was stirred at room temperature for 48 hours and ethyl acetate added. Sufficient 1M hydrochloric acid was cautiously added to neutralize the base, and the organic layer was washed with water three times, followed by brine, and dried over magnesium sulfate. The mixture was filtered, and solvent removed from the filtrate under reduced pressure, to provide 5-methoxy-2-(3-methylbut-2-enyloxy)benzaldehyde.

$^1$H NMR (400 MHz, CDCl$_3$) δ 1.73(s, 3H), 1.79(s, 3H), 3.8(s, 3H), 4.6(d, J=6.6 Hz, 2H), 5.48(m, 1H), 6.96(d, J=9.3 Hz, 1H), 7.12(dd, J=9.0, 3.5 Hz, 1H), 7.52(d, J=3.5 Hz, 1H), 10.45(s, 1H)

B. Preparation of a Compound of Formula (3), varying $R^1$, $R^2$, $R^3$, and $R^4$ Similarly, following the procedure of 1A above, but replacing 2-hydroxy-5-methoxybenzaldehyde with other formula (1) compounds or replacing 1-bromo-3-methylbut-2-ene with other formula (2) compounds, the following compounds of formula (3) were prepared:

2-(3-methylbut-2-enyloxy)benzaldehyde;
5-bromo-2-(3-methylbut-2-enyloxy)benzaldehyde;
3-methoxy-2-(3-methylbut-2-enyloxy)benzaldehyde;
6-methoxy-2-(3-methylbut-2-enyloxy)benzaldehyde;
3-ethoxy-2-(3-methylbut-2-enyloxy)benzaldehyde;
3-methyl-2-(3-methylbut-2-enyloxy)benzaldehyde;
4-carboxy-2-(3-methylbut-2-enyloxy)benzaldehyde;
3-fluoro-2-(3-methylbut-2-enyloxy)benzaldehyde;
5-trifluoromethyloxy-2-(3-methylbut-2-enyloxy)benzaldehyde;
3-methoxy-5-bromo-2-(3-methylbut-2-enyloxy)benzaldehyde;
4-methoxy-6-bromo-2-(3-methylbut-2-enyloxy)benzaldehyde;
3-methoxy-5-chloro-2-(3-methylbut-2-enyloxy)benzaldehyde;
3,5-difluoro-2-(3-methylbut-2-enyloxy)benzaldehyde;
3,5-dichloro-2-(3-methylbut-2-enyloxy)benzaldehyde;
2,3-bis(3-methylbut-2-enyloxy)benzaldehyde;
3-methylbut-2-enyl 3-formyl-4-(3-methylbut-2-enyloxy)benzoate;
3-methylbut-2-enyl 4-formyl-3-(3-methylbut-2-enyloxy)benzoate;
2-(cinnamyloxy)-6-methoxybenzaldehyde; and
2-(3-methylbut-2-enyloxy)-3,6-dimethylbenzaldehyde.

C. Preparation of a Compound of Formula (3), varying $R^1$, $R^2$, $R^3$, $R^4$, $R^5$, and X Similarly, following the procedure of 1A above, but replacing 2-hydroxy-5-methoxybenzaldehyde with other formula (1) compounds or replacing 1-bromo-3-methylbut-2-ene with other formula (2) compounds, the following compounds of formula (3) are prepared.

5-methoxy-2-(3-methylbut-2-enylthio)benzaldehyde;
2-(3-methylbut-2-enylthio)benzaldehyde
5-bromo-2-(3-methylbut-2-enylthio)benzaldehyde;
3-methoxy-2-(3-methylbut-2-enylthio)benzaldehyde;
6-methoxy-2-(3-methylbut-2-enylthio)benzaldehyde;
3-ethoxy-2-(3-methylbut-2-enylthio)benzaldehyde;
3-methyl-2-(3-methylbut-2-enylthio)benzaldehyde;
4-carboxy-2-(3-methylbut-2-enylthio)benzaldehyde;
3-fluoro-2-(3-methylbut-2-enylthio)benzaldehyde;
5-trifluoromethyloxy-2-(3-methylbut-2-enylthio)benzaldehyde;
3-methoxy-5-bromo-2-(3-methylbut-2-enylthio)benzaldehyde;
4-methoxy-6-bromo-2-(3-methylbut-2-enylthio)benzaldehyde;
3-methoxy-5-chloro-2-(3-methylbut-2-enylthio)benzaldehyde;
3,5-difluoro-2-(3-methylbut-2-enylthio)benzaldehyde;
3,5-dichloro-2-(3-methylbut-2-enylthio)benzaldehyde;
2,3-bis(3-methylbut-2-enylthio)benzaldehyde;
3-methylbut-2-enyl 3-formyl-4-(3-methylbut-2-enylthio)benzoate; and
3-methylbut-2-enyl 4-formyl-3-(3-methylbut-2-enylthio)benzoate.

D. Preparation of a Compound of Formula (3), varying A, $R^1$, $R^2$, $R^3$, $R^4$, $R^5$, and X Similarly, following the procedure of 1A above, but replacing 2-hydroxy-5-methoxybenzaldehyde with other formula (1) compounds or replacing 1-bromo-3-methylbut-2-ene with other formula (2) compounds, other compounds of formula (3) are prepared.

EXAMPLE 2

Preparation of a Compound of Formula (3)

A. Preparation of a Compound of Formula (3) in which A is Phenyl, $R^1$ is Methyl, $R^2$ is 3-Methylbut-2-enyl, $R^3$ is 2-Methoxy, $R^4$ and $R^5$ are Hydrogen, and X is Oxygen

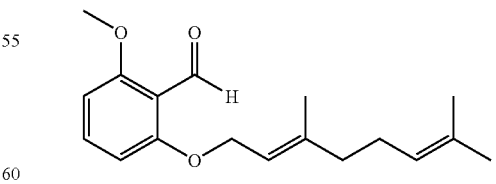

To a solution of 2-hydroxy-6-methoxybenzaldehyde (4.72 g, 30.43 mmol) in dry DMF (50 ml) was added geranyl bromide (7.5 g, 33.50 mmol) followed by solid potassium carbonate (5.5 g, 39.86 mmol). The mixture was stirred at room temperature for 48 h. The suspension was filtered through a layer of dry sodium sulfate (top) and silica gel (bottom), washed with 200 ml ethyl acetate and decanted into a separatory funnel. The mixture was washed sequentially with aqueous ammonium chloride, water (twice), brine, and the organic phase was dried over $Na_2SO_4$. The solution was concentrated in vacuo on a rotovap. The brown gel material was then purified by chromatography via silica gel using 8:2 hexanes:ethyl acetate eluent to provide 2-((E)-3,7-dimethylocta-2,6-dienyloxy)-6-methoxybenzaldehyde as pale yellow oil.

$^1$H NMR (400 MHz, $CDCl_3$) δ 10.56 (s, 1H ); 7.47 (t, aromatic 1H, J=8.60 Hz); 6.604 (d, 1H, J=8.22 Hz); 6.59 (d, 1H, J=8.22 Hz); 5.51 (td, 1H, J=6.65 and 1.17 Hz); 5.11 (m, 1H); 4.67 (d, 2H, J=6.65 Hz); 3.95 (s, 3H); 2.16 (m, 4H); 1.50-1.80 (s, 9H).

B. Preparation of a Compound of Formula (3), varying $R^1$, $R^2$, $R^3$ and $R^4$ Similarly, following the procedure of 2A above, but replacing 2-hydroxy-5-methoxybenzaldehyde with other formula (1) compounds or replacing geranyl bromide with other formula (2) compounds, other compounds of formula (3) are prepared.

EXAMPLE 3

Preparation of a Compound of Formula I

A. Preparation of a Compound of Formula I in which A and D are Phenyl, $R^1$ and $R^2$ are Methyl, $R^3$ is 3-Methoxy, $R^4$, $R^5$, $R^6$, $R^7$ and $R^8$ are Hydrogen, $R^{20}$ is 1,1,1,3,3,3-Hexafluoromethanol, and X is Oxygen A solution of 5-methoxy-2-(3-methylbut-2-enyloxy)benzaldehyde (1.1 g, 5 mmol), 2-(4-aminophenyl)-1,1,1,3,3,3-hexafluoropropan-2-ol (1.3 g, 5 mmol) and a catalytic amount of trifluoroacetic acid in acetonitrile (15 ml) was heated at 80° C. for 12 hours. After cooling, the solvent was removed under reduced pressure, and the residue chromatographed on silica gel (150 g), eluting with 30% ethyl acetate/hexanes, providing 1,1,1,3,3,3-hexafluoro-2-(2-methoxy-7,7-dimethyl(7,12, 12a,6a-tetrahydrochromano[4,3-b]quinolin-9-yl))propan-2-ol (as a 1:1 mixture of cis/trans isomers).

B. Preparation of a Compound of Formula I, varying $R^1$, $R^2$, $R^3$, $R^4$, $R^5$, $R^6$, $R^7$, $R^8$, $R^{20}$, and X Similarly, following the procedure of 3A above, but replacing 5-methoxy-2-(3-methylbut-2-enyloxy)benzaldehyde with other formula (3) compounds or replacing 2-(4-aminophenyl)-1,1,1,3,3,3-hexafluoropropan-2-ol with other compounds of formula (4), the following compounds of Formula I were prepared:

2-(2-bromo-7,7-dimethyl(7,12,12a,6a-tetrahydrochromano[4,3-b]quinolin-9-yl))-1,1,1,3,3,3-hexafluoropropan-2-ol;

2-((6aS,12aR)-2-bromo-7,7-dimethyl(7,12,12a,6a-tetrahydrochromano[4,3-b]quinolin-9-yl))-1,1,1,3,3,3-hexafluoropropan-2-ol;

2-((12aS,6aS)-2-bromo-7,7-dimethyl(7,12,12a,6a-tetrahydrochromano[4,3-b]quinolin-9-yl))-1,1,1,3,3,3-hexafluoropropan-2-ol;

2-(2-bromo-7,7-dimethyl-7,12,12a,6a-tetrahydrochromano[4,3 -b]quinolin-9-yl)acetic acid;

2-bromo-7,7-dimethyl-7,12,12a,6a-tetrahydrochromano [4,3-b]quinoline-9-carboxamide;

methyl 2-bromo-1 0-methoxy-7,7-dimethyl-7,12,12a,6a-tetrahydrochromano[4,3-b]quinoline-9-carboxylate;

1,1,1,3,3,3-hexafluoro-2-(2-methoxy-7,7-dimethyl(7,12, 12a,6a-tetrahydrochromano[4,3-b]quinolin-9-yl))propan-2-ol;

1,1,1,3,3,3-hexafluoro-2-(4-methoxy-7,7-dimethyl(7,12, 12a,6a-tetrahydrochromano[4,3-b]quinolin-9-yl))propan-2-ol;

2-[7,7-dimethyl-2-(trifluoromethoxy)(7,12,12a,6a-tetrahydrochromano[4,3-b]quinolin-9-yl)]-1,1,1,3,3,3-hexafluoropropan-2-ol;

2-[(12aS,6aS)-7,7-dimethyl-2-(trifluoromethoxy)(7,12, 12a,6a-tetrahydrochromano[4,3-b]quinolin-9-yl)]-1,1,1,3,3, 3-hexafluoropropan-2-ol;

3-methylbut-2-enyl (6aS, 12aR)-9-(dihydroxyboramethyl)-7,7-dimethyl-7,12,12a,6a-tetrahydrochromano[4,3-b] quinoline-3-carboxylate;

3-methylbut-2-enyl 9-(dihydroxyboramethyl)-7,7-dimethyl-7,12,12a,6a-tetrahydrochromano[4,3-b]quinoline-3-carboxylate;

3-methylbut-2-enyl 7,7-dimethyl-9-[2,2,2-trifluoro-1-hydroxy-1-(trifluoromethyl)ethyl]-7,12,12a,6a-tetrahydrochromano[4,3-b]quinoline-3-carboxylate;

3-methylbut-2-enyl 7,7-dimethyl-9-[2,2,2-trifluoro-1-hydroxy-1-(trifluoromethyl)ethyl]-7,12,12a,6a-tetrahydrochromano[4,3-b]quinoline-2-carboxylate;

7,7-dimethyl-9-[2,2,2-trifluoro-1-hydroxy-1-(trifluoromethyl)ethyl]-7,12,12a,6a-tetrahydrochromano[4,3-b]quinoline-3-carboxylic acid;

3 -methylbut-2-enyl 9-(dihydroxyboramethyl)-7,7-dimethyl-7,12,12a,6a-tetrahydrochromano[4,3-b]quinoline-2-carboxylate;

7,7-dimethyl-9-[2,2,2-trifluoro-1-hydroxy-1-(trifluoromethyl)ethyl]-7,12,12a,6a-tetrahydrochromano[4,3-b]quinoline-2-carboxylic acid;

9-(dihydroxyboramethyl)-7,7-dimethyl-7,12-dihydro-6H-chromeno[4,3-b]quinoline-3-carboxylic acid;

1,1,1,3,3,3-hexafluoro-2-(4,7,7-trimethyl(7,12,12a,6a-tetrahydrochromano[4,3-b]quinolin-9-yl))propan-2-ol;

4-methoxy-7,7-dimethyl-9-(1,2,3,4-tetraazol-5-yl)-7,12, 12a,6a-tetrahydrochromano[4,3-b]quinoline;

4-((6aS,12aR)-4-methoxy-7,7-dimethyl-7,12,12a,6a-tetrahydrochromano[4,3-b]quinolin-9-yl)-1,4-thiazaperhydroine-1,1-dione;

4-(4-methoxy-7,7-dimethyl-7,12,12a,6a-tetrahydrochromano[4,3-b]quinolin-9-yl)-1,4-thiazaperhydroine-1,1-dione;

2-(4-ethoxy-7,7-dimethyl(7,12,12a,6a-tetrahydrochromano[4,3-b]quinolin-9-yl))-1,1,1,3,3,3-hexafluoropropan-2-ol;

4-methoxy-7,7-dimethyl-7,12,12a,6a-tetrahydrochromano[4,3-b]quinoline-9-carboxamide;

1,1,1,3,3,3-hexafluoro-2-(1-methoxy-7,7-dimethyl(7,12, 12a,6a-tetrahydrochromano[4,3-b]quinolin-9-yl))propan-2-ol;

2-[7,7-dimethyl-4-(3-methylbut-2-enyloxy)(7,12,12a,6a-tetrahydrochromano[4,3-b]quinolin-9-yl)]-1,1,1,3,3,3-hexafluoropropan-2-ol;

2-(4-methoxy-7,7-dimethyl-7,12,12a,6a-tetrahydrochromano[4,3-b]quinolin-9-yl)acetic acid;

3-((6aS,12aR)-4-methoxy-7,7-dimethyl-7,12,12a,6a-tetrahydrochromano[4,3-b]quinolin-9-yl)propanoic acid;

3-((12aR,6aR)-4-methoxy-7,7-dimethyl-7,12,12a,6a-tetrahydrochromano[4,3-b]quinolin-9-yl)propanoic acid;

4,7,7-trimethyl-7,12,12a,6a-tetrahydrochromano[4,3-b]quinoline-9-carboxamide;

4-ethoxy-7,7-dimethyl-7,12,12a,6a-tetrahydrochromano[4,3-b]quinoline-9-carboxamide;

4,7,7-trimethyl-7,12,12a,6a-tetrahydrochromano[4,3-b]quinoline;

(12aS)-4,7,7-trimethyl-7,12,12a,6a-tetrahydrochromano[4,3-b]quinoline;

1,1,1,3,3,3-hexafluoro-2-(4-methoxy-7,7-dimethyl(7,12,12a,6a-tetrahydrochromano[4,3-b]quinolin-9-yl))propan-2-ol;

2-((6aR)-4-methoxy-7,7-dimethyl(7,12,12a,6a-tetrahydrochromano[4,3-b]quinolin-9-yl))-1,1,1,3,3,3-hexafluoropropan-2-ol;

(6aS,12aR)-4-methoxy-7,7-dimethyl-7,12,12a,6a-tetrahydrochromano[4,3-b]quinoline;

(12aS,6aS)-4-methoxy-7,7-dimethyl-7,12,12a,6a-tetrahydrochromano[4,3-b]quinoline;

4-ethoxy-7,7-dimethyl-9-(trifluoromethyl)-7,12,12a,6a-tetrahydrochromano[4,3-b]quinoline;

1-(4-ethoxy-7,7-dimethyl-7,12,12a,6a-tetrahydrochromano[4,3-b]quinolin-9-yl)ethan-1-one;

1-(1-methoxy-7,7-dimethyl-7,12,12a,6a-tetrahydrochromano[4,3-b]quinolin-9-yl)ethan-1-one;

1-methoxy-7,7-dimethyl-9-(trifluoromethy;1)-7,12,12a,6a-tetrahydrochromano[4,3-b]quinoline;

1-methoxy-7,7-dimethyl-7,12,12a,6a-tetrahydrochromano[4,3-b]quinoline-9-carboxamide;

(6aS,12aR)-4-methoxy-7,7-dimethyl-9-(methylethyl)-7,12,12a,6a-tetrahydrochromano[4,3-b]quinoline;

(12aS,6aS)-4-methoxy-7,7-dimethyl-9-(methylethyl)-7,12,12a,6a-tetrahydrochromano[4,3-b]quinoline;

(6aS,12aR)-9-fluoro-4-methoxy-7,7-dimethyl-7,12,12a,6a-tetrahydrochromano[4,3-b]quinoline;

(12aS,6aS)-4-methoxy-7,7-dimethyl-7,12,12a,6a-tetrahydrochromano[4,3-b]quinoline-9-carboxylic acid;

4-fluoro-7,7-dimethyl-7,12,12a,6a-tetrahydrochromano[4,3-b]quinoline-9-carboxamide;

1,1,1,3,3,3-hexafluoro-2-(4-fluoro-7,7-dimethyl(7,12,12a,6a-tetrahydrochromano[4,3-b]quinolin-9-yl))propan-2-ol;

((6aS,12aR)-4-methoxy-7,7-dimethyl(7,12,12a,6a-tetrahydrochromano[4,3-b]quinolin-9-yloxy))trifluoromethane;

(12aS,6aR)-1-methoxy-7,7-dimethyl-7,12,12a,6a-tetrahydrochromano[4,3-b]quinoline;

(12aS,6aR)-1-methoxy-7,7-dimethyl-9-(methylethyl)-7,12,12a,6a-tetrahydrochromano[4,3-b]quinoline;

(12aS,6aR)-9-fluoro-1-methoxy-7,7-dimethyl-7,12,12a,6a-tetrahydrochromano[4,3-b]quinoline;

(12aS,6aR)-9-ethoxy-1-methoxy-7,7-dimethyl-7,12,12a,6a-tetrahydrochromano[4,3-b]quinoline;

(12aS,6aR)-1-methoxy-7,7-dimethyl-7,12,12a,6a-tetrahydrochromano[4,3-b]quinoline-9-carboxylic acid;

10-(1H-1,2,3,4-tetraazol-5-yl)(12aS,6aR)-1-methoxy-7,7-dimethyl-7,12,12a,6a-tetrahydrochromano[4,3-b]quinoline;

((12aS,6aR)-1-methoxy-7,7-dimethyl(7,12,12a,6a-tetrahydrochromano[4,3-b]quinolin-9-yloxy))trifluoromethane;

amino(4-methoxy-7,7-dimethyl(7,12,12a,6a-tetrahydrochromano[4,3-b]quinolin-9-yl))methane-1-thione;

{[(4-methoxy-7,7-dimethyl(7,12,12a,6a-tetrahydrochromano[4,3-b]quinolin-9-yl))methyl]sulfonyl}methylamine;

methylethyl 3-(4-methoxy-7,7-dimethyl-7,12,12a,6a-tetrahydrochromano[4,3-b]quinolin-9-yl)benzoate;

methylethyl 3-(4-methoxy-7,7-dimethyl-7,12-dihydro-6H-chromeno[4,3-b]quinolin-9-yl)benzoate;

(12aS,6aR)-1-methoxy-7,7-dimethyl-9-(1,3-oxazol-5-yl)-7,12,12a,6a-tetrahydrochromano[4,3-b]quinoline;

(12aS,6aR)-1-methoxy-7,7-dimethyl-7,12,12a,6a-tetrahydrochromano[4,3-b]quinoline-10-carbonitrile;

2-((6aS,12aR)-1-bromo-4-methoxy-7,7-dimethyl(7,12,12a,6a-tetrahydrochromano[4,3-b]quinolin-9-yl))-1,1,1,3,3,3-hexafluoropropan-2-ol;

2-((6aS,12aR)-2-bromo-4-methoxy-7,7-dimethyl(7,12,12a,6a-tetrahydrochromano[4,3-b]quinolin-9-yl))-1,1,1,3,3,3-hexafluoropropan-2-ol;

2-((12aR,6aR)-2-bromo-4-methoxy-7,7-dimethyl(7,12,12a,6a-tetrahydrochromano[4,3-b]quinolin-9-yl))-1,1,1,3,3,3-hexafluoropropan-2-ol;

2-(2,4-difluoro-7,7-dimethyl(7,12,12a,6a-tetrahydrochromano[4,3-b]quinolin-9-yl))-1,1,1,3,3,3-hexafluoropropan-2-ol;

2-(2,4-dichloro-7,7-dimethyl(7,12,12a,6a-tetrahydrochromano[4,3-b]quinolin-9-yl))-1,1,1,3,3,3-hexafluoropropan-2-ol;

2-(2-chloro-4,7,7-trimethyl(7,12,12a,6a-tetrahydrochromano[4,3-b]quinolin-9-yl))-1,1,1,3,3,3-hexafluoropropan-2-ol;

2-((6aS,12aR)-7,7-dimethyl(7,12,12a,6a-tetrahydrochromano[4,3-b]quinolin-9-yl))-1,1,1,3,3,3-hexafluoropropan-2-ol;

(12aS,6aR)-1-methoxy-7,7-dimethyl-9-(1,2,3,4-tetraazol-5-yl)-7,12,12a,6a-tetrahydrochromano[4,3-b]quinoline;

4-((12aS,6aR)-1-methoxy-7,7-dimethyl-7,12,12a,6a-tetrahydrochromano[4,3-b]quinolin-9-yl)-1,4-thiazaperhydroine-1,1-dione;

(12aS,6aR)-1-methoxy-7,7-dimethyl-9-(1,2,3-thiadiazol-4-yl)-7,12,12a,6a-tetrahydrochromano[4,3-b]quinoline; and 1-methoxy-7,7-dimethyl-9-(4-methyl(1,2,4-triazol-3-yl))-7,12,12a,6a-tetrahydrochromano[4,3-b]quinoline.

9-bromo-4-methoxy-7,7-dimethyl-7,12,12a,6a-tetrahydrochromano[4,3-b]quinoline;

4-methoxy-7,7-dimethyl-9-(1,2,3,4-tetraazol-5-ylmethyl)-7,12,12a,6a-tetrahydrochromano[4,3-b]quinoline;

2-((12aS,6aR)-4-methoxy-7,7-dimethyl-2-phenyl(7,12,12a,6a-tetrahydrochromano[4,3-b]quinolin-9-yl))-1,1,1,3,3,3-hexafluoropropan-2-ol;

1-bromo-9-ethoxy-4-methoxy-7,7-dimethyl-7,12,12a,6a-tetrahydrochromano[4,3-b]quinoline;

1-bromo-4-methoxy-7,7-dimethyl-9-(1,3-oxazol-5-yl)-7,12,12a,6a-tetrahydrochromano[4,3-b]quinoline;

1-(1-bromo-4-methoxy-7,7-dimethyl-7,12,12a,6a-tetrahydrochromano[4,3-b]quinolin-9-yl)ethan-1-one;

1-bromo-4-methoxy-7,7-dimethyl-7,12,12a,6a-tetrahydrochromano[4,3-b]quinoline-9-carboxamide;

amino(1-bromo-4-methoxy-7,7-dimethyl(7,12,12a,6a-tetrahydrochromano[4,3-b]quinolin-9-yl))methane-1-thione;

1-bromo-4-methoxy-7,7-dimethyl-9-(methylethoxy)-7,12,12a,6a-tetrahydrochromano[4,3-b]quinoline;

(12aS,6aR)-1-methoxy-7,7-dimethyl-9-(1,2,3,4-tetraazol-5-ylmethyl)-7,12,12a,6a-tetrahydrochromano[4,3-b]quinoline;

(12aS,6aR)-9-bromo-1-methoxy-7,7-dimethyl-7,12,12a,6a-tetrahydrochromano[4,3-b]quinoline;

(12aS,6aR)-9-bromo-4-methoxy-7,7-dimethyl-7,12,12a,6a-tetrahydrochromano[4,3-b]quinoline;

(12aS,6aS)-9-bromo-4-methoxy-7,7-dimethyl-7,12,12a,6a-tetrahydrochromano[4,3-b]quinoline;

9-(tert-butyl)-1-methoxy-7,7-dimethyl-7,12,12a,6a-tetrahydrochromano[4,3-b]quinoline;

{[(1-methoxy-7,7-dimethyl(7,12,12a,6a-tetrahydrochromano[4,3-b]quinolin-9-yl))methyl]sulfonyl}methylamine;

diethoxy[(1-methoxy-7,7-dimethyl(7,12,12a,6a-tetrahydrochromano[4,3-b]quinolin-9-yl))methyl]phosphino-1-one;

[(2-chloro-4-methoxy-7,7-dimethyl(7,12,12a,6a-tetrahydrochromano[4,3-b]quinolin-9-yl))methyl]diethoxyphosphino-1-one;

1-(2-chloro-4-methoxy-7,7-dimethyl(7,12,12a,6a-tetrahydrochromano[4,3-b]quinolin-9-yl))-2-methoxybenzene;

1-(4-fluoro-7,7-dimethyl-7,12,12a,6a-tetrahydrochromano[4,3-b]quinolin-9-yl)ethan-1-one;

4-fluoro-7,7-dimethyl-9-(methylethoxy)-7,12,12a,6a-tetrahydrochromano[4,3-b]quinoline;

(12aS)-4-fluoro-7,7-dimethyl-9-(methylethoxy)-7,12,12a,6a-tetrahydrochromano[4,3-b]quinoline;

4-fluoro-9-(2-methoxyphenyl)-7,7-dimethyl-7,12-dihydro-6H-chromeno[4,3-b]quinolin-12-ol;

(2-chloro-4-methoxy-7,7-dimethyl(7,12,12a,6a-tetrahydrochromano[4,3-b]quinolin-9-yl))[(4-methylphenyl)sulfonyl]amine;

(12aS,6aR)-1-methoxy-7,7-dimethyl-9-(2-methyl(1,3-thiazol-4-yl))-7,12,12a,6a-tetrahydrochromano [4,3-b]quinoline;

12aS,6aR)-1-methoxy-7,7-dimethyl-9-pyrazol-3-yl-7,12,12a,6a-tetrahydrochromano[4,3-b]quinoline;

ethyl 2-((12aS,6aR)-1-methoxy-7,7-dimethyl-7,12,12a,6a-tetrahydrochromano[4,3-b]quinolin-9-yl)-1,3-oxazole-4-carboxylate;

(6aS,12aR)-7-methoxy-13,13-dimethyl-6,13,12a,6a-tetrahydrobenzothiazolo[6,7-b]chromano[3,4-e]pyridine;

(6aS,12aR)-7-methoxy-13,13-dimethyl-6,13,12a,6a-tetrahydro-1H-chromano[3,4-e]indazolo[6,7-b]pyridine;

(6aS,12aR)-7-methoxy-2,13,13-trimethyl-6,13,12a,6a-tetrahydrobenzothiazolo[5,4-b]chromano[3,4-e]pyridine; and (12bS,6aR)-12-methoxy-6,6-dimethyl-6,13,12b,6a-tetrahydrochromano[4,3-b]1,2,5-thiadiazolo[3,4-h]quinoline (12aS,6aR)-1-methoxy-7,7-dimethyl-9-methylthio-7,12,12a,6a-tetrahydrochromano[4,3-b]quinoline;

1,1,1,3,3,3-hexafluoro-2-(1-methoxy-7-phenyl(7,12,12a,6a-tetrahydrochromano[4,3-b]quinolin-9-yl))propan-2-ol;

((7S,12aS,6aR)-1-methoxy-7-phenyl(7,12,12a,6a-tetrahydrochromano[4,3-b]quinolin-9-yl))—N,N-dimethylcarboxamide;

(7S,12aS,6aR)-1-methoxy-9-morpholin-4-yl-7-phenyl-7,12,12a,6a-tetrahydrochromano[4,3-b]quinoline;

(12aS,7R,6aR)-1-methoxy-7-methyl-7-(4-methylpent-3-enyl)-7,12,12a,6a-tetrahydrochromano[4,3-b]quinoline-9-carbonitrile;

(12aS,7R,6aR)-1-methoxy-7-methyl-7-(4-methylpent-3-enyl)-9-(1,3-oxazol-5-yl)-7,12,12a,6a-tetrahydrochromano[4,3-b]quinoline;

4-{[(12aS,7R,6aR)-1-methoxy-7-methyl-7-(4-methylpent-3-enyl)-7,12,12a,6a-tetrahydrochromano[4,3-b]quinolin-9-yl]methyl}-1,4-thiazaperhydroine-1,1-dione; and methyl (12aS,7R,6aR)-1-methoxy-7-methyl-7-(4-methylpent-3-enyl)-7,12,12a,6a-tetrahydrochromano[4,3-b]quinoline-9-carboxylate.

ethyl 1-((6aR,12aS)-6a,7,12,12a-tetrahydro-1-methoxy-7,7-dimethyl-6H-chromeno[4,3-b]quinolin-9-yl)-1H-pyrazole-4-carboxylate;

ethyl 1-((6aR,12aS)-6a,7,12,12a-tetrahydro-1-methoxy-7,7-dimethyl-6H-chromeno[4,3-b]quinolin-9-yl)-5-methyl-1H-pyrazole-4-carboxylate;

(6aR,12aS)-2-bromo-6a,7,12,12a-tetrahydro-4-methoxy-7,7-dimethyl-9-(oxazol-5-yl)-6H-chromeno[4,3-b]quinoline;

(6aS,12aS)-2-bromo-6a,7,12,12a-tetrahydro-4-methoxy-7,7-dimethyl-9-(oxazol-5-yl)-6H-chromeno[4,3-b]quinoline;

(6aR,12aS)-methyl 2-bromo-6a,7,12,12a-tetrahydro-4-methoxy-7,7-dimethyl-6H-chromeno[4,3-b]quinoline-9-carboxylate;

(6aS,12aS)-methyl 2-bromo-6a,7,12,12a-tetrahydro-4-methoxy-7,7-dimethyl-6H-chromeno[4,3-b]quinoline-9-carboxylate;

(6aR,12aS)-2-bromo-6a,7,12,12a-tetrahydro-4-methoxy-7,7-dimethyl-9-(1H-tetrazol-5-yl)-6H-chromeno[4,3-b]quinoline;

diethyl ((6aR, 12aS)-2-bromo-6a,7,12,12a-tetrahydro-4-methoxy-7,7-dimethyl-6H-chromeno[4,3-b]quinolin-9-yl)methylphosphonate;

(6aS,12aS)-2-bromo-6a,7,12,12a-tetrahydro-4-methoxy-7,7-dimethyl-9-(1H-tetrazol-5-yl)-6H-chromeno[4,3-b]quinoline;

diethyl ((6aS,12aS)-2-bromo-6a,7,12,12a-tetrahydro-4-methoxy-7,7-dimethyl-6H-chromeno[4,3-b]quinolin-9-yl)methylphosphonate;

(6aR,12aS)-6a,7,12,12a-tetrahydro-N-(2-hydroxyethyl)-1-methoxy-7,7-dimethyl-6H-chromeno[4,3-b]quinoline-9-carboxamide;

((6aR,12aS)-6a,7,12,12a-tetrahydro-4-methoxy-7,7-dimethyl-6H-chromeno[4,3-b]quinolin-9-yl)(morpholino)methanone;

((6aS,12aS)-6a,7,12,12a-tetrahydro-4-methoxy-7,7-dimethyl-6H-chromeno[4,3-b]quinolin-9-yl)(morpholino)methanone;

((6aR,12aS)-6a,7,12,12a-tetrahydro-1-methoxy-7,7-dimethyl-6H-chromeno[4,3-b]quinolin-9-yl)(1,1-dione-1,4-thiazaperhydroin-yl)methanone;

(6aR,12aS)-6a,7,12,12a-tetrahydro-1-methoxy-N,N,7,7-tetramethyl-6H-chromeno[4,3-b]quinoline-9-carboxamide;

((6aR,12aS)-6a,7,12,12a-tetrahydro-1-methoxy-7,7-dimethyl-6H-chromeno[4,3-b]quinolin-9-yl)(4-tert-butyl-carboxylate-piperazin-1-yl)methanone;

((6aR,12aS)-6a,7,12,12a-tetrahydro-1-fluoro-7,7-dimethyl-6H-chromeno[4,3-b]quinolin-9-yl)(4-tert-butyl-carboxylate-piperazin-1-yl)methanone;

((6aR,12aS)-6a,7,12,12a-tetrahydro-1-methoxy-7,7-dimethyl-6H-chromeno[4,3-b]quinolin-9-yl)(piperazin-1-yl)methanone;

((6aS,12aS)-6a,7,12,12a-tetrahydro-4-methoxy-7,7-dimethyl-6H-chromeno[4,3-b]quinolin-9-yl)(1,1-dione-1,4-thiazaperhydroin-yl)methanone;

((6aR,12aS)-6a,7,12,12a-tetrahydro-4-methoxy-7,7-dimethyl-6H-chromeno[4,3-b]quinolin-9-yl)(1,1-dione-1,4-thiazaperhydroin-yl)methanone;

((6aR,12aS)-6a,7,12,12a-tetrahydro-1-fluoro-7,7-dimethyl-6H-chromeno[4,3-b]quinolin-9-yl)(1,1-dione-1,4-thiazaperhydroin-yl)methanone;

((6aR,12aS)-1-fluoro-6a,7,12,12a-tetrahydro-7,7-dimethyl-6H-chromeno[4,3-b]quinolin-9-yl)(piperazin-1-yl)methanone;

((6aR,12aS)-1-methoxy-6a,7,12,12a-tetrahydro-7,7-dimethyl-6H-chromeno[4,3-b]quinolin-9-yl)(4-ethanesulfonylpiperazin-1-yl)methanone;

((6aS,12aS)-4-methoxy-6a,7,12,12a-tetrahydro-7,7-dimethyl-6H-chromeno[4,3-b]quinolin-9-yl)(4-ethanesulfonylpiperazin-1-yl)methanone;

((6aR,12aS)-4-methoxy-6a,7,12,12a-tetrahydro-7,7-dimethyl-6H-chromeno[4,3-b]quinolin-9-yl)(4-ethanesulfonylpiperazin-1-yl)methanone; and ((6aS,12aS)-4-fluoro-6a,7,12,12a-tetrahydro-7,7-dimethyl-6H-chromeno[4,3-b]quinolin-9-yl)(4-ethanesulfonylpiperazin-1-yl)methanone.

C. Preparation of a Compound of Formula I, varying $R^1$, $R^2$, $R^3$, $R^4$, $R^5$, $R^6$, $R^7$, $R^8$, $R^{20}$, and X Similarly, following the procedure of 3A above, but replacing 5-methoxy-2-(3-methylbut-2-enyloxy)benzaldehyde with other formula (3) compounds or replacing 2-(4-aminophenyl)-1,1,1,3,3,3-hexafluoropropan-2-ol with other compounds of formula (4) or (4b), the following compounds of Formula I are prepared:

2-(2-bromo-7,7-dimethyl(7,12,12a,6a-tetrahydro-6H,12aH,6aH-benzo[e]quinolino[3,2-c]thian-9-yl))-1,1,1,3,3,3-hexafluoropropan-2-ol 2-((6aS,12aR)-2-bromo-7,7-dimethyl(7,12,12a,6a-tetrahydro-6H,12aH,6aH-benzo[e]quinolino[3,2-c]thian-9-yl))-1,1,1,3,3,3-hexafluoropropan-2-ol;

2-((12aS,6aS)-2-bromo-7,7-dimethyl(7,12,12a,6a-tetrahydro-6H,12aH,6aH-benzo[e]quinolino[3,2-c]thian-9-yl))-1,1,1,3,3,3-hexafluoropropan-2-ol;

2-bromo-7,7-dimethyl-7,12,12a,6a-tetrahydro-6H,12aH,6aH-benzo[e]quinolino[3,2-c]thiane-9-carboxamide:

1,1,1,3,3,3-hexafluoro-2-(2-methoxy-7,7-dimethyl(7,12,12a,6a-tetrahydro-6H,12aH,6aH-benzo[e]quinolino[3,2-c]thian-9-yl))propan-2-ol;

1,1,1,3,3,3-hexafluoro-2-(4-methoxy-7,7-dimethyl(7,12,12a,6a-tetrahydro-6H,12aH,6aH-benzo[e]quinolino[3,2-c]thian-9-yl))propan-2-ol;

2-[7,7-dimethyl-2-(trifluoromethoxy)( 7,12,12a,6a-tetrahydro-6H,12aH,6aH-benzo[e]quinolino[3,2-c]thian-9-yl)]-1,1,1,3,3,3-hexafluoropropan-2-ol;

2-[(12aS,6aS)-7,7-dimethyl-2-(trifluoromethoxy)( 7,12,12a,6a-tetrahydro-6H,12aH,6aH-benzo[e]quinolino[3,2-c]thian-9-yl)]-1,1,1,3,3,3-hexafluoropropan-2-ol;

3-methylbut-2-enyl 7,7-dimethyl-9-[2,2,2-trifluoro-1-hydroxy-1-(trifluoromethyl)ethyl] -7,12,12a,6a-tetrahydro-6H,12aH,6aH-benzo[e]quinolino[3,2-c]thiane-3-carboxylate 3-methylbut-2-enyl 7,7-dimethyl-9-[2,2,2-trifluoro-1-hydroxy-1-(trifluoromethyl)ethyl]-7,12,12a,6a-tetrahydro-6H,12aH,6aH-benzo[3,4-e]quinolino[3,2-c]thiane-2-carboxylate 7,7-dimethyl-9-[2,2,2-trifluoro-1-hydroxy-1-(trifluoromethyl)ethyl]-7,12,12a,6a-tetrahydro-6H,12aH,6aH-benzo[e]quinolino[3,2-c]thiane-3-carboxylic acid 1,1,1,3,3,3-hexafluoro-2-(4,7,7-trimethyl(7,12,12a,6a-tetrahydro-6H,12aH,6aH-benzo[e]quinolino[3,2-c]thian-9-yl))propan-2-ol;

4-methoxy-7,7-dimethyl-9-(1,2,3,4-tetraazol-5-yl)-7,12,12a,6a-tetrahydro-6H,12aH,6aH-benzo[e]quinolino[3,2-c]thiane 4-((6aS,12aR)-4-methoxy-7,7-dimethyl-7,12,12a,6a-tetrahydro-6H,12aH,6aH-benzo[e]quinolino[3,2-c]thian-9-yl)-1,4-thiazaperhydroine-1,1-dione;

4-(4-methoxy-7,7-dimethyl-7,12,12a,6a-tetrahydro-6H,12aH,6aH-benzo[e]quinolino[3,2-c]thian-9-yl)-1,4-thiazaperhydroine-1,1-dione;

2-(4-ethoxy-7,7-dimethyl(7,12,12a,6a-tetrahydro-6H,12aH,6aH-benzo[e]quinolino[3,2-c]thian-9-yl))-1,1,1,3,3,3-hexafluoropropan-2-ol;

4-methoxy-7,7-dimethyl-7,12,12a,6a-tetrahydro-6H,12aH,6aH-benzo[e]quinolino[3,2-c]thiane-9-carboxamide 1,1,1,3,3,3-hexafluoro-2-(1-methoxy-7,7-dimethyl(7,12,12a,6a-tetrahydro-6H,12aH,6aH-benzo[e]quinolino[3,2-c]thian-9-yl))propan-2-ol;

2-[7,7-dimethyl-4-(3-methylbut-2-enyloxy)( 7,12,12a,6a-tetrahydro-6H,12aH,6aH-benzo[e]quinolino[3,2-c]thian-9-yl)]-1,1,1,3,3,3-hexafluoropropan-2-ol;

2-(4-methoxy-7,7-dimethyl-7,12,12a,6a-tetrahydro-6H,12aH,6aH-benzo[e]quinolino[3,2-c]thian-9-yl)acetic acid;

4,7,7-trimethyl-7,12,12a,6a-tetrahydro-6H,12aH,6aH-benzo[e]quinolino[3,2-c]thiane-9-carboxamide;

4-ethoxy-7,7-dimethyl-7,12,12a,6a-tetrahydro-6H,12aH,6aH-benzo[e]quinolino[3,2-c]thiane-9-carboxamide;

4,7,7-trimethyl-7,12,12a,6a-tetrahydrochromano[4,3-b]quinoline;

4,7,7-trimethyl-7,12,12a,6a-tetrahydro-6H-benzo[e]quinolino[3,2-c]thiane (12aS)-4,7,7-trimethyl-7,12,12a,6a-tetrahydro-6H-benzo[e]quinolino[3,2-c]thiane 1,1,1,3,3,3 -hexafluoro-2-(4-methoxy-7,7-dimethyl(7,12,12a,6a-tetrahydro-6H,12aH,6aH-benzo[e]quinolino[3,2-c]thian-9-yl))propan-2-ol;

2-((6aR)-4-methoxy-7,7-dimethyl(7,12,12a,6a-tetrahydro-6H,12aH,6aH-benzo[e]quinolino[3,2-c]thian-9-yl))-1,1,1,3,3,3-hexafluoropropan-2-ol;

(6aS,12aR)-4-methoxy-7,7-dimethyl-7,12,12a,6a-tetrahydro-6H-benzo[e]quinolino[3,2-c]thiane;

(12aS,6aS)-4-methoxy-7,7-dimethyl-7,12,12a,6a-tetrahydro-6H-benzo[e]quinolino[3,2-c]thiane;

4-ethoxy-7,7-dimethyl-9-(trifluoromethyl)-7,12,12a,6a-tetrahydro-6H-benzo[e]quinolino[3,2-c]thiane;

1-(4-ethoxy-7,7-dimethyl-7,12,12a,6a-tetrahydro-6H,12aH,6aH-benzo[e]quinolino[3,2-c]thian-9-yl)ethan-1-one;

1-(1-methoxy-7,7-dimethyl-7,12,12a,6a-tetrahydro-6H,12aH,6aH-benzo[e]quinolino[3,2-c]thian-9-yl)ethan-1-one;

1-methoxy-7,7-dimethyl-9-(trifluoromethy;l)-7,12,12a,6a-tetrahydro-6H-benzo[e]quinolino[3,2-c]thiane;

1-methoxy-7,7-dimethyl-7,12,12a,6a-tetrahydro-6H-benzo[e]quinolino[3,2-c]thiane-9-carboxamide (6aS,12aR)-4-methoxy-7,7-dimethyl-9-(methylethyl)-7,12,12a,6a-tetrahydro-6H-benzo[e]quinolino[3,2-c]thiane;

(12aS,6aS)-4-methoxy-7,7-dimethyl-9-(methylethyl)-7,12,12a,6a-tetrahydro-6H-benzo[e]quinolino[3,2-c]thiane;

(6aS,12aR)-9-fluoro-4-methoxy-7,7-dimethyl-7,12,12a,6a-tetrahydro-6H-benzo[e]quinolino[3,2-c]thiane;

4-fluoro-7,7-dimethyl-7,12,12a,6a-tetrahydro-6H,12aH,6aH-benzo[e]quinolino[3,2-c]thiane-9-carboxamide 1,1,1,3,3,3 -hexafluoro-2-(4-fluoro-7,7-dimethyl(7,12,12a,6a-tetrahydro-6H,12aH,6aH-benzo[e]quinolino[3,2-c]thian-9-yl))propan-2-ol;

4-methoxy-7,7-dimethyl-9-(methylethoxy)-7,12-dihydro-6H-benzo[e]quinolino[3,2-c]thiin 9-ethoxy-4-methoxy-7,7-dimethyl-7,12-dihydro-6H-benzo[e]quinolino[3,2-c]thiin ((6aS,12aR)-4-methoxy-7,7-dimethyl(7,12,12a,6a-tetrahydro-6H,12aH,6aH-benzo[e]quinolino[3,2-c]thian-9-yloxy))trifluoromethane;

(12aS,6aR)-1-methoxy-7,7-dimethyl-7,12,12a,6a-tetrahydro-6H-benzo[e]quinolino[3,2-c]thiane;

(12aS,6aR)-1-methoxy-7,7-dimethyl-9-(methylethyl)-7,12,12a,6a-tetrahydro-6H-benzo[e]quinolino[3,2-c]thiane;

(12aS,6aR)-9-fluoro-1-methoxy-7,7-dimethyl-7,12,12a,6a-tetrahydro-6H-benzo[e]quinolino[3,2-c]thiane;

(12aS,6aR)-9-ethoxy-1-methoxy-7,7-dimethyl-7,12,12a,6a-tetrahydro-6H-benzo[e]quinolino[3,2-c]thiane;

(12aS,6aR)-1-methoxy-7,7-dimethyl-7,12,12a,6a-tetrahydro-6H-benzo[e]quinolino[3,2-c]thiin-9-carboxylic acid 10-(1H-1,2,3,4-tetraazol-5-yl)(12aS,6aR)-1-methoxy-7,7-dimethyl-7,12,12a,6a-tetrahydro-6H-benzo[e]quinolino[3,2-c]thiane;

((12aS,6aR)-1-methoxy-7,7-dimethyl(7,12,12a,6a-tetrahydro-6H,12aH,6aH-benzo[e]quinolino[3,2-c]thian-9-yloxy))trifluoromethane;

amino(4-methoxy-7,7-dimethyl(7,12,12a,6a-tetrahydro-6H,12aH,6aH-benzo[e]quinolino[3,2-c]thian-9-yl))methane-1-thione;

{[(4-methoxy-7,7-dimethyl(7,12,12a,6a-tetrahydro-6H,12aH,6aH-benzo[e]quinolino[3,2-c]thian-9-yl))methyl]sulfonyl}methylamine;

methylethyl 3-(4-methoxy-7,7-dimethyl-7,12,12a,6a-tetrahydro-6H,12aH,6aH-benzo[e]quinolino[3,2-c]thian-9-yl)benzoate;

(12aS,6aR)-1-methoxy-7,7-dimethyl-9-(1,3-oxazol-5-yl)-7,12,12a,6a-tetrahydro-6H-benzo[e]quinolino[3,2-c]thiane;

(12aS,6aR)-1-methoxy-7,7-dimethyl-7,12,12a,6a-tetrahydro-6H-benzo[e]quinolino[3,2-c]thiin-10-carbonitrile 2-((6aS,12aR)-1-bromo-4-methoxy-7,7-dimethyl(7,12,12a,6a-tetrahydro-6H,12aH,6aH-benzo[e]quinolino[3,2-c]thian-9-yl))-1,1,1,3,3,3-hexafluoropropan-2-ol;

2-((6aS,12aR)-2-bromo-4-methoxy-7,7-dimethyl(7,12,12a,6a-tetrahydro-6H,12aH,6aH-benzo[e]quinolino[3,2-c]thian-9-yl))-1,1,1,3,3,3-hexafluoropropan-2-ol;

2-((12aR,6aR)-2-bromo-4-methoxy-7,7-dimethyl(7,12,12a,6a-tetrahydro-6H,12aH,6aH-benzo[e]quinolino[3,2-c]thian-9-yl))-1,1,1,3,3,3-hexafluoropropan-2-ol;

2-(2,4-difluoro-7,7-dimethyl(7,12,12a,6a-tetrahydro-6H,12aH,6aH-benzo[e]quinolino[3,2-c]thian-9-yl))-1,1,1,3,3,3-hexafluoropropan-2-ol;

2-(2,4-dichloro-7,7-dimethyl(7,12,12a,6a-tetrahydro-6H,12aH,6aH-benzo[e]quinolino[3,2-c]thian-9-yl))-1,1,1,3,3,3-hexafluoropropan-2-ol;

2-(2-chloro-4,7,7-trimethyl(7,12,12a,6a-tetrahydro-6H,12aH,6aH-benzo[e]quinolino[3,2-c]thian-9-yl))-1,1,1,3,3,3-hexafluoropropan-2-ol;

2-((6aS,12aR)-7,7-dimethyl(7,12,12a,6a-tetrahydro-6H,12aH,6aH-benzo[e]quinolino[3,2-c]thian-9-yl))-1,1,1,3,3,3-hexafluoropropan-2-ol;

(12aS,6aR)-1-methoxy-7,7-dimethyl-9-(1,2,3,4-tetraazol-5-yl)-7,12,12a,6a-tetrahydro-6H-benzo[e]quinolino[3,2-c]thiane;

4-((12aS,6aR)-1-methoxy-7,7-dimethyl-7,12,12a,6a-tetrahydro-6H,12aH,6aH-benzo[e]quinolino[3,2-c]thian-9-yl)-1,4-thiazaperhydroine-1,1-dione;

4-methoxy-7,7-dimethyl-9-(1,2,3,4-tetraazol-5-ylmethyl)-7,12,12a,6a-tetrahydro-6H-benzo[e]quinolino[3,2-c]thiane;

(12aS,6aR)-1-methoxy-7,7-dimethyl-9-(1,2,3-thiadiazol-4-yl)-7,12,12a,6a-tetrahydro-6H-benzo[e]quinolino[3,2-c]thiane; and 1-methoxy-7,7-dimethyl-9-(4-methyl(1,2,4-triazol-3-yl))-7,12,12a,6a-tetrahydro-6H-benzo[e]quinolino[3,2-c]thiane.

D. Preparation of a Compound of Formula I, varying A, D, $R^1$, $R^2$, $R^3$, $R^4$, $R^5$, $R^6$, $R^7$, $R^8$, $R^{20}$, and X Similarly, following the procedure of 3A above, but replacing 5-methoxy-2-(3-methylbut-2-enyloxy)benzaldehyde with other formula (3) compounds or replacing 2-(4-aminophenyl)-1,1,1,3,3,3-hexafluoropropan-2-ol with other compounds of formula (4) or (4b), other compounds of Formula I are prepared.

EXAMPLE 4

Preparation of a Compound of Formula I

A. Preparation of a Compound of Formula I in which A and D are Phenyl, $R^1$ and $R^2$ are Methyl, $R^3$ is 2-Methoxy, $R^4$, $R^5$, $R^6$, $R^7$ and $R^8$ are Hydrogen, $R^{20}$ is —C(O)NH(CH$_2$)$_2$OH, and X is Oxygen

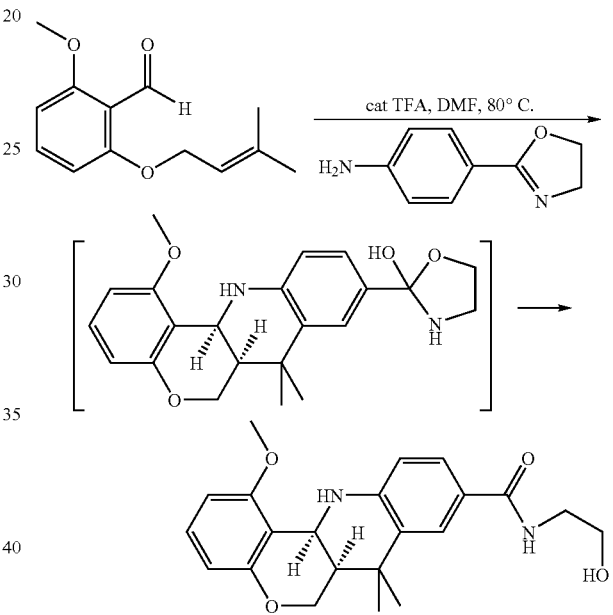

As shown above, to a solution of 6-methoxy-2-(3-methylbut-2-enyloxy)benzaldehyde (220 mg, 1.0 mmol) and 4-(1,3-oxazolin-2-yl)phenylamine (162 mg, 1.0 mmol) in anhydrous DMF (10 ml) was added trifluoroacetic acid (57 mg, 0.5 mmol). The reaction mixture was stirred at 80° C. for about 2 hours when it was substantially done. After cooling, this reaction mixture was taken up with ethyl acetate (30 ml) and decanted into a separatory funnel. The organic phase was washed sequentially with water (30 ml), saturated ammonium chloride (30 ml), brine, and dried over Na$_2$SO4. The solution was concentrated in vacuo on a rotovap. The crude mixture was then purified by reverse phase HPLC using a gradient eluent (2.5 to 97.5% acetonitrile in water) to provide the desired material ((12aS,6aR)-1-methoxy-7,7-dimethyl(7,12,12a,6a-tetrahydrochromano[4,3-b]quinolin-9-yl))-N-(2-hydroxyethyl)carboxamide as white solid.

$^1$H NMR (400 MHz, CDCl$_3$) δ 7.70 (d, 1 H, J=1.75 Hz); 7.40 (dd, 1 H, J=9.20, 2.10 Hz); 7.21 (t, 1 H, J=8.22 Hz); 6.55 (m, 2 H); 6.48 (m, 1 H); 6.38 (d, 1 H, J=8.61 Hz ); 4.89 (d, 1 H, J=3.52 Hz); 4.69 (s, 1 H); 4.24 (ddd, 1 H, J=10.55, 3.52, 1.17 Hz); 3.95 (s, 3 H); 3.85 (m, 2 H); 3.63 (m, 2 H); 3.57 (dd, 1 H, J=12.13, 10.96 Hz,); 1.99 (m, 1 H); 1.39-1.56 (s, 6 H). MS mz (M+H): 383.06.

B. Preparation of a Compound of Formula I, varying $R^{20}$

Similarly, following the procedure of 4A above, but replacing 6-methoxy-2-(3-methylbut-2-enyloxy)benzaldehyde with other formula (3) compounds or replacing 4-(1,3-oxazolin-2-yl)phenylamine with other compounds of formula (4) or (4b), other compounds of Formula I are prepared.

EXAMPLE 5

Preparation of a Compound of Formula I

A. Preparation of a Compound of Formula I in which A and D are Phenyl, $R^1$, $R^2$, and $R^6$ are Methyl, $R^3$ is 2-Methoxy, $R^4$, $R^5$, $R^7$ and $R^8$ are Hydrogen, $R^{20}$ is —C(O)OCH$_3$, and X is Oxygen

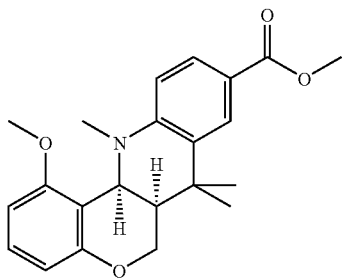

To a solution of compound 6-methoxy-2-(3-methylbut-2-enyloxy)benzaldehyde (220 mg, 1.0 mmol) and methyl 4-(methylamino)benzoate (165 mg, 1.0 mmol) in anhydrous DMF (10 ml) was added trifluoroacetic acid (57 mg, 0.5 mmol). The reaction mixture was stirred at 90° C. for about 24 hours when it was substantially done. After cooling, this reaction mixture was taken up with ethyl acetate (30 ml) and decanted into a separatory funnel. The organic phase was washed sequentially with water (30 ml), saturated aqueous sodium bicarbonate (30 ml), ammonium chloride (30 ml), brine, and dried over Na$_2$SO4. The solution was concentrated in vacuo on a rotovap. The resulting yellow gel was then purified by chromatography via silica gel using 8:2 hexanes: ethyl acetate eluent to provide 320 mg (87%) of the desired diastereomers methyl (12aS,6aR)-1-methoxy-7,7,12-trimethyl-7,12,12a,6a-tetrahydrochromano[4,3-b]quinoline-9-carboxylate and methyl (12aS,6aS)-1-methoxy-7,7,12-trimethyl-7,12,12a,6a-tetrahydrochromano[4,3-b]quinoline-9-carboxylate as pale yellow solid (5.5/1 cis/trans). Reverse phase HPLC using a gradient eluent (2.5 to 97.5% acetonitrile in water) provided the desired product methyl (12aS,6aR)-1-methoxy-7,7,12-trimethyl-7,12,12a,6a-tetrahydrochromano[4,3-b]quinoline-9-carboxylate as off-white solid.

$^1$H NMR (400 MHz, CDCl$_3$) δ 7.90 (d, 1 H, J=1.96 Hz); 7.82 (dd, 1 H, J=8.61, 1.96 Hz); 7.25 (t, 1 H, J=8.22 Hz); 6.64 (d, 1 H, J=9.00 Hz); 6.54 (m, 2 H); 4.95 (s, 1 H); 4.30 (dd, 1 H, J=10.56, 3.13 Hz); 3.91 (s, 3 H); 3.87 (m, 1 H); 2.84 (s, 1 H); 2.00 (m, 1 H); 1.41-1.50 (s, 6 H). MS mz (M+H): 367.96.

B. Preparation of a Compound of Formula I, varying $R^1$, $R^2$, $R^3$, $R^4$, $R^5$, $R^6$, $R^7$, $R^8$, $R^{20}$, and X Similarly, following the procedure of 5A above, but replacing 5-methoxy-2-(3-methylbut-2-enyloxy)benzaldehyde with other formula (3) compounds or replacing methyl 4-(methylamino)benzoate with other compounds of formula (4) or (4b), the following compounds of Formula I were prepared:

2-((6aR,12aS)-6a,7-dihydro-1-methoxy-7,7-dimethyl-6H-chromeno[4,3-b]quinolin-12(12aH)-yl)acetic acid;
2-((6aS,12aS)-6a,7-dihydro-1-methoxy-7,7-dimethyl-6H-chromeno[4,3-b]quinolin-12(12aH)-yl)acetic acid;
ethyl 2-((6aS,12aS)-6a,7-dihydro-1-methoxy-7,7-dimethyl-6H-chromeno[4,3-b]quinolin-12(12aH)-yl)acetate;
ethyl 2-((6aR,12aS)-6a,7-dihydro-1-methoxy-7,7-dimethyl-6H-chromeno[4,3-b]quinolin-12(12aH)-yl)acetate;
(6aS,12aS)-12-benzyl-6a,7,12,12a-tetrahydro-1,9-dimethoxy-7,7-dimethyl-6H-chromeno[4,3-b]quinoline;
(6aR,12aS)-12-benzyl-6a,7,12,12a-tetrahydro-1,9-dimethoxy-7,7-dimethyl-6H-chromeno[4,3-b]quinoline;
(6aR,12aS)-12-ethyl-6a,7,12,12a-tetrahydro-1-methoxy-7,7-dimethyl-6H-chromeno[4,3-b]quinoline;
(6aS,12aS)-12-ethyl-6a,7,12,12a-tetrahydro-1-methoxy-7,7-dimethyl-6H-chromeno[4,3-b]quinoline;
methyl 3-((6aS,12aR)-6a,7-dihydro-1-methoxy-7,7-dimethyl-6H-chromeno[4,3-b]quinolin-12(12aH)-yl)propanoate;
methyl 3-((6aR,12aR)-6a,7-dihydro-1-methoxy-7,7-dimethyl-6H-chromeno[4,3-b]quinolin-12(12aH)-yl)propanoate;
(6aR,12aS)-12-propyl-6a,7,12,12a-tetrahydro-1-methoxy-7,7-dimethyl-6H-chromeno[4,3-b]quinoline;
(6aS,12aS)-12-propyl-6a,7,12,12a-tetrahydro-1-methoxy-7,7-dimethyl-6H-chromeno[4,3-b]quinoline;
(6aR,12aS)-12-butyl-6a,7,12,12a-tetrahydro-1-methoxy-7,7-dimethyl-6H-chromeno[4,3-b]quinoline;
(6aS,12aS)-12-butyl-6a,7,12,12a-tetrahydro-1-methoxy-7,7-dimethyl-6H-chromeno[4,3-b]quinoline;
(6aS,12aS)-6a,7,12,12a-tetrahydro-1,9-dimethoxy-7,7,12-trimethyl-6H-chromeno[4,3-b]quinoline; and
(6aS,12aS)-3-(benzyloxy)-6a,7,12,12a-tetrahydro-9-methoxy-7,7,12-trimethyl-6H-chromeno[4,3-b]quinoline.

C. Preparation of a Compound of Formula I, varying A, D, $R^1$, $R^2$, $R^3$, $R^4$, $R^5$, $R^6$, $R^7$, $R^8$, $R^{20}$, and X Similarly, following the procedure of 5A above, but replacing 5-methoxy-2-(3-methylbut-2-enyloxy)benzaldehyde with other formula (3) compounds or replacing methyl 4-(methylamino)benzoate with other compounds of formula (4), other compounds of Formula I are prepared.

EXAMPLE 6

Preparation of a Compound of Formula I

A. Preparation of a Compound of Formula I in which A and D are Phenyl, $R^1$ and $R^2$ are Methyl, $R^6$ is Cyclohexyl, $R^3$ is 2-Methoxy, $R^4$, $R^5$, $R^7$, $R^8$, and $R^{20}$ are Hydrogen, and X is Oxygen

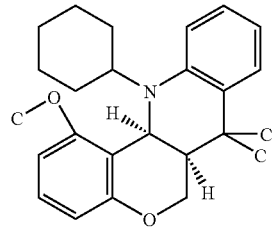

As shown above, to a 3 ml Biotage reaction vial equipped with a stir bar was placed 6-methoxy-2-(3-methylbut-2-enyloxy)benzaldehyde (220 mg, 1.0 mmol), cyclohexylphenylamine (167 mg, 0.95 mmol) in anhydrous DMF (2 ml) and trifluoroacetic acid (57 mg, 0.5 mmol). The reaction vial was capped, subjected to Personal Chemistry microwave irradiation at 180° C. for 30 minutes. After cooling, this reaction mixture was taken up with ethyl acetate (30 ml) and decanted into a separatory funnel. The organic phase was washed sequentially with water (30 ml), saturated aqueous sodium bicarbonate (30 ml), ammonium chloride (30 ml), brine, and dried over $Na_2SO_4$. The solution was concentrated in vacuo on a rotovap. The resulting yellow gel was then purified by chromatography via silica gel using dichloromethane eluent to provide the desired cis-isomer (12aS,6aR)-12-cyclohexyl-1-methoxy-7,7-dimethyl-7,12,12a,6a-tetrahydrochromano[4,3-b]quinoline and trans-isomer.

$^1$H NMR for cis-isomer (12aS,6aR)-12-cyclohexyl-1-methoxy-7,7-dimethyl-7,12,12a,6a-tetrahydrochromano[4,3-b]quinoline (400 MHz, $CDCl_3$) δ 7.15-7.20 (m, 2 H); 7.08 (m, 1 H); 6.63 (m, 2 H); 6.49 (d, 1 H, J=8.2Hz); 6.45 (dd, 1 H, J=8.2, 0.88 Hz); 4.95 (d, 1 H, J=1.1 Hz); 4.24 (m, 1 H); 3.97 (dd, 1 H, J=12.5, 10.6 Hz); 3.86 (s, 3 H); 3.25 (m, 1 H); 2.98 (m, 1 H); 1.91 (m, 1 H); 1.50-1.60 (m, 5 H); 1.36-1.38 (m, 7 H); 0.70 (t, 3 H, J=7.4 Hz). MS mz (M+H): 377.9.

B. Preparation of a Compound of Formula I, varying $R^1$, $R^2$, $R^3$, $R^4$, $R^5$, $R^6$, $R^7$, $R^8$, $R^{20}$, and X Similarly, following the procedure of 6A above, but replacing 6-methoxy-2-(3-methylbut-2-enyloxy)benzaldehyde with other formula (3) compounds or replacing cyclohexylphenylamine with other compounds of formula (4), the following compounds of Formula I were prepared:

(6aR,12aS)-6a,7,12,12a-tetrahydro-12-isopropyl-1-methoxy-7,7-dimethyl-6H-chromeno[4,3-b]quinoline; and
(6aS,12aS)-12-cyclohexyl-6a,7,12,12a-tetrahydro-1-methoxy-7,7-dimethyl-6H-chromeno[4,3-b]quinoline.

C. Preparation of a Compound of Formula I, varying A, D, $R^1$, $R^2$, $R^3$, $R^4$, $R^5$, $R^6$, $R^7$, $R^8$, $R^{20}$, and X Similarly, following the procedure of 6A above, but replacing 6-methoxy-2-(3-methylbut-2-enyloxy)benzaldehyde with other formula (3) compounds or replacing cyclohexylphenylamine with other compounds of formula (4), other compounds of Formula I are prepared.

EXAMPLE 7

Preparation of a Compound of Formula I

A. Preparation of a Compound of Formula I in which $R^1$ and $R^2$ are Methyl, $R^3$ is 5-Methoxy, $R^4$, $R^5$, $R^6$, $R^7$ and $R^8$ are Hydrogen, $R^{20}$ is 1,1,1,3,3,3-Hexafluoromethanol, and X is Oxygen To a 5 ml Biotage vial equipped with a stir bar was added (12aS,6aR)-9-bromo-4-methoxy-7,7-dimethyl-7,12,12a,6a-tetrahydrochromano[4,3-b]quinoline (37 mg, 0.1 mmol), 4-fluorophenyl-boronic acid (17 mg, 0.12 mmol), 125 μl of 2N aqueous sodium carbonate solution, and acetonitrile/water (1.5 ml/1 ml). The mixture was stirred at room temperature for 2 minutes under nitrogen, then dichloro bis(triphenylphosphine)palladium (II) (3.5 mg, 0.005 mmol) was added, and the vial sealed. The vial was subjected to irradiation in a chemistry microwave (Emrys Optimizer) for 15 minutes at a temperature of 150° C., then cooled, filtered through celite, and washed with ethyl acetate (50 ml). The filtrate was washed with 0.5N aqueous sodium hydroxide (30 ml), followed by saturated ammonium chloride, then brine, and dried over sodium sulfate. After removal of the solvent under reduced pressure the residue was dissolved in acetone (50 ml) then subjected to preparative thin layer chromatography, eluting with ethyl acetate/hexanes (9:1). Evaporation of the solvent provided (12aS,6aR)-9-(4-fluorophenyl)-4-methoxy-7,7-dimethyl-7,12,12a,6a-tetrahydrochromano[4,3-b]quinoline. MS 390.06 (M+H).

B. Preparation of a Compound of Formula I, varing $R^1$, $R^2$, $R^3$, $R^4$, $R^5$, $R^6$, $R^7$, $R^8$, $R^{20}$, and X Similarly, following the procedure of 7A above, but replacing (12aS,6aR)-9-bromo-4-methoxy-7,7-dimethyl-7,12,12a,6a-tetrahydrochromano[4,3-b]quinoline with other Formula I compounds or replacing 4-fluorophenyl-boronic acid with other boronic acid derivates, the following compounds of Formula I were prepared:

4-((12aS,6aS)-1-methoxy-7,7-dimethyl-7,12,12a,6a-tetrahydrochromano[4,3 -b]quinolin-9-yl)benzenecarbonitrile;
(12aS,6aS)-1-methoxy-7,7-dimethyl-9-[4-(trifluoromethyl)phenyl]-7,12,12a,6a-tetrahydrochromano[4,3-b]quinoline;
(12aS,6aS)-1-methoxy-7,7-dimethyl-9-phenyl-7,12,12a,6a-tetrahydrochromano[4,3-b]quinoline;
(12aS,6aR)-9-ethynyl-1-methoxy-7,7-dimethyl-7,12,12a,6a-tetrahydrochromano[4,3-b]quinoline;
ethyl 4-((12aS,6aS)-1-methoxy-7,7-dimethyl-7,12,12a,6a-tetrahydrochromano[4,3-b]quinolin-9-yl)benzoate;
4-((12aS,6aS)-1-methoxy-7,7-dimethyl-7,12,12a,6a-tetrahydrochromano[4,3-b]quinolin-9-yl)benzenesulfonamide;
[4-((12aS,6aS)-1-methoxy-7,7-dimethyl-7,12,12a,6a-tetrahydrochromano[4,3-b]quinolin-9-yl)phenyl]methan-1-ol;
4-((12aS,6aR)-1-methoxy-7,7-dimethyl-7,12,12a,6a-tetrahydrochromano[4,3-b]quinolin-9-yl)benzoic acid;
ethyl 4-((12aS,6aR)-1-methoxy-7,7-dimethyl-7,12,12a,6a-tetrahydrochromano[4,3-b]quinolin-9-yl)benzoate;
4-((12aS,6aR)-1-methoxy-7,7-dimethyl-7,12,12a,6a-tetrahydrochromano[4,3-b]quinolin-9-yl)benzamide;
(12aS,6aR)-9-(4-fluorophenyl)-1-methoxy-7,7-dimethyl-7,12,12a,6a-tetrahydrochromano[4,3-b]quinoline;
1-((12aS,6aR)-1-methoxy-7,7-dimethyl(7,12,12a,6a-tetrahydrochromano[4,3-b]quinolin-9-yl))-4-methoxybenzene;
methyl 3-((12aS,6aR)-1-methoxy-7,7-dimethyl-7,12,12a,6a-tetrahydrochromano[4,3-b]quinolin-9-yl)benzoate;
3-[4-((12aS,6aR)-1-methoxy-7,7-dimethyl-7,12,12a,6a-tetrahydrochromano[4,3-b]quinolin-9-yl)phenyl]propanoic acid; and
(2E)-3-[4-((12aS,6aR)-1-methoxy-7,7-dimethyl(7,12,12a,6a-tetrahydrochromano[4,3-b]quinolin-9-yl))phenyl]prop-2-enoic acid.

C. Preparation of a Compound of Formula I, varying $R^1$, $R^2$, $R^3$, $R^4$, $R^5$, $R^6$, $R^7$, $R^8$, $R^{20}$, and X Similarly, following the procedure of 7A above, but replacing (12aS,6aR)-9-bromo-4-methoxy-7,7-dimethyl-7,12,12a,6a-tetrahydrochromano[4,3-b]quinoline with other Formula

EXAMPLE 8

Preparation of a Compound of Formula I

A. Preparation of a Compound of Formula I in which $R^1$ and $R^2$ are Methyl, $R^3$ is 5-Methoxy, $R^4$, $R^5$, $R^6$, $R^7$ and $R^8$ are Hydrogen $R^{20}$ is 1,1,1,3,3,3-Hexafluoromethanol, and X is Oxygen

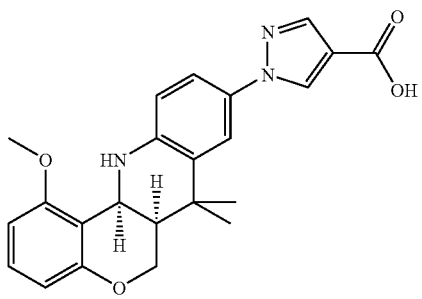

2.68 g of ethyl 1-((12aS,6aR)-1-methoxy-7,7-dimethyl-7,12,12a,6a-tetrahydrochromano[4,3-b]quinolin-9-yl)pyrazole-4-carboxylate, prepared as described in Example 3, was in a solution of 30 mL THF, 30 mL of methanol, 30 mL of $H_2O$. To this solution was added 1.3 g of $LiOH.H_2O$. The reaction was stirred at room temperature over the weekend. The solvent was then removed and solution titrated so provide a solid that was collected by filtration and washed to give the product, 1-((12aS,6aR)-1-methoxy-7,7-dimethyl-7,12,12a,6a-tetrahydrochromano[4,3-b]quinolin-9-yl)pyrazole-4-carboxylic acid.

B. Preparation of a Compound of Formula I in which $R^1$ and $R^2$ are Methyl, $R^3$ is 5-Methoxy, $R^4$, $R^5$, $R^6$, $R^7$ and $R^8$ are Hydrogen, $R^{20}$ is 1,1,1,3,3,3-Hexafluoromethanol, and X is Oxygen Similarly, following the procedure of 8A above, but replacing ethyl 1-((12aS,6aR)-1-methoxy-7,7-dimethyl-7,12,12a,6a-tetrahydrochromano[4,3-b]quinolin-9-yl)pyrazole-4-carboxylate with other Formula I compounds, the following compounds of Formula I were prepared:

- 1-((6aR,12aS)-6a,7,12,12a-tetrahydro-1-methoxy-7,7-dimethyl-6H-chromeno[4,3-b]quinolin-9-yl)-5-methyl-1H-pyrazole-4-carboxylic acid; acid
- 2-((6aR,12aS)-1-fluoro-6a,7, 12,12a-tetrahydro-7,7-dimethyl-6H-chromeno[4,3-b]quinolin-9-yl)oxazole-4-carboxylic acid.

C. Preparation of a Compound of Formula I, varying $R^1$, $R^2$, $R^3$, $R^4$, $R^5$, $R^6$, $R^7$, $R^8$, $R^{20}$, and X Similarly, following the procedure of 8A above, but replacing ethyl 1-((12aS,6aR)-1-methoxy-7,7-dimethyl-7,12,12a,6a-tetrahydrochromano[4,3-b]quinolin-9-yl)pyrazole-4-carboxylate with other Formula I compounds, other compounds of Formula I are prepared.

EXAMPLE 9

Preparation of a Compound of Formula I

A. Preparation of a Compound of Formula I in which $R^1$ and $R^2$ are Methyl, $R^3$ is 5-Methoxy, $R^4$, $R^5$, $R^6$, $R^7$ and $R^8$ are Hydrogen, $R^{20}$ is 1,1,1,3,3,3-Hexafluoromethanol, and X is Oxygen

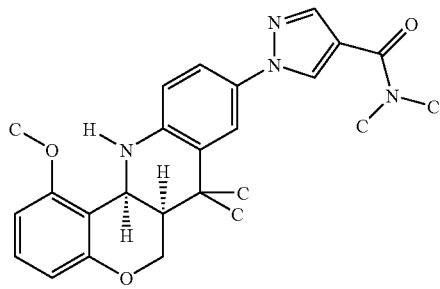

70 mg of the 1-((12aS,6aR)-1-methoxy-7,7-dimethyl-7,12,12a,6a-tetrahydrochromano[4,3-b]quinolin-9-yl)pyrazole-4-carboxylic acid prepared in Example 8A was placed in 5 ml of dichloromethane along with the following:

EDC.HCl 39.7 mg;
1-hydroxybenzotriazole.$H_2O$ 31.7 mg; and
$Me_2NH.HCl$ 16.9 mg.

The reaction mixture was stirred at room temperature overnight and then worked up with 1N HCl, died over $Na_2SO_4$, and then concentrated to yield the product, [1-((12aS,6aR)-1-methoxy-7,7-dimethyl (7,12,12a,6a-tetrahydrochromano [4,3 -b]quinolin-9-yl))pyrazol-4-yl]—N,N-dimethylcarboxamide, as a yellow oil. 1H NMR confirmed the final product was as intended.

B. Preparation of a Compound of Formula I, varying $R^1$, $R^2$, $R^3$, $R^4$, $R^5$, $R^6$, $R^7$, $R^{20}$, and X Similarly, following the procedure of 9A above, but replacing 1-((12aS,6aR)-1-methoxy-7,7-dimethyl-7,12,12a,6a-tetrahydrochromano[4,3-b]quinolin-9-yl)pyrazole-4-carboxylic acid with other Formula I compounds or replacing dimethyl amine with other amine derivates, the following compounds of Formula I were prepared:

- 1-((6aR,12aS)-6a,7,12,12a-tetrahydro-1-methoxy-7,7-dimethyl-6H-chromeno[4,3-b]quinolin-9-yl)1-1H-pyrazole-4-((1,1-dione-1,4-thiazaperhydroin-yl)methanone);
- 1-((6aR,12aS)-6a,7,12,12a-tetrahydro-1-methoxy-7,7-dimethyl-6H-chromeno[4,3-b]quinolin-9-yl)-5-methyl-1H-pyrazole-4-((4-ethanesulfonylpiperazin-1-yl)methanone);
- 1-((6aR,12aS)-6a,7,12,12a-tetrahydro-1-methoxy-7,7-dimethyl-6H-chromeno[4,3-b]quinolin-9-yl)1-5-methyl-1H-pyrazole-4-((1,1-dione-1,4-thiazaperhydroin-yl)methanone);
- 2-((6aR,12aS)-1-fluoro-6a,7,12,12a-tetrahydro-7,7-dimethyl-6H-chromeno[4,3-b]quinolin-9-yl)oxazole-(4-(4-ethanesulfonylpiperazin-1-yl)methanone);
- 2-((6aR,12aS)-1-fluoro-6a,7,12,12a-tetrahydro-7,7-dimethyl-6H-chromeno[4,3-b]quinolin-9-yl)oxazole-(4-(1,1-dione-1,4-thiazaperhydroin-yl)methanone);
- 1-((6aR,12aS)-6a,7,12,12a-tetrahydro-1-fluoro-7,7-dimethyl-6H-chromeno[4,3-b]quinolin-9-yl)-5-methyl-1H-pyrazole-4-((4-ethanesulfonylpiperazin-1-yl)methanone);

1-((6aR,12aS)-6a,7,12,12a-tetrahydro-1-fluoro-7,7-dimethyl-6H-chromeno[4,3-b]quinolin-9-yl)1-5-methyl-1H-pyrazole-4-((1,1-dione-1,4-thiazaperhydroin-yl)methanone);

2-((6aR,12aS)-6a,7,12,12a-tetrahydro-4-methoxy-7,7-dimethyl-6H-chromeno[4,3-b]quinolin-9-yl)oxazole-4-carboxylic acid;

2-((6aR,12aS)-1-methoxy-6a,7,12,12a-tetrahydro-7,7-dimethyl-6H-chromeno[4,3-b]quinolin-9-yl)oxazole-(4-(4-ethanesulfonylpiperazin-1-yl)methanone); and 2-((6aR,12aS)-1-methoxy-6a,7,12,12a-tetrahydro-7,7-dimethyl-6H-chromeno[4,3 -b]quinolin-9-yl)oxazole-(4-(1,1-dione-1,4-thiazaperhydroin-yl)methanone.

C. Preparation of a Compound of Formula I, varying $R^1$, $R^2$, $R^3$, $R^4$, $R^5$, $R^6$, $R^7$, $R^8$, $R^{20}$, and X Similarly, following the procedure of 9A above, but replacing 1-((12aS,6aR)-1-methoxy-7,7-dimethyl-7,12,12a,6a-tetrahydrochromano[4,3-b]quinolin-9-yl)pyrazole-4-carboxylic acid with other Formula I compounds or replacing dimethyl amine with other amine derivates, other compounds of Formula I are prepared.

EXAMPLE 10

Preparation of a Compound of Formula I

A. Preparation of a Compound of Formula I in which A and D are Phenyl, $R^1$ and $R^2$ are Methyl, $R^3$ is 2-Methoxy, $R^4$, $R^5$, $R^6$, $R^7$ and $R^8$ are Hydrogen, $R^{20}$ is 2-Nitrophenyl, and X is Oxygen

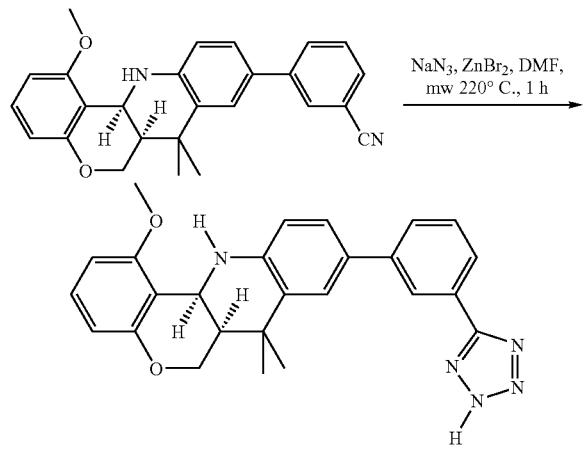

To a 5 ml Biotage microwave reaction vial was placed a stir bar, 3-((12aS,6aR)-1-methoxy-7,7-dimethyl-7,12,12a,6a-tetrahydrochromano[4,3-b]quinolin-9-yl)benzenecarbonitrile (40 mg, 0.1 mmol), sodium azide (20 mg, 0.3 mmol), zinc bromide (46 mg, 0.2 mmol) and DMF (2.0 ml). The reaction mixture was capped and subjected for irradiation at 220° C. for 1 h in a Personal Chemistry microwave. The reaction mixture was cooled to room temperature, and 3 ml water added. It was then filtered through a layer of celite, washed with ethyl acetate (3×10 ml), combined organic phase was washed with saturated aqueous sodium bicarbonate (30 ml), ammonium chloride (30 ml), and brine (30 ml), dried over anhydrous sodium sulfate, concentrated in vacuo to afford pale yellow solid 9-(3-(2H-1,2,3,4-tetraazol-5-yl)phenyl)(12aS,6aR)-1-methoxy-7,7-dimethyl-7,12,12a,6a-tetrahydrochromano[4,3-b]quinoline. MS: m/z (M+H) 439.9.

B. Preparation of a Compound of Formula I, varying $R^1$, $R^2$, $R^3$, $R^4$, $R^5$, $R^6$, $R^7$, $R^8$, $R^{20}$, and X Similarly, following the procedure of 10A above, but replacing 3-((12aS,6aR)-1-methoxy-7,7-dimethyl-7,12,12a,6a-tetrahydrochromano[4,3-b]quinolin-9-yl)benzenecarbonitrile with other Formula I compounds, other compounds of Formula I are prepared.

EXAMPLE 11

Preparation of a Compound of Formula I

A. Preparation of a Compound of Formula I in which A and D are Phenyl, $R^1$ and R2 are Methyl, $R^3$ is 2-Methoxy, $R^4$, $R^5$, $R^6$, $R^7$ and $R^8$ are Hydrogen, $R^{20}$ is 2-Nitrophenyl, and X is Oxygen

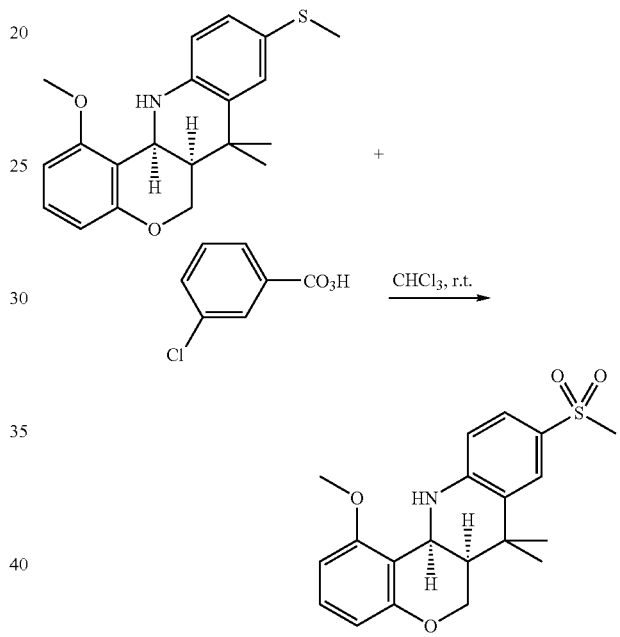

As shown above, to a cooled (0° C.) solution of (12aS,6aR)-1-methoxy-7,7-dimethyl-9-methylthio-7,12,12a,6a-tetrahydrochromano[4,3-b]quinoline (106 mg, 0.31 mmol) in anhydrous chloroform (5 ml) was added 3-chloroperoxybenzoic acid (208 mg, 1.2 mmol). The resulting reaction mixture was stirred at 0° C. for 5 minutes and the ice bath was then removed. After about 30 minutes of stir at room temperature, the reaction was substantially done. The mixture was filtered through a layer of dry sodium sulfate (top) and silica gel (bottom), washed with 50 ml ethyl acetate and decanted into a separatory funnel. The organic phase was washed sequentially with aqueous lithium hydroxide (1N, 5 ml), saturated ammonium chloride (3×10 ml), water, brine, and dried over $Na_2SO4$. The solution was concentrated in vacuo on a rotovap. The mostly pure yellow solid was then purified by chromatography via silica gel using 5% MeOH/$CHCl_3$ eluent to provide (12aS,6aR)-1-methoxy-9-(methylsulfonyl)-7,12,12a,6a-tetrahydrochromano[4,3-b]quinoline as a white solid.

$^1$H NMR (400 MHz, $CDCl_3$) δ 7.63 (d, 1 H, J=1.96 Hz); 7.49 (dd, 1H, J=8.41, 2.35 Hz); 7.19 (t, 1 H, J=8.22 Hz); 6.53 (m, 2H); 6.43 (d, 1H, J=8.61 Hz); 4.86 (m, 1H); 4.73 (m, 1H); 4.22 (ddd, 1H, J=10.76, 3.52, 1.56 Hz); 3.93 (s, 3H); 3.49 (dd, 1H, J=12.13, 10.56Hz); 3.01 (s, 3H); 2.00 (m, 1H); 1.53-1.61 (s, 6H). MS m/z (M+H): 374.1.

B. Preparation of a Compound of Formula I, varying $R^1$, $R^2$, $R^3$, $R^4$, $R^5$, $R^6$, $R^7$, $R^8$, $R^{20}$, and X Similarly, following the procedure of 11A above, the following sulfoxide compounds of Formula I were prepared:

2-((6aR,12aS)-6a,7,12,12a-tetrahydro-1-methoxy-7,7-dimethyl-6H-chromeno[4,3-b]quinolin-9-ylsulfonyl) acetic acid; and (6aR,12aS)-9-(4-fluorophenylsulfonyl)-6a,7,12,12a-tetrahydro-1-methoxy-7,7-dimethyl-6H-chromeno[4,3-b]quinoline.

C. Preparation of a Compound of Formula I, varying A, D, $R^1$, $R^2$, $R^3$, $R^4$, $R^5$, $R^6$, $R^7$, $R^8$, $R^{20}$, and X Similarly, following the procedure of 11A above, other sulfoxide compounds of Formula I are prepared.

EXAMPLE 12

Preparation of a Compound of Formula I

A. Preparation of a Compound of Formula I in which $R^1$ and $R^2$ are Methyl, $R^3$ is 3-Dimethylacrylamide, $R^4$, $R^5$, $R^6$, $R^7$ and $R^8$ are Hydrogen, $R^{20}$ is 1,1,1,3,3,3-Hexafluoromethanol, and X is Oxygen

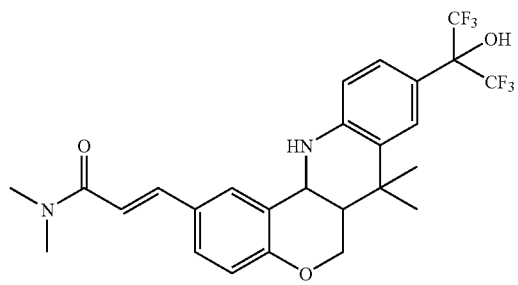

To a solution of 1,1,1,3,3,3-hexafluoro-2-(2-iodo-7,7-dimethyl(7,12,12a,6a-tetrahydrochromano[4,3-b]quinolin-9-yl))propan-2-ol (2.2 g, 3.95 mmol) in dry N,N-dimethylformamide (5 ml) was added tetrabutylammonium chloride (660 mg, 4 mmols), dimethylacrylamide (309 µl), triethylamine (1.4 ml, 10 mmol), followed by palladium diacetate (87 mg, 0.39 mmol). The mixture was heated at 80° C. for 12 hours, cooled, and ethyl acetate was added. The organic layer was washed with 1M aqueous hydrochloric acid, water, saturated sodium bicarbonate, brine, and the organic layer was dried over magnesium sulfate. The solvent was removed under reduced pressure, and the residue was chromatographed on a silica gel column, eluting with ethyl acetate, to yield (2E)-3-{7,7-dimethyl-9-[2,2,2-trifluoro-1-hydroxy-1-(trifluoromethyl)ethyl](7,12,12a,6a-tetrahydrochromano[4,3-b]quinolin-2-yl)}—N,N-dimethylprop-2-enamide. The NMR was satisfactory for the proposed structure.

B. Preparation of a Compound of Formula I, varying $R^1$, $R^2$, $R^3$, $R^4$, $R^5$, $R^6$, $R^7$, $R^8$, $R^{20}$, and X Similarly, following the procedure of 12A above, but replacing 4 dimethylacrylamide with methyl prop-2-enoate, methyl (2E)-3-{7,7-dimethyl-9-[2,2,2-trifluoro-1-hydroxy-1-(trifluoromethyl)ethyl](7, 12,12a,6a-tetrahydrochromano[4,3-b]quinolin-2-yl)}prop-2-enoate was prepared.

C. Preparation of a Compound of Formula I, varying $R^1$, $R^2$, $R^3$, $R^4$, $R^5$, $R^6$, $R^7$, $R^8$, $R^{20}$, and X Similarly, following the procedure of 12A above, but replacing 1,1,1,3,3,3-hexafluoro-2-(2-iodo-7,7-dimethyl(7, 12,12a,6a-tetrahydrochromano[4,3-b]quinolin-9-yl))propan-2-ol with other Formula I compounds or replacing dimethylacrylamide with other compounds having a terminal carbon-carbon double bond, other compounds of Formula I are prepared.

EXAMPLE 13

Preparation of a Compound of Formula I

A. Preparation of a Compound of Formula I in which $R^1$ and $R^2$ are Methyl, $R^3$ is 3-Dimethylpropanamide, $R^4$, $R^5$, $R^6$, $R^7$ and $R^8$ are Hydrogen, $R^{20}$ is 1,1,1,3,3,3-Hexafluoromethanol, and X is Oxygen

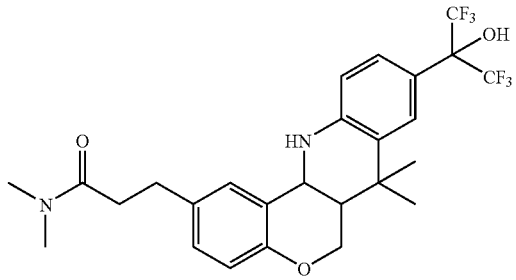

To a solution of (2E)-3-{7,7-dimethyl-9-[2,2,2-trifluoro-1-hydroxy-1-(trifluoromethyl)ethyl](7,12,12a,6a-tetrahydrochromano[4,3-b]quinolin-2-yl)}—N,N-dimethylprop-2-enamide (100 mg, 0.19 mmol) in methanol/water (6 ml of 5/1) at room temperature was added nickel chloride hexahydrate (227 mg, 1.0 mmol), followed by sodium borohydride (18 mg, 0.5 mmol) in portions. The mixture was stirred for 1 hour at room temperature. The solvent was removed under reduced pressure, diluted with ethyl acetate, and washed with saturated aqueous sodium bicarbonate, followed by water, and finally brine. The organic layer was dried over magnesium sulfate, and solvent removed under reduced pressure. The residue was dissolved in ethyl acetate and passed through a portion of silica gel, to provide 3-{7,7-dimethyl-9-[2,2,2-trifluoro-1-hydroxy-1-(trifluoromethyl)ethyl](7,12,12a,6a-tetrahydrochromano[4,3-b]quinolin-2-yl)}—N,N-dimethylpropanamide. NMR satisfactory.

B. Preparation of a Compound of Formula I, varying $R^1$, $R^2$, $R^3$, $R^4$, $R^5$, $R^6$, $R^7$, $R^8$, $R^{20}$, and X Similarly, following the procedure of 13A above, but replacing (2E)-3-{7,7-dimethyl-9-[2,2,2-trifluoro-1-hydroxy-1-(trifluoromethyl)ethyl](7,12,12a,6a-tetrahydrochromano[4,3-b]quinolin-2-yl)}—N,N-dimethylprop-2-enamide with methyl (2E)-3-{7,7-dimethyl-9-[2,2,2-trifluoro-1-hydroxy-1-(trifluoromethyl)ethyl](7,12,12a,6a-tetrahydrochromano[4,3-b]quinolin-2-yl)}prop-2-enoate, methyl 3-{7,7-dimethyl-9-[2,2,2-trifluoro-1-hydroxy-1-(trifluoromethyl)ethyl]-7,12,12a,6a-tetrahydrochromano[4,3-b]quinolin-2-yl}propanoate; was prepared.

C. Preparation of a Compound of Formula I, varying $R^1$, $R^2$, $R^3$, $R^4$, $R^5$, $R^6$, $R^7$, $R^8$, $R^{20}$, and X Similarly, following the procedure of 13A above, but replacing
(2E)-3-{7,7-dimethyl-9-[2,2,2-trifluoro-1-hydroxy-1-(trifluoromethyl)ethyl](7,12,12a,6a-tetrahydrochromano[4,3-b]quinolin-2-yl)}—N,N-dimethylprop-2-enamide
with other Formula I compounds having an unsaturated carbon-carbon double bond, other compounds of Formula I are prepared.

EXAMPLE 14

Preparation of a Compound of Formula I

A. Preparation of a Compound of Formula I in which $R^1$ and $R^2$ are Methyl, $R^4$ is Pyrazol-4-yl, $R^3$ is 5-Methoxy, $R^5$, $R^6$, $R^7$ and $R^8$ are Hydrogen, $R^{20}$ is Oxazol-5-yl, and X is Oxygen

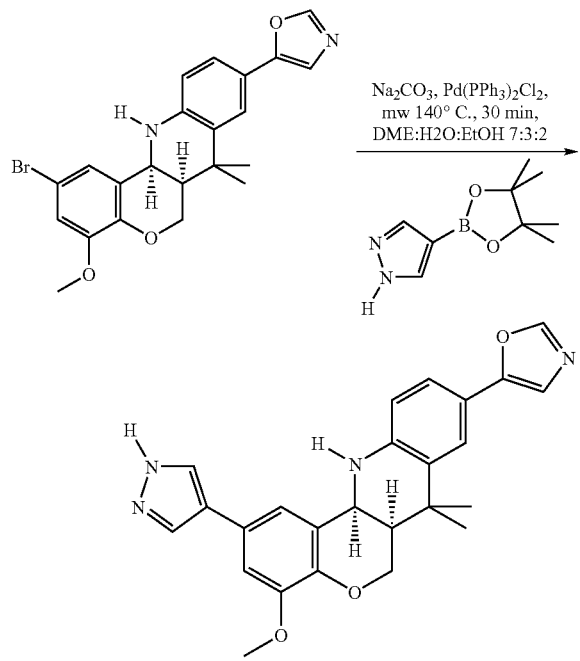

As shown above, to a 3 ml Biotage reaction vial equipped with a stir bar was placed compound (12aS,6aR)-2-bromo-4-methoxy-7,7-dimethyl-9-(1,3-oxazol-5-yl)-7,12,12a,6a-tetrahydrochromano[4,3-b]quinoline (22 mg, 0.05 mmol), 4,4,5,5-tetramethyl-2-pyrazol-4-yl-1,3,2-dioxaborolane (19 mg, 0.1 mmol), 2M aqueous sodium bicarbonate (60 μl, 0.12 mmol), 2 ml mixture of DME/water/ethanol (7:3:2), and dichloro-(triphenylphosphine) palladium(II) (3 mg, 0.04 mmol). The reaction vial was capped, subjected to Personal Chemistry microwave irradiation at 140° C. for 20 minutes. After cooling, this reaction mixture was taken up with ethyl acetate (10 ml), filtered through a layer of celite, washed with ethyl acetate (2×10 ml), and decanted into a separatory funnel. The organic phase was washed sequentially with lithium hydroxide (0.1 N, 20 ml), saturated aqueous ammonium chloride (30 ml), brine, and dried over $Na_2SO_4$. The solution was concentrated in vacuo on a rotovap. The resulting mixture was then purified by chromatography via silica gel using 19:1 dichloromethane:methanol eluent to provide the desired compound, (6aR,12aS)-6a,7,12,12a-tetrahydro-4-methoxy-7,7-dimethyl-9-(oxazol-5-yl)-2-(1H-pyrazol-4-yl)-6H-chromeno[4,3-b]quinoline, as pale yellow solid.

$^1$H NMR (400 MHz; CDCl$_3$) δ 7.83 (d, 1 H, J=2.0 Hz); 7.63 (d, 1 H, J=2.0 Hz); 7.45 (d, 1 H, J=2.0 Hz); 7.29 (dd, 1 H, J=8.2, 2.0 Hz); 7.13 (s, 1 H Hz); 7.04 (d, 1 H, J=2.0 Hz); 6.98 (d, 1 H, J=2.0 Hz); 6.46 (d, 1 H, J=8.2 Hz); 4.66 (d, 1 H, J=3.1 Hz); 4.42 (dd, 1 H, J=11.0, 2.7 Hz); 4.19 (s, 1 H); 3.94 (s, 3 H); 3.80 (m, 1 H); 2.10 (m, 1 H); 1.41-1.55 (s, 6 H). MS mz (M+H): 428.9.

B. Preparation of a Compound of Formula I, varying $R^1$, $R^2$, $R^3$, $R^4$, $R^5$, $R^6$, $R^7$, $R^8$, $R^{20}$, and X Similarly, following the procedure of 14A above, but replacing (6aR,12aS)-6a,7,12,12a-tetrahydro-4-methoxy-7,7-dimethyl-9-(oxazol-5-yl)-2-(1H-pyrazol-4-yl)-6H-chromeno[4,3-b]quinoline with other compounds of formula I, or replacing 4,4,5,5-tetramethyl-2-pyrazol-4-yl-1,3,2-dioxaborolane with other dioxaborolane derivatives, the following compounds of formula I were prepared.

- (6aS,12aS)-6a,7,12,12a-tetrahydro-4-methoxy-7,7-dimethyl-9-(oxazol-5-yl)-2-(1H-pyrazol-4-yl)-6H-chromeno[4,3-b]quinoline;
- (6aR,12aS)-methyl 6a,7,12,12a-tetrahydro-4-methoxy-7,7-dimethyl-2-(1 H-pyrazol-4-yl)-6H-chromeno[4,3-b]quinoline-9-carboxylate;
- (6aR,12aS)-methyl 6a,7,12,12a-tetrahydro-4-methoxy-7,7-dimethyl-2-(3,5-dimethylisoxazol-4-yl)-6H-chromeno[4,3-b]quinoline-9-carboxylate; and
- (6aR,12aS)-6a,7,12,12a-tetrahydro-4-methoxy-7,7-dimethyl-2-(3,5-dimethylisoxazol-4-yl)-9-(oxazol-5-yl)-6H-chromeno[4,3-b]quinoline.
- diethyl (6a,7,12,12a-tetrahydro-1-methoxy-7,7-dimethyl-6H-chromeno[4,3-b]quinolin-9-yl)methylphosphonate;
- diethyl ((6aR,12aS)-6a,7,12,12a-tetrahydro-4-methoxy-7,7-dimethyl-2-(1H-pyrazol-4-yl)-6H-chromeno[4,3-b]quinolin-9-yl)methylphosphonate; and
- (6aR, 12aS)-6a,7,12,12a-tetrahydro-4-methoxy-7,7-dimethyl-2-(1H-pyrazol-4-yl)-6H-chromeno[4,3-b]quinoline-9-carbonitrile.

C. Preparation of a Compound of Formula I, varying $R^1$, $R^2$, $R^3$, $R^4$, $R^5$, $R^6$, $R^7$, $R^8$, $R^{20}$, and X Similarly, following the procedure of 14A above, but replacing (6aR,12aS)-6a,7,12,12a-tetrahydro-4-methoxy-7,7-dimethyl-9-(oxazol-5-yl)-2-(1H-pyrazol-4-yl)-6H-chromeno[4,3-b]quinoline with other compounds of formula I, or replacing 4,4,5,5-tetramethyl-2-pyrazol-4-yl-1,3,2-dioxaborolane with other dioxaborolane derivatives, other compounds of Formula I are prepared.

EXAMPLE 15

Several compounds of Formula I prepared as shown in the above procedures were characterized by NMR and mass spectrometry. For example:

2-((6aS,12aR-2-bromo-7,7-dimethyl(7,12,12a,6a-tetrahydrochromano[4,3-b]quinolin-9-yl))-1,1,1,3,3,3-hexafluoropropan-2-ol $^1$H NMR (400 MHz, CDCl$_3$) δ 1.36(s, 3H), 1.46(s, 3H), 2.01(apparent dt, J=12.1, 3.5 Hz, 1H), 3.4(bs, 1H), 3.74(dd, J=12.1, 10.9 Hz, 1H), 4.1(bs, 1H), 4.25(ddd, J=189, 3.9, 1.6 Hz, 1H), 4.56(d, J=2.7 Hz, 1H), 7.28(d, J=10.1 Hz, 1H), 7.32(dd, J=8.6, 2.3 Hz, 1H), 7.36(d, J=2.3 Hz, 1H), 7.45(d, J=1.5 Hz, 1H)

2-((12aS,6aS)-2-bromo-7,7-dimethyl(7,12,12a,6a-tetrahydrochromano[4,3-b]guinolin-9-yl))-1,1,1,3,3,3-hexafluoropropan-2-ol;

$^1$H NMR (400 MHz, CDCl$_3$) δ 1.21(s, 3H), 1.48(s, 3H), 2.06(ddd, J=10.9, 10.9, 3.1 Hz, 1H), 3.92(t, J=10.9 Hz, 1H), 4.45(d, J=10.5 Hz, 1H), 4.46(bs, 1H), 4.5(dd, J=10.9, 3.2 Hz, 1H), 6.72(d, J=8.6 Hz, 1H), 6.78(d, J=8.6 Hz, 1H), 7.3(dd, J=8.6, 2.3 Hz, 1H), 7.34(d, J=8.6 Hz, 1H), 7.42(d, J=2.3 Hz, 1H), 7.6(s, 1H)

EXAMPLE 16 mRNA ASSAYS

Modulation of expression of ABCA1 mRNA levels by the compounds of the invention was determined in the following assays.

Induction of ABC1 in THP-1 cells, was measured using QuantiGene® branched DNA assay as per manufacturer's instructions. Cultures of THP-1 were grown to subconfluence in DMEM/10% FBS before replacement with DMEM/BSA and 10 and 3 μM concentrations of the test compounds in DMSO for 18-20 hours. After treatment of cells with compounds, the cells were lysed with lysis buffer at 37° C. for 20 minutes. The cell lysate and ABCA1 specific probe (Genospectra, Inc., Fremont, Calif.) mix were added to the 96 well capture plate and hybridized at 53° C. for 16-18 hours. The signal was amplified using the amplifier and label probes provided with the QuantiGene® assay followed by addition of a luminescent alkaline phosphatase substrate, dioxitane. Luminescence was quantified in Victor V plate reader.

Step 1

Cells are lysed to release mRNA in the presence of target probes. Target mRNA from lysed cells was then captured by hybridization and transferred to the Capture Plate.

Step 2

Signal amplification was performed by hybridization of the bDNA Amplifier and Label Probe.

Step 3

Addition of chemiluminescence substrate yielded a QuantiGene® signal proportional to the amount of mRNA present in the sample.

The compounds of the invention demonstrated increased ABCA1 gene expression in this assay relative to a DMSO control. Table 1 presents the relative fold increase in ABCA1 expression over DMSO for various compounds of the invention when tested at a concentration of 10 μM.

TABLE 1

ABCA1 Induction Fold Increase over DMSO Vehicle at 10 μM

| NUMBER | NAME | FOLD INCREASE |
|---|---|---|
| 1. | 2-(2-bromo-7,7-dimethyl(7,12,12a,6a-tetrahydrochromano[4,3-b]quinolin-9-yl))-1,1,1,3,3,3-hexafluoropropan-2-ol; | 4.4 |
| 2. | 2-((6aS,12aR)-2-bromo-7,7-dimethyl(7,12,12a,6a-tetrahydrochromano[4,3-b]quinolin-9-yl))-1,1,1,3,3,3-hexafluoropropan-2-ol; | 5.1 |
| 3. | 2-((12aS,6aS)-2-bromo-7,7-dimethyl(7,12,12a,6a-tetrahydrochromano[4,3-b]quinolin-9-yl))-1,1,1,3,3,3-hexafluoropropan-2-ol; | 3.0 |
| 4. | 2-(2-bromo-7,7-dimethyl-7,12,12a,6a-tetrahydrochromano[4,3-b]quinolin-9-yl)acetic acid; | 2.1 |
| 5. | 2-bromo-7,7-dimethyl-7,12,12a,6a-tetrahydrochromano[4,3-b]quinoline-9-carboxamide; | 3.5 |
| 6. | methyl 2-bromo-10-methoxy-7,7-dimethyl-7,12,12a,6a-tetrahydrochromano[4,3-b]quinoline-9-carboxylate; | 1.6 |
| 7. | 1,1,1,3,3,3-hexafluoro-2-(2-methoxy-7,7-dimethyl(7,12,12a,6a-tetrahydrochromano[4,3-b]quinolin-9-yl))propan-2-ol; | 3.1 |
| 8. | 2-[7,7-dimethyl-2-(trifluoromethoxy)(7,12,12a,6a-tetrahydrochromano[4,3-b]quinolin-9-yl)]-1,1,1,3,3,3-hexafluoropropan-2-ol; | 3.0 |
| 9. | 2-[(12aS,6aS)-7,7-dimethyl-2-(trifluoromethoxy)(7,12,12a,6a-tetrahydrochromano[4,3-b]quinolin-9-yl)]-1,1,1,3,3,3-hexafluoropropan-2-ol; | 2.4 |
| 10. | 3-methylbut-2-enyl (6aS,12aR)-9-(dihydroxyboramethyl)-7,7-dimethyl-7,12,12a,6a-tetrahydrochromano[4,3-b]quinoline-3-carboxylate; | 1.5 |
| 11. | 3-methylbut-2-enyl 9-(dihydroxyboramethyl)-7,7-dimethyl-7,12,12a,6a-tetrahydrochromano[4,3-b]quinoline-3-carboxylate; | 1.7 |
| 12. | 3-methylbut-2-enyl 7,7-dimethyl-9-[2,2,2-trifluoro-1-hydroxy-1-(trifluoromethyl)ethyl]-7,12,12a,6a-tetrahydrochromano[4,3-b]quinoline-3-carboxylate; | 4.6 |
| 13. | 3-methylbut-2-enyl 7,7-dimethyl-9-[2,2,2-trifluoro-1-hydroxy-1-(trifluoromethyl)ethyl]-7,12,12a,6a-tetrahydrochromano[4,3-b]quinoline-2-carboxylate; | 3.4 |
| 14. | 7,7-dimethyl-9-[2,2,2-trifluoro-1-hydroxy-1-(trifluoromethyl)ethyl]-7,12,12a,6a-tetrahydrochromano[4,3-b]quinoline-3-carboxylic acid; | 3.1 |
| 15. | 3-methylbut-2-enyl 9-(dihydroxyboramethyl)-7,7-dimethyl-7,12,12a,6a-tetrahydrochromano[4,3-b]quinoline-2-carboxylate; | 1.8 |
| 16. | 7,7-dimethyl-9-[2,2,2-trifluoro-1-hydroxy-1-(trifluoromethyl)ethyl]-7,12,12a,6a-tetrahydrochromano[4,3-b]quinoline-2-carboxylic acid; | 2.4 |
| 17. | 9-(dihydroxyboramethyl)-7,7-dimethyl-7,12-dihydro-6H-chromeno[4,3-b]quinoline-3-carboxylic acid; | 1.8 |
| 18. | 1,1,1,3,3,3-hexafluoro-2-(4,7,7-trimethyl(7,12,12a,6a-tetrahydrochromano[4,3-b]quinolin-9-yl))propan-2-ol; | 5.3 |
| 19. | 4-methoxy-7,7-dimethyl-9-(1,2,3,4-tetraazol-5-yl)-7,12,12a,6a-tetrahydrochromano[4,3-b]quinoline; | 5.6 |

TABLE 1-continued

ABCA1 Induction Fold Increase over DMSO Vehicle at 10 μM

| NUMBER | NAME | FOLD INCREASE |
|---|---|---|
| 20. | 4-((6aS,12aR)-4-methoxy-7,7-dimethyl-7,12,12a,6a-tetrahydrochromano[4,3-b]quinolin-9-yl)-1,4-thiazaperhydroine-1,1-dione; | 6.5 |
| 21. | 4-(4-methoxy-7,7-dimethyl-7,12,12a,6a-tetrahydrochromano[4,3-b]quinolin-9-yl)-1,4-thiazaperhydroine-1,1-dione; | 5.6 |
| 22. | 2-(4-ethoxy-7,7-dimethyl(7,12,12a,6a-tetrahydrochromano[4,3-b]quinolin-9-yl))-1,1,1,3,3,3-hexafluoropropan-2-ol; | 4.8 |
| 23. | 4-methoxy-7,7-dimethyl-7,12,12a,6a-tetrahydrochromano[4,3-b]quinoline-9-carboxamide; | 6.1 |
| 24. | 1,1,1,3,3,3-hexafluoro-2-(1-methoxy-7,7-dimethyl(7,12,12a,6a-tetrahydrochromano[4,3-b]quinolin-9-yl))propan-2-ol; | 6.5 |
| 25. | 2-[7,7-dimethyl-4-(3-methylbut-2-enyloxy)(7,12,12a,6a-tetrahydrochromano[4,3-b]quinolin-9-yl)]-1,1,1,3,3,3-hexafluoropropan-2-ol; | 4.0 |
| 26. | 2-(4-methoxy-7,7-dimethyl-7,12,12a,6a-tetrahydrochromano[4,3-b]quinolin-9-yl)acetic acid; | 5.0 |
| 27. | 3-((6aS,12aR)-4-methoxy-7,7-dimethyl-7,12,12a,6a-tetrahydrochromano[4,3-b]quinolin-9-yl)propanoic acid; | 3.3 |
| 28. | 3-((12aR,6aR)-4-methoxy-7,7-dimethyl-7,12,12a,6a-tetrahydrochromano[4,3-b]quinolin-9-yl)propanoic acid; | 1.9 |
| 29. | 4,7,7-trimethyl-7,12,12a,6a-tetrahydrochromano[4,3-b]quinoline-9-carboxamide; | 5.8 |
| 30. | 4-ethoxy-7,7-dimethyl-7,12,12a,6a-tetrahydrochromano[4,3-b]quinoline-9-carboxamide; | 5.3 |
| 31. | 4,7,7-trimethyl-7,12,12a,6a-tetrahydrochromano[4,3-b]quinoline; | 5.5 |
| 32. | (12aS)-4,7,7-trimethyl-7,12,12a,6a-tetrahydrochromano[4,3-b]quinoline; | 4.9 |
| 33. | 1,1,1,3,3,3-hexafluoro-2-(4-methoxy-7,7-dimethyl(7,12,12a,6a-tetrahydrochromano[4,3-b]quinolin-9-yl))propan-2-ol; | 6.4 |
| 34. | 2-((6aR)-4-methoxy-7,7-dimethyl(7,12,12a,6a-tetrahydrochromano[4,3-b]quinolin-9-yl))-1,1,1,3,3,3-hexafluoropropan-2-ol; | 4.5 |
| 35. | methyl (2E)-3-{7,7-dimethyl-9-[2,2,2-trifluoro-1-hydroxy-1-(trifluoromethyl)ethyl](7,12,12a,6a-tetrahydrochromano[4,3-b]quinolin-2-yl)}prop-2-enoate; | 4.3 |
| 36. | (2E)-3-{7,7-dimethyl-9-[2,2,2-trifluoro-1-hydroxy-1-(trifluoromethyl)ethyl](7,12,12a,6a-tetrahydrochromano[4,3-b]quinolin-2-yl)}-N,N-dimethylprop-2-enamide; | 5.3 |
| 37. | (6aS,12aR)-4-methoxy-7,7-dimethyl-7,12,12a,6a-tetrahydrochromano[4,3-b]quinoline; | 8.3 |
| 38. | (12aS,6aS)-4-methoxy-7,7-dimethyl-7,12,12a,6a-tetrahydrochromano[4,3-b]quinoline; | 7.0 |
| 39. | 3-{7,7-dimethyl-9-[2,2,2-trifluoro-1-hydroxy-1-(trifluoromethyl)ethyl](7,12,12a,6a-tetrahydrochromano[4,3-b]quinolin-2-yl)}-N,N-dimethylpropanamide; | 3.4 |
| 40. | methyl 3-{7,7-dimethyl-9-[2,2,2-trifluoro-1-hydroxy-1-(trifluoromethyl)ethyl]-7,12,12a,6a-tetrahydrochromano[4,3-b]quinolin-2-yl}propanoate; | 2.1 |
| 41. | 4-ethoxy-7,7-dimethyl-9-(trifluoromethyl)-7,12,12a,6a-tetrahydrochromano[4,3-b]quinoline; | 2.1 |
| 42. | 1-(4-ethoxy-7,7-dimethyl-7,12,12a,6a-tetrahydrochromano[4,3-b]quinolin-9-yl)ethan-1-one; | 3.8 |
| 43. | 1-(1-methoxy-7,7-dimethyl-7,12,12a,6a-tetrahydrochromano[4,3-b]quinolin-9-yl)ethan-1-one; | 4.1 |
| 44. | 1-methoxy-7,7-dimethyl-9-(trifluoromethy;1)-7,12,12a,6a-tetrahydrochromano[4,3-b]quinoline; | 2.2 |
| 45. | 1-methoxy-7,7-dimethyl-7,12,12a,6a-tetrahydrochromano[4,3-b]quinoline-9-carboxamide; | 4.9 |
| 46. | (6aS,12aR)-4-methoxy-7,7-dimethyl-9-(methylethyl)-7,12,12a,6a-tetrahydrochromano[4,3-b]quinoline; | 4.2 |
| 47. | (12aS,6aS)-4-methoxy-7,7-dimethyl-9-(methylethyl)-7,12,12a,6a-tetrahydrochromano[4,3-b]quinoline; | 3.6 |
| 48. | (6aS,12aR)-9-fluoro-4-methoxy-7,7-dimethyl-7,12,12a,6a-tetrahydrochromano[4,3-b]quinoline; | 3.7 |
| 49. | (12aS,6aS)-4-methoxy-7,7-dimethyl-7,12,12a,6a-tetrahydrochromano[4,3-b]quinoline-9-carboxylic acid; | 1.7 |
| 50. | 4-fluoro-7,7-dimethyl-7,12,12a,6a-tetrahydrochromano[4,3-b]quinoline-9-carboxamide; | 5.0 |
| 51. | 1,1,1,3,3,3-hexafluoro-2-(4-fluoro-7,7-dimethyl(7,12,12a,6a-tetrahydrochromano[4,3-b]quinolin-9-yl))propan-2-ol; | 7.8 |
| 52. | ((6aS,12aR)-4-methoxy-7,7-dimethyl(7,12,12a,6a-tetrahydrochromano[4,3-b]quinolin-9-yloxy))trifluoromethane; | 9.5 |
| 53. | (12aS,6aR)-1-methoxy-7,7-dimethyl-7,12,12a,6a-tetrahydrochromano[4,3-b]quinoline; | 3.5 |

TABLE 1-continued

ABCA1 Induction Fold Increase over DMSO Vehicle at 10 µM

| NUMBER | NAME | FOLD INCREASE |
|---|---|---|
| 54. | (12aS,6aR)-1-methoxy-7,7-dimethyl-9-(methylethyl)-7,12,12a,6a-tetrahydrochromano[4,3-b]quinoline; | 4.3 |
| 55. | (12aS,6aR)-9-fluoro-1-methoxy-7,7-dimethyl-7,12,12a,6a-tetrahydrochromano[4,3-b]quinoline; | 2.5 |
| 56. | (12aS,6aR)-9-ethoxy-1-methoxy-7,7-dimethyl-7,12,12a,6a-tetrahydrochromano[4,3-b]quinoline; | 4.8 |
| 57. | ((12aS,6aR)-1-methoxy-7,7-dimethyl(7,12,12a,6a-tetrahydrochromano[4,3-b]quinolin-9-yloxy))trifluoromethane; | 6.1 |
| 58. | amino(4-methoxy-7,7-dimethyl(7,12,12a,6a-tetrahydrochromano[4,3-b]quinolin-9-yl))methane-1-thione; | 6.2 |
| 59. | {[(4-methoxy-7,7-dimethyl(7,12,12a,6a-tetrahydrochromano[4,3-b]quinolin-9-yl))methyl]sulfonyl}methylamine; | 6.1 |
| 60. | methylethyl 3-(4-methoxy-7,7-dimethyl-7,12,12a,6a-tetrahydrochromano[4,3-b]quinolin-9-yl)benzoate; | 4.4 |
| 61. | methylethyl 3-(4-methoxy-7,7-dimethyl-7,12-dihydro-6H-chromeno[4,3-b]quinolin-9-yl)benzoate; | 2.0 |
| 62. | (12aS,6aR)-1-methoxy-7,7-dimethyl-9-(1,3-oxazol-5-yl)-7,12,12a,6a-tetrahydrochromano[4,3-b]quinoline; | 10.6 |
| 63. | (12aS,6aR)-1-methoxy-7,7-dimethyl-7,12,12a,6a-tetrahydrochromano[4,3-b]quinoline-10-carbonitrile; | 3.5 |
| 64. | 2-((6aS,12aR)-1-bromo-4-methoxy-7,7-dimethyl(7,12,12a,6a-tetrahydrochromano[4,3-b]quinolin-9-yl))-1,1,1,3,3,3-hexafluoropropan-2-ol; | 2.5 |
| 65. | 2-((6aS,12aR)-2-bromo-4-methoxy-7,7-dimethyl(7,12,12a,6a-tetrahydrochromano[4,3-b]quinolin-9-yl))-1,1,1,3,3,3-hexafluoropropan-2-ol; | 3.2 |
| 66. | 2-((12aR,6aR)-2-bromo-4-methoxy-7,7-dimethyl(7,12,12a,6a-tetrahydrochromano[4,3-b]quinolin-9-yl))-1,1,1,3,3,3-hexafluoropropan-2-ol; | 2.5 |
| 67. | 2-(2,4-difluoro-7,7-dimethyl(7,12,12a,6a-tetrahydrochromano[4,3-b]quinolin-9-yl))-1,1,1,3,3,3-hexafluoropropan-2-ol; | 3.3 |
| 68. | 2-(2,4-dichloro-7,7-dimethyl(7,12,12a,6a-tetrahydrochromano[4,3-b]quinolin-9-yl))-1,1,1,3,3,3-hexafluoropropan-2-ol; | 2.7 |
| 69. | 2-(2-chloro-4,7,7-trimethyl(7,12,12a,6a-tetrahydrochromano[4,3-b]quinolin-9-yl))-1,1,1,3,3,3-hexafluoropropan-2-ol; | 2.6 |
| 70. | 2-((6aS,12aR)-7,7-dimethyl(7,12,12a,6a-tetrahydrochromano[4,3-b]quinolin-9-yl))-1,1,1,3,3,3-hexafluoropropan-2-ol; | 4.0 |
| 71. | (12aS,6aR)-1-methoxy-7,7-dimethyl-9-(1,2,3,4-tetraazol-5-yl)-7,12,12a,6a-tetrahydrochromano[4,3-b]quinoline; | 9.5 |
| 72. | 4-((12aS,6aR)-1-methoxy-7,7-dimethyl-7,12,12a,6a-tetrahydrochromano[4,3-b]quinolin-9-yl)-1,4-thiazaperhydroine-1,1-dione; | 8.4 |
| 73. | (12aS,6aR)-1-methoxy-7,7-dimethyl-9-(1,2,3-thiadiazol-4-yl)-7,12,12a,6a-tetrahydrochromano[4,3-b]quinoline; and | 8.0 |
| 74. | 1-methoxy-7,7-dimethyl-9-(4-methyl(1,2,4-triazol-3-yl))-7,12,12a,6a-tetrahydrochromano[4,3-b]quinoline. | 7.9 |
| 75. | 9-bromo-4-methoxy-7,7-dimethyl-7,12,12a,6a-tetrahydrochromano[4,3-b]quinoline; | 7.4 |
| 76. | 4-methoxy-7,7-dimethyl-9-(1,2,3,4-tetraazol-5-ylmethyl)-7,12,12a,6a-tetrahydrochromano[4,3-b]quinoline; | 6.0 |
| 77. | 2-((12aS,6aR)-4-methoxy-7,7-dimethyl-2-phenyl(7,12,12a,6a-tetrahydrochromano[4,3-b]quinolin-9-yl))-1,1,1,3,3,3-hexafluoropropan-2-ol | 5.3 |
| 78. | 1-bromo-9-ethoxy-4-methoxy-7,7-dimethyl-7,12,12a,6a-tetrahydrochromano[4,3-b]quinoline; | 2.7 |
| 79. | 1-bromo-4-methoxy-7,7-dimethyl-9-(1,3-oxazol-5-yl)-7,12,12a,6a-tetrahydrochromano[4,3-b]quinoline; | 4.1 |
| 80. | 1-(1-bromo-4-methoxy-7,7-dimethyl-7,12,12a,6a-tetrahydrochromano[4,3-b]quinolin-9-yl)ethan-1-one; | 4.3 |
| 81. | 1-bromo-4-methoxy-7,7-dimethyl-7,12,12a,6a-tetrahydrochromano[4,3-b]quinoline-9-carboxamide; | 1.9 |
| 82. | amino(1-bromo-4-methoxy-7,7-dimethyl(7,12,12a,6a-tetrahydrochromano[4,3-b]quinolin-9-yl))methane-1-thione; | 2.0 |
| 83. | 1-bromo-4-methoxy-7,7-dimethyl-9-(methylethoxy)-7,12,12a,6a-tetrahydrochromano[4,3-b]quinoline; | 2.7 |
| 84. | (12aS,6aR)-1-methoxy-7,7-dimethyl-9-(1,2,3,4-tetraazol-5-ylmethyl)-7,12,12a,6a-tetrahydrochromano[4,3-b]quinoline; | 8.6 |
| 85. | (12aS,6aR)-9-bromo-1-methoxy-7,7-dimethyl-7,12,12a,6a-tetrahydrochromano[4,3-b]quinoline; | 8.0 |
| 86. | (12aS,6aR)-9-bromo-4-methoxy-7,7-dimethyl-7,12,12a,6a-tetrahydrochromano[4,3-b]quinoline; | 8.4 |
| 87. | (12aS,6aS)-9-bromo-4-methoxy-7,7-dimethyl-7,12,12a,6a-tetrahydrochromano[4,3-b]quinoline; | 7.4 |

TABLE 1-continued

ABCA1 Induction Fold Increase over DMSO Vehicle at 10 μM

| NUMBER | NAME | FOLD INCREASE |
|---|---|---|
| 88. | 9-(tert-butyl)-1-methoxy-7,7-dimethyl-7,12,12a,6a-tetrahydrochromano[4,3-b]quinoline; | 6.8 |
| 89. | {[(1-methoxy-7,7-dimethyl(7,12,12a,6a-tetrahydrochromano[4,3-b]quinolin-9-yl))methyl]sulfonyl}methylamine; | 6.4 |
| 90. | diethoxy[(1-methoxy-7,7-dimethyl(7,12,12a,6a-tetrahydrochromano[4,3-b]quinolin-9-yl))methyl]phosphino-1-one; | 7.6 |
| 91. | [(2-chloro-4-methoxy-7,7-dimethyl(7,12,12a,6a-tetrahydrochromano[4,3-b]quinolin-9-yl))methyl]diethoxyphosphino-1-one; | 6.2 |
| 92. | 4-((12aS,6aS)-1-methoxy-7,7-dimethyl-7,12,12a,6a-tetrahydrochromano[4,3-b]quinolin-9-yl)benzenecarbonitrile; | 8.7 |
| 93. | (12aS,6aS)-1-methoxy-7,7-dimethyl-9-[4-(trifluoromethyl)phenyl]-7,12,12a,6a-tetrahydrochromano[4,3-b]quinoline; | 6.8 |
| 94. | (12aS,6aS)-1-methoxy-7,7-dimethyl-9-phenyl-7,12,12a,6a-tetrahydrochromano[4,3-b]quinoline; | 5.8 |
| 95. | (12aS,6aR)-9-ethynyl-1-methoxy-7,7-dimethyl-7,12,12a,6a-tetrahydrochromano[4,3-b]quinoline; | 4.3 |
| 96. | ethyl 4-((12aS,6aS)-1-methoxy-7,7-dimethyl-7,12,12a,6a-tetrahydrochromano[4,3-b]quinolin-9-yl)benzoate; | 7.6 |
| 97. | 4-((12aS,6aS)-1-methoxy-7,7-dimethyl-7,12,12a,6a-tetrahydrochromano[4,3-b]quinolin-9-yl)benzenesulfonamide; | 5.7 |
| 98. | [4-((12aS,6aS)-1-methoxy-7,7-dimethyl-7,12,12a,6a-tetrahydrochromano[4,3-b]quinolin-9-yl)phenyl]methan-1-ol; | 5.2 |
| 99. | (12aS,6aR)-9-(4-fluorophenyl)-4-methoxy-7,7-dimethyl-7,12,12a,6a-tetrahydrochromano[4,3-b]quinoline; | 1.7 |
| 100. | 1-(2-chloro-4-methoxy-7,7-dimethyl(7,12,12a,6a-tetrahydrochromano[4,3-b]quinolin-9-yl))-2-methoxybenzene; | 3.0 |
| 101. | 1-(4-fluoro-7,7-dimethyl-7,12,12a,6a-tetrahydrochromano[4,3-b]quinolin-9-yl)ethan-1-one; | 4.0 |
| 102. | 4-fluoro-7,7-dimethyl-9-(methylethoxy)-7,12,12a,6a-tetrahydrochromano[4,3-b]quinoline; | 4.2 |
| 103. | (12aS)-4-fluoro-7,7-dimethyl-9-(methylethoxy)-7,12,12a,6a-tetrahydrochromano[4,3-b]quinoline; | 4.0 |
| 104. | 4-fluoro-9-(2-methoxyphenyl)-7,7-dimethyl-7,12-dihydro-6H-chromeno[4,3-b]quinolin-12-ol; | 2.9 |
| 105. | (2-chloro-4-methoxy-7,7-dimethyl(7,12,12a,6a-tetrahydrochromano[4,3-b]quinolin-9-yl))[(4-methylphenyl)sulfonyl]amine; | 3.6 |
| 106. | 4-((12aS,6aR)-1-methoxy-7,7-dimethyl-7,12,12a,6a-tetrahydrochromano[4,3-b]quinolin-9-yl)benzoic acid | 4.8 |
| 107. | ethyl 4-((12aS,6aR)-1-methoxy-7,7-dimethyl-7,12,12a,6a-tetrahydrochromano[4,3-b]quinolin-9-yl)benzoate; | 2.9 |
| 108. | 4-((12aS,6aR)-1-methoxy-7,7-dimethyl-7,12,12a,6a-tetrahydrochromano[4,3-b]quinolin-9-yl)benzamide; | 4.7 |
| 109. | (12aS,6aR)-9-(4-fluorophenyl)-1-methoxy-7,7-dimethyl-7,12,12a,6a-tetrahydrochromano[4,3-b]quinoline; | 4.1 |
| 110. | (12aS,6aR)-1-methoxy-7,7-dimethyl-9-(2-methyl(1,3-thiazol-4-yl))-7,12,12a,6a-tetrahydrochromano[4,3-b]quinoline; | 6.0 |
| 111. | (12aS,6aR)-1-methoxy-7,7-dimethyl-9-pyrazol-3-yl-7,12,12a,6a-tetrahydrochromano[4,3-b]quinoline; | 4.7 |
| 112. | 1-((12aS,6aR)-1-methoxy-7,7-dimethyl(7,12,12a,6a-tetrahydrochromano[4,3-b]quinolin-9-yl))-4-methoxybenzene; | 1.7 |
| 113. | methyl 3-((12aS,6aR)-1-methoxy-7,7-dimethyl-7,12,12a,6a-tetrahydrochromano[4,3-b]quinolin-9-yl)benzoate; | 1.5 |
| 114. | 3-[4-((12aS,6aR)-1-methoxy-7,7-dimethyl-7,12,12a,6a-tetrahydrochromano[4,3-b]quinolin-9-yl)phenyl]propanoic acid; | 2.7 |
| 115. | (2E)-3-[4-((12aS,6aR)-1-methoxy-7,7-dimethyl(7,12,12a,6a-tetrahydrochromano[4,3-b]quinolin-9-yl))phenyl]prop-2-enoic acid; | 2.2 |
| 116. | ethyl 1-((6aR,12aS)-6a,7,12,12a-tetrahydro-1-methoxy-7,7-dimethyl-6H-chromeno[4,3-b]quinolin-9-yl)-5-methyl-1H-pyrazole-4-carboxylate; | 2.7 |
| 117. | (6aR,12aS)-6a,7,12,12a-tetrahydro-N-(2-hydroxyethyl)-1-methoxy-7,7-dimethyl-6H-chromeno[4,3-b]quinoline-9-carboxamide; | 8.6 |
| 118. | 1-((6aR,12aS)-6a,7,12,12a-tetrahydro-1-methoxy-7,7-dimethyl-6H-chromeno[4,3-b]quinolin-9-yl)-5-methyl-1H-pyrazole-4-carboxylic acid; | 4 |
| 119. | ((6aR,12aS)-6a,7,12,12a-tetrahydro-4-methoxy-7,7-dimethyl-6H-chromeno[4,3-b]quinolin-9-yl)(morpholino)methanone; | 7.5 |
| 120. | ((6aS,12aS)-6a,7,12,12a-tetrahydro-4-methoxy-7,7-dimethyl-6H-chromeno[4,3-b]quinolin-9-yl)(morpholino)methanone; | 4.2 |
| 121. | ((6aR,12aS)-6a,7,12,12a-tetrahydro-1-methoxy-7,7-dimethyl-6H-chromeno[4,3-b]quinolin-9-yl)(1,1-dione-1,4-thiazaperhydroin-yl)methanone; | 3.2 |

TABLE 1-continued

ABCA1 Induction Fold Increase over DMSO Vehicle at 10 μM

| NUMBER | NAME | FOLD INCREASE |
|---|---|---|
| 122. | (6aR,12aS)-6a,7,12,12a-tetrahydro-1-methoxy-7,7-dimethyl-9-(methylsulfonyl)-6H-chromeno[4,3-b]quinoline; | 2.4 |
| 123. | (6aR,12aS)-6a,7,12,12a-tetrahydro-1-methoxy-N,N,7,7-tetramethyl-6H-chromeno[4,3-b]quinolin-9-carboxamide; | 6.5 |
| 124. | 2-((6aR,12aS)-6a,7,12,12a-tetrahydro-1-methoxy-7,7-dimethyl-6H-chromeno[4,3-b]quinolin-9-ylsulfonyl)acetic acid; | 3.3 |
| 125. | ((6aR,12aS)-6a,7,12,12a-tetrahydro-1-methoxy-7,7-dimethyl-6H-chromeno[4,3-b]quinolin-9-yl)(4-tert-butyl-carboxylate-piperazin-1-yl)methanone; | 4.1 |
| 126. | ((6aR,12aS)-6a,7,12,12a-tetrahydro-1-fluoro-7,7-dimethyl-6H-chromeno[4,3-b]quinolin-9-yl)(4-tert-butyl-carboxylate-piperazin-1-yl)methanone; | 7.3 |
| 127. | ((6aR,12aS)-6a,7,12,12a-tetrahydro-1-methoxy-7,7-dimethyl-6H-chromeno[4,3-b]quinolin-9-yl)(piperazin-1-yl)methanone; | 5.1 |
| 128. | ((6aS,12aS)-6a,7,12,12a-tetrahydro-4-methoxy-7,7-dimethyl-6H-chromeno[4,3-b]quinolin-9-yl)(1,1-dione-1,4-thiazaperhydroin-yl)methanone; | 2.7 |
| 129. | ((6aR,12aS)-6a,7,12,12a-tetrahydro-4-methoxy-7,7-dimethyl-6H-chromeno[4,3-b]quinolin-9-yl)(1,1-dione-1,4-thiazaperhydroin-yl)methanone; | 4.3 |
| 130. | ((6aR,12aS)-1-fluoro-6a,7,12,12a-tetrahydro-7,7-dimethyl-6H-chromeno[4,3-b]quinolin-9-yl)(piperazin-1-yl)methanone; | 4.2 |
| 131. | 2-((6aR,12aS)-1-fluoro-6a,7,12,12a-tetrahydro-7,7-dimethyl-6H-chromeno[4,3-b]quinolin-9-yl)oxazole-4-carboxylic acid; | 2 |
| 132. | ((6aR,12aS)-1-methoxy-6a,7,12,12a-tetrahydro-7,7-dimethyl-6H-chromeno[4,3-b]quinolin-9-yl)(4-ethanesulfonylpiperazin-1-yl)methanone; | 4.3 |
| 133. | ((6aS,12aS)-4-methoxy-6a,7,12,12a-tetrahydro-7,7-dimethyl-6H-chromeno[4,3-b]quinolin-9-yl)(4-ethanesulfonylpiperazin-1-yl)methanone; | 3.8 |
| 134. | ((6aR,12aS)-4-methoxy-6a,7,12,12a-tetrahydro-7,7-dimethyl-6H-chromeno[4,3-b]quinolin-9-yl)(4-ethanesulfonylpiperazin-1-yl)methanone; and | 5.8 |
| 135. | ethyl 1-((6aR,12aS)-6a,7,12,12a-tetrahydro-1-methoxy-7,7-dimethyl-6H-chromeno[4,3-b]quinolin-9-yl)-1H-pyrazole-4-carboxylate; | 6.4 |
| 136. | 1-((6aR,12aS)-6a,7,12,12a-tetrahydro-1-methoxy-7,7-dimethyl-6H-chromeno[4,3-b]quinolin-9-yl)-1H-pyrazole-4-carboxylic acid; | 4.1 |
| 137. | 1-((6aR,12aS)-6a,7,12,12a-tetrahydro-1-methoxy-7,7-dimethyl-6H-chromeno[4,3-b]quinolin-9-yl)-N,N-dimethyl-1H-pyrazole-4-carboxamide; | 7 |
| 138. | 1-((6aR,12aS)-6a,7,12,12a-tetrahydro-1-methoxy-7,7-dimethyl-6H-chromeno[4,3-b]quinolin-9-yl)1-1H-pyrazole-4-((1,1-dione-1,4-thiazaperhydroin-yl)methanone); | 7.4 |
| 139. | ((6aS,12aS)-4-fluoro-6a,7,12,12a-tetrahydro-7,7-dimethyl-6H-chromeno[4,3-b]quinolin-9-yl)(4-ethanesulfonylpiperazin-1-yl)methanone. | 2.8 |
| 140. | 1-((6aR,12aS)-6a,7,12,12a-tetrahydro-1-methoxy-7,7-dimethyl-6H-chromeno[4,3-b]quinolin-9-yl)-5-methyl-1H-pyrazole-4-((4-ethanesulfonylpiperazin-1-yl)methanone); | 5.1 |
| 141. | 1-((6aR,12aS)-6a,7,12,12a-tetrahydro-1-methoxy-7,7-dimethyl-6H-chromeno[4,3-b]quinolin-9-yl)1-5-methyl-1H-pyrazole-4-((1,1-dione-1,4-thiazaperhydroin-yl)methanone); | 7.1 |
| 142. | 2-((6aR,12aS)-1-fluoro-6a,7,12,12a-tetrahydro-7,7-dimethyl-6H-chromeno[4,3-b]quinolin-9-yl)oxazole-(4-(4-ethanesulfonylpiperazin-1-yl)methanone); | 5 |
| 143. | 2-((6aR,12aS)-1-fluoro-6a,7,12,12a-tetrahydro-7,7-dimethyl-6H-chromeno[4,3-b]quinolin-9-yl)oxazole-(4-(1,1-dione-1,4-thiazaperhydroin-yl)methanone); | 6.1 |
| 144. | 1-((6aR,12aS)-6a,7,12,12a-tetrahydro-1-fluoro-7,7-dimethyl-6H-chromeno[4,3-b]quinolin-9-yl)-5-methyl-1H-pyrazole-4-((4-ethanesulfonylpiperazin-1-yl)methanone); | 2.1 |
| 145. | 1-((6aR,12aS)-6a,7,12,12a-tetrahydro-1-fluoro-7,7-dimethyl-6H-chromeno[4,3-b]quinolin-9-yl)1-5-methyl-1H-pyrazole-4-((1,1-dione-1,4-thiazaperhydroin-yl)methanone); | 4.5 |
| 146. | 2-((6aR,12aS)-6a,7,12,12a-tetrahydro-4-methoxy-7,7-dimethyl-6H-chromeno[4,3-b]quinolin-9-yl)oxazole-4-carboxylic acid; | 8.2 |
| 147. | 2-((6aR,12aS)-1-methoxy-6a,7,12,12a-tetrahydro-7,7-dimethyl-6H-chromeno[4,3-b]quinolin-9-yl)oxazole-(4-(4-ethanesulfonylpiperazin-1-yl)methanone); | 7 |
| 148. | 2-((6aR,12aS)-1-methoxy-6a,7,12,12a-tetrahydro-7,7-dimethyl-6H-chromeno[4,3-b]quinolin-9-yl)oxazole-(4-(1,1-dione-1,4-thiazaperhydroin-yl)methanone); | 11 |

TABLE 1-continued

ABCA1 Induction Fold Increase over DMSO Vehicle at 10 μM

| NUMBER | NAME | FOLD INCREASE |
|---|---|---|
| 149. | (6aR,12aS)-2-bromo-6a,7,12,12a-tetrahydro-4-methoxy-7,7-dimethyl-9-(oxazol-5-yl)-6H-chromeno[4,3-b]quinoline; | 5.5 |
| 150. | (6aS,12aS)-2-bromo-6a,7,12,12a-tetrahydro-4-methoxy-7,7-dimethyl-9-(oxazol-5-yl)-6H-chromeno[4,3-b]quinoline; | 12.5 |
| 151. | (6aR,12aS)-methyl 2-bromo-6a,7,12,12a-tetrahydro-4-methoxy-7,7-dimethyl-6H-chromeno[4,3-b]quinoline-9-carboxylate; | 6.3 |
| 152. | (6aS,12aS)-methyl 2-bromo-6a,7,12,12a-tetrahydro-4-methoxy-7,7-dimethyl-6H-chromeno[4,3-b]quinoline-9-carboxylate; | 6.1 |
| 153. | (6aR,12aS)-methyl 6a,7,12,12a-tetrahydro-1-methoxy-7,7,12-trimethyl-6H-chromeno[4,3-b]quinoline-9-carboxylate; | 7.4 |
| 154. | 2-((6aR,12aS)-6a,7-dihydro-1-methoxy-7,7-dimethyl-6H-chromeno[4,3-b]quinolin-12(12aH)-yl)acetic acid; | 9.4 |
| 155. | (6aR,12aS)-6a,7,12,12a-tetrahydro-12-isopropyl-1-methoxy-7,7-dimethyl-6H-chromeno[4,3-b]quinoline; | 2.7 |
| 156. | 2-((6aS,12aS)-6a,7-dihydro-1-methoxy-7,7-dimethyl-6H-chromeno[4,3-b]quinolin-12(12aH)-yl)acetic acid; | 7.6 |
| 157. | ethyl 2-((6aR,12aS)-6a,7-dihydro-1-methoxy-7,7-dimethyl-6H-chromeno[4,3-b]quinolin-12(12aH)-yl)acetate; | 3.3 |
| 158. | (6aR,12aS)-12-benzyl-6a,7,12,12a-tetrahydro-1,9-dimethoxy-7,7-dimethyl-6H-chromeno[4,3-b]quinoline; | 9.2 |
| 159. | (6aR,12aS)-6a,7,12,12a-tetrahydro-4-methoxy-7,7-dimethyl-9-(oxazol-5-yl)-2-(1H-pyrazol-4-yl)-6H-chromeno[4,3-b]quinoline; | 7.6 |
| 160. | (6aS,12aS)-6a,7,12,12a-tetrahydro-4-methoxy-7,7-dimethyl-9-(oxazol-5-yl)-2-(1H-pyrazol-4-yl)-6H-chromeno[4,3-b]quinoline; | 4.7 |
| 161. | (6aR,12aS)-methyl 6a,7,12,12a-tetrahydro-4-methoxy-7,7-dimethyl-2-(1H-pyrazol-4-yl)-6H-chromeno[4,3-b]quinoline-9-carboxylate; | 8.1 |
| 162. | (6aR,12aS)-methyl 6a,7,12,12a-tetrahydro-4-methoxy-7,7-dimethyl-2-(3,5-dimethylisoxazol-4-yl)-6H-chromeno[4,3-b]quinoline-9-carboxylate; and | 7.7 |
| 163. | (6aS,12aS)-12-ethyl-6a,7,12,12a-tetrahydro-1-methoxy-7,7-dimethyl-6H-chromeno[4,3-b]quinoline; | 3.1 |
| 164. | (6aR,12aS)-2-bromo-6a,7,12,12a-tetrahydro-4-methoxy-7,7-dimethyl-9-(1H-tetrazol-5-yl)-6H-chromeno[4,3-b]quinoline; | 5.6 |
| 165. | (6aR,12aS)-6a,7,12,12a-tetrahydro-4-methoxy-7,7-dimethyl-2-(3,5-dimethylisoxazol-4-yl)-9-(oxazol-5-yl)-6H-chromeno[4,3-b]quinoline. | 7.4 |
| 166. | (6aR,12aS)-12-cyclohexyl-6a,7,12,12a-tetrahydro-1-methoxy-7,7-dimethyl-6H-chromeno[4,3-b]quinoline; and | 12.5 |
| 167. | (6aS,12aS)-12-cyclohexyl-6a,7,12,12a-tetrahydro-1-methoxy-7,7-dimethyl-6H-chromeno[4,3-b]quinoline. | 7.9 |
| 168. | diethyl ((6aR,12aS)-2-bromo-6a,7,12,12a-tetrahydro-4-methoxy-7,7-dimethyl-6H-chromeno[4,3-b]quinolin-9-yl)methylphosphonate; | 4 |
| 169. | (6aS,12aS)-2-bromo-6a,7,12,12a-tetrahydro-4-methoxy-7,7-dimethyl-9-(1H-tetrazol-5-yl)-6H-chromeno[4,3-b]quinoline; | 9.7 |
| 170. | methyl 3-((6aS,12aR)-6a,7-dihydro-1-methoxy-7,7-dimethyl-6H-chromeno[4,3-b]quinolin-12(12aH)-yl)propanoate; | 2.3 |
| 171. | methyl 3-((6aR,12aR)-6a,7-dihydro-1-methoxy-7,7-dimethyl-6H-chromeno[4,3-b]quinolin-12(12aH)-yl)propanoate; | 2.2 |
| 172. | (6aR,12aS)-12-propyl-6a,7,12,12a-tetrahydro-1-methoxy-7,7-dimethyl-6H-chromeno[4,3-b]quinoline; | 1.7 |
| 173. | (6aS,12aS)-12-propyl-6a,7,12,12a-tetrahydro-1-methoxy-7,7-dimethyl-6H-chromeno[4,3-b]quinoline; | 1.8 |
| 174. | (6aR,12aS)-12-butyl-6a,7,12,12a-tetrahydro-1-methoxy-7,7-dimethyl-6H-chromeno[4,3-b]quinoline; | 1.9 |
| 175. | (6aS,12aS)-12-butyl-6a,7,12,12a-tetrahydro-1-methoxy-7,7-dimethyl-6H-chromeno[4,3-b]quinoline; | 1.5 |
| 176. | (6aS,12aS)-6a,7,12,12a-tetrahydro-1,9-dimethoxy-7,7,12-trimethyl-6H-chromeno[4,3-b]quinoline; | 2.9 |
| 177. | 1-((6aS,12aS)-6a,7,12,12a-tetrahydro-2-iodo-4-methoxy-7,7-dimethyl-6H-chromeno[4,3-b]quinolin-9-yl)-5-methyl-1H-pyrazole-4-carboxylic acid; | 2.6 |
| 178. | 1-((6aR,12aS)-6a,7,12,12a-tetrahydro-2-iodo-4-methoxy-7,7-dimethyl-6H-chromeno[4,3-b]quinolin-9-yl)-5-methyl-1H-pyrazole-4-carboxylic acid. | 5.1 |
| 179. | diethyl ((6aS,12aS)-2-bromo-6a,7,12,12a-tetrahydro-4-methoxy-7,7-dimethyl-6H-chromeno[4,3-b]quinolin-9-yl)methylphosphonate; | 5.2 |
| 180. | diethyl (6a,7,12,12a-tetrahydro-1-methoxy-7,7-dimethyl-6H-chromeno[4,3-b]quinolin-9-yl)methylphosphonate; | 2.2 |
| 181. | diethyl ((6aR,12aS)-6a,7,12,12a-tetrahydro-4-methoxy-7,7-dimethyl-2-(1H-pyrazol-4-yl)-6H-chromeno[4,3-b]quinolin-9-yl)methylphosphonate; | 4.9 |
| 182. | (6aR,12aS)-6a,7,12,12a-tetrahydro-4-methoxy-7,7-dimethyl-2-(1H-pyrazol-4-yl)-6H-chromeno[4,3-b]quinoline-9-carbonitrile. | 4.6 |

EXAMPLE 17

In Vivo Mouse Model

To confirm the in vitro activity of compounds that induce ABCA1 gene expression in vitro and to further profile for acceptable bioavailability, PK and lipogenic activity, compounds were initially screened in a single dose 5 h mouse model. Compounds were prepared as suspensions in 0.75% carboxymethylcellulose/0.1% Tween 80 and administered by gavage to male mice at a dose of 1-200 mpk along with a vehicle control group. Food was removed immediately prior to dosing and the mice were bled retro-orbitally at 1 h to measure approximate peak plasma drug levels and at necropsy (5 h), by cardiac puncture, to measure 5 h drug levels.

EDTA plasma was separated from the blood samples by centrifugation and used for measurement of plasma drug levels by LC-MS. Primary blood mononuclear cells (PBMC's) were freshly isolated from the packed blood cells by differential centrifugation. A liver sample was preserved in RNALater (Qiagen) and the whole intestine was rinsed in saline and snap-frozen in liquid $N_2$. RNA was isolated from the liver, intestine and PBMC's from individual mice using a Tissuelyzer (Qiagen) and RNAeasy RNA purification kits (Qiagen) with DNAse treatment (Qiagen).

cDNA was prepared from each RNA sample and used to determine the expression levels of mouse mABCA1, mSREBP1c, mFASN (fatty acid synthase) and mCYc (cyclophilin A). All 4 genes were measured at the same time using a quadraplexed Taqman qPCR assay using custom gene-specific primer-probe sets. Data was normalized to mCYC and gene expression was expressed relative to the vehicle treated group (fold). Compounds that induced ABCA1 and achieved acceptable plasma concentrations at both 1 h and 5 h were analyzed in this model at additional concentrations to obtain dose response information.

The compounds of the invention induced expression of ABCA1 in this assay.

EXAMPLE 18

Cholesterol Efflux

The ability of the compounds of the invention to stimulate cholesterol efflux from cells is determined in the following assay.

RAW 264.7 cells are loaded with cholesterol as described in Smith et al., *J. Biol. Chem.*, 271:30647-30655 (1996). Briefly, semi-confluent cells plated in 48-well dishes are incubated in 0.2 ml of DMEM supplemented with 4.5 g/L glucose, 0.1 g/L sodium pyruvate and 0.584 g/L of glutamine, 10% fetal bovine serum, 50 µg/ml acetylated low density lipoprotein (AcLDL) and 0.5 µCi/ml of [$^3$H]-cholesterol. After 18 hr, cells are washed two times with PBS containing 1% BSA and incubated overnight (16-18 hours) in DMEM/1% BSA to allow for equilibration of cholesterol pools. The cells are then rinsed four times with PBS/BSA and incubated for one hour at 37° C. with DMEM/BSA. Efflux medium (DMEM/BSA) containing either albumin alone (control), albumin plus HDL (40 µg protein/ml), or albumin plus apo A-I (20 µg/ml, Biodesign International, Kennebunk, Me.) is added and the cells are incubated for 4, 24, or 48 hours.

Cholesterol efflux is measured by removing the medium, washing the cell layer and extracting the cells. Cellular radioactivity is measured by scintillation counting after solubilization in 0.5 ml of 0.2M NaOH (Smith et al., *J. Biol. Chem.*, 271:30647-30655 (1996) or extraction in hexane:isopropanol (3:2 v/v) as described in Francis et al., *J. Clin. Invest.*, 96, 78-87 (1995). The labelled phospholipid remaining in the medium is also determined by liquid scintillation counting. The efflux of cholesterol is expressed as the percentage of tritiated lipid counts in the medium over the total tritiated lipid counts recovered from the cells and medium (cpm medium/cpm (medium+lysate)×100).

Cholesterol efflux is also determined in THP-1 cells. Replicate cultures of THP-1 cells are plated in 48 well dishes using the method described (see Kritharides et al Thrombo Vasc Biol 18, 1589-1599, 1998). Cells are plated at an initial density of 500,000 cells/well. After addition of PMA (100 ng/ml), the cultures are incubated for 48 hr at 37 C. The medium is aspirated and replaced with RPMI-1640 medium containing 2 mg/ml of FAFA, 50 µg/ml of acetylated LDL and 3 µCi/ml of radiolabeled cholesterol. After an overnight incubation, the medium is aspirated, the wells washed extensively with PBS. 0.2 ml of RPMI-1640 medium containing 2 mg/ml of FAFA is added to each well. The compound of interest are added to a final concentration of 10 µM. After 4 hr, Apolipoprotein A1 (10 µg/ml) is added to some wells and the cultures incubated for 24 hr. The medium is harvested and assayed for radioactivity. The amount of radioactivity in the cell layer is ascertained by adding 0.2 ml of 2 M NaOH and counting the lysed cells. The percent cholesterol efflux is calculated as described above.

EXAMPLE 19

The relationship between ABCA1 expression and HDL levels are determined in the following in vivo assay.

Candidate compounds that increase ABCA1 expression in vitro and are pharmacologically active and available in vivo are administered daily at a predetermined dosage to 7-12 week old male C57B1/6 mice by gavage in 0.75% carboxymethylcellulose/0.1% Tween 80 or other pharmaceutically acceptable formulation and route of administration. Five hours after the final injection, fasted EDTA-plasma and appropriate tissues are collected for analysis. Plasma lipoproteins levels and HDL cholesterol are measured by FPLC using a Superose 6/30 column and online detection of the cholesterol in the eluate. In vivo changes in the expression of ABCA1, SREBP1c, FASN and other relevant genes are further confirmed by qPCR of the cDNA's prepared from tissue RNA.

The in vivo efficacy of candidate compounds to induce lipogenesis and increased triacylglycerol production and storage is evaluated by measuring hepatic SREBP1c gene expression by qPCR and plasma and tissue triacylglycerol concentrations.

A correlation between ABCA1 expression and HDL levels was observed in this assay.

We claim:

1. A compound having the structure of Formula I:

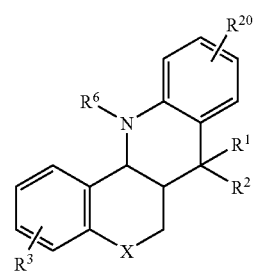

Formula I wherein:

R¹ and R² are independently optionally substituted lower alkyl, optionally substituted aryl, optionally substituted alkenyl, optionally substituted heteroaryl, or optionally substituted heterocyclyl; or R¹ and R² when taken together with the carbon atom to which they are attached represent a 5 or 6 membered carbocyclic or heterocyclic ring;

$R^3$ is hydrogen, hydroxyl, optionally substituted lower alkyl, optionally substituted alkenyl, optionally substituted alkynyl, optionally substituted lower alkoxy, optionally substituted aryl, optionally substituted heteroaryl, optionally substituted heterocyclyl, cyano, halo, —$SO_2$—$NR^9R^{10}$, or —$C(O)R^{11}$, in which $R^9$ and $R^{10}$ are independently hydrogen, optionally substituted lower alkyl, optionally substituted aryl, optionally substituted heteroaryl, optionally substituted heterocyclyl, or may joint to form a 5 or 6 membered optionally substituted heterocyclic ring, and $R^{11}$ is —OH or optionally substituted lower alkoxy;

$R^6$ is hydrogen, optionally substituted lower alkyl, optionally substituted cycloalkyl, $C(O)R^{12}$, or —$S(O)_2R^{13}$, in which $R^{12}$ is optionally substituted lower alkyl, lower alkoxy or —$NR^{14}R^{15}$, in which $R^{13}$, $R^{14}$, and $R^{15}$ are independently hydrogen, optionally substituted lower alkyl, optionally substituted aryl, optionally substituted heteroaryl, or optionally substituted heterocyclyl, or $R^{14}$ and $R^{15}$ may join to form a 5 or 6 membered optionally substituted heterocyclic ring;

$R^{20}$ is optionally substituted aryl, optionally substituted heteroaryl, optionally substituted heterocyclyl, —$SR^{14}$, —$C(S)R^{14}$, —$C(S)NR^{14}R^{15}$, —$S(O)_2R^{13}$, or —$S(O)_2NR^9R^{10}$; and X is oxygen, sulfur, —$S(O)$—, —$S(O)_2$— or —$NR^{16}$—, in which $R^{16}$ is hydrogen, optionally substituted lower alkyl, optionally substituted aryl, —$C(O)R^{12}$, or —$S(O)_2R^{13}$.

2. The compound of claim 1, wherein X is oxygen.

3. The compound of claim 2, wherein R¹ and R² are both independently optionally substituted lower alkyl.

4. The compound of claim 3, wherein $R^6$ is hydrogen.

5. The compound of claim 4, wherein $R^{20}$ is optionally substituted heteroaryl.

6. The compound of claim 5, selected from the group consisting of:

4-methoxy-7,7-dimethyl-9-(1,2,3,4-tetraazol-5-yl)-7,12,12a,6a-tetrahydrochromano[4,3-b]quinoline;

10-(1H-1,2,3,4-tetraazol-5-yl)(12aS,6aR)-1-methoxy-7,7-dimethyl-7,12,12a,6a-tetrahydrochromano[4,3-b]quinoline;

(12aS,6aR)-1-methoxy-7,7-dimethyl-9-(1,3-oxazol-5-yl)-7,12,12a,6a-tetrahydrochromano[4,3-b]quinoline;

(12aS,6aR)-1-methoxy-7,7-dimethyl-9-(1,2,3,4-tetraazol-5-yl)-7,12,12a,6a-tetrahydrochromano[4,3-b]quinoline;

(12aS,6aR)-1-methoxy-7,7-dimethyl-9-(1,2,3-thiadiazol-4-yl)-7,12,12a,6a-tetrahydrochromano[4,3-b]quinoline;

1-methoxy-7,7-dimethyl-9-(4-methyl(1,2,4-triazol-3-yl))-7,12,12a,6a-tetrahydrochromano[4,3-b]quinoline;

ethyl 1-((6aR,12aS)-6a,7,12,12a-tetrahydro-1-methoxy-7,7-dimethyl-6H-chromeno[4,3-b]quinolin-9-yl)-5-methyl-1H-pyrazole-4-carboxylate;

1-((6aR,12aS)-6a,7,12,12a-tetrahydro-1-methoxy-7,7-dimethyl-6H-chromeno[4,3-b]quinolin-9-yl)-5-methyl-1H-pyrazole-4-carboxylic acid;

2-((6aR,12aS)-1-fluoro-6a,7,12,12a-tetrahydro-7,7-dimethyl-6H-chromeno[4,3-b]quinolin-9-yl)oxazole-4-carboxylic acid;

ethyl 1-((6aR,12aS)-6a,7,12,12a-tetrahydro-1-methoxy-7,7-dimethyl-6H-chromeno[4,3-b]quinolin-9-yl)-1H-pyrazole-4-carboxylate;

1-((6aR,12aS)-6a,7,12,12a-tetrahydro-1-methoxy-7,7-dimethyl-6H-chromeno[4,3-b]quinolin-9-yl)-1H-pyrazole-4-carboxylic acid;

1-((6aR,12aS)-6a,7,12,12a-tetrahydro-1-methoxy-7,7-dimethyl-6H-chromeno[4,3-b]quinolin-9-yl)-N,N-dimethyl-1H-pyrazole-4-carboxamide;

1-((6aR,12aS)-6a,7,12,12a-tetrahydro-1-methoxy-7,7-dimethyl-6H-chromeno[4,3-b]quinolin-9-yl)1-1H-pyrazole-4-((1,1-dione-1,4-thiazaperhydroin-yl)methanone);

1-((6aR,12aS)-6a,7,12,12a-tetrahydro-1-methoxy-7,7-dimethyl-6H-chromeno[4,3-b]quinolin-9-yl)-5-methyl-1H-pyrazole-4-((4-ethanesulfonylpiperazin-1-yl)methanone);

1-((6aR,12aS)-6a,7,12,12a-tetrahydro-1-methoxy-7,7-dimethyl-6H-chromeno[4,3-b]quinolin-9-yl)1-5-methyl-1H-pyrazole-4-((1,1-dione-1,4-thiazaperhydroin-yl)methanone);

2-((6aR,12aS)-1-fluoro-6a,7,12,12a-tetrahydro-7,7-dimethyl-6H-chromeno[4,3-b]quinolin-9-yl)oxazole-(4-(4-ethanesulfonylpiperazin-1-yl)methanone);

2-((6aR,12aS)-1-fluoro-6a,7,12,12a-tetrahydro-7,7-dimethyl-6H-chromeno[4,3-b]quinolin-9-yl)oxazole-(4-(1,1-dione-1,4-thiazaperhydroin-yl)methanone);

1-((6aR,12aS)-6a,7,12,12a-tetrahydro-1-fluoro-7,7-dimethyl-6H-chromeno[4,3-b]quinolin-9-yl)-5-methyl-1H-pyrazole-4-((4-ethanesulfonylpiperazin-1-yl)methanone);

1-((6aR,12aS)-6a,7,12,12a-tetrahydro-1-fluoro-7,7-dimethyl-6H-chromeno[4,3-b]quinolin-9-yl)1-5-methyl-1H-pyrazole-4-((1,1-dione-1,4-thiazaperhydroin-yl)methanone);

2-((6aR,12aS)-6a,7,12,12a-tetrahydro-4-methoxy-7,7-dimethyl-6H-chromeno[4,3-b]quinolin-9-yl)oxazole-4-carboxylic acid;

2-((6aR,12aS)-1-methoxy-6a,7,12,12a-tetrahydro-7,7-dimethyl-6H-chromeno[4,3-b]quinolin-9-yl)oxazole-(4-(4-ethanesulfonylpiperazin-1-yl)methanone); and 2-((6aR,12aS)-1-methoxy-6a,7,12,12a-tetrahydro-7,7-dimethyl-6H-chromeno[4,3-b]quinolin-9-yl)oxazole-(4-(1,1-dione-1,4-thiazaperhydroin-yl)methanone).

7. The compound of claim 4, wherein $R^{20}$ is optionally substituted heterocycle.

8. The compound of claim 7, selected from the group consisting of:

4-((6aS,12aR)-4-methoxy-7,7-dimethyl-7,12,12a,6a-tetrahydrochromano[4,3-b]quinolin-9-yl)-1,4-thiazaperhydroine-1,1-dione;

4-(4-methoxy-7,7-dimethyl-7,12,12a,6a-tetrahydrochromano[4,3-b]quinolin-9-yl)-1,4-thiazaperhydroine-1,1-dione; and 4-((12aS,6aR)-1-methoxy-7,7-dimethyl-7,12,12a,6a-tetrahydrochromano[4,3-b]quinolin-9-yl)-1,4-thiazaperhydroine-1,1-dione.

9. The compound of claim 4, wherein $R^{20}$ is aryl.

10. The compound of claim 9, namely 9-(3-(2H-1,2,3,4-tetraazol-5-yl)phenyl)(12aS,6aR)-1-methoxy-7,7-dimethyl-7,12,12a,6a-tetrahydrochromano[4,3-b]quinoline.

11. The compound of claim 4, wherein $R^{20}$ is —$SR^{14}$, —$S(O)_2R^{13}$, —$C(S)R^{14}$, or —$C(S)NR^{14}R^{15}$.

12. The compound of claim 11, selected from the group consisting of:
- amino(4-methoxy-7,7-dimethyl(7,12,12a,6a-tetrahydro-chromano[4,3-b]quinolin-9-yl))methane-1-thione;
- (12aS,6aR)-1-methoxy-7,7-dimethyl-9-methylthio-7,12,12a,6a-tetrahydrochromano[4,3-b]quinoline;
- (6aR,12aS)-6a,7,12,12a-tetrahydro-1-methoxy-7,7-dimethyl-9-(methylsulfonyl)-6H-chromeno[4,3-b]quinoline; and;
- (6aR,12aS)-9-(4-fluorophenylsulfonyl)-6a,7,12,12a-tetrahydro-1-methoxy-7,7-dimethyl-6H-chromeno[4,3-b]quinoline; and
- 2-((6aR,12aS)-6a,7,12,12a-tetrahydro-1-methoxy-7,7-dimethyl-6H-chromeno[4,3-b]quinolin-9-ylsulfonyl)acetic acid.

13. The compound of claim 1, wherein the 12a,6a ring juncture is cis.

14. The compound of claim 1, wherein the 12a,6a ring juncture is trans.

15. The compound of claim 1, wherein the 12a,6a ring juncture provides a single enantiomer.

16. A method of treating a disease state or condition in a mammal that is alleviable by treatment with an agent capable of increasing ABCA-1 expression, wherein the disease state or condition is coronary artery disease, atherosclerosis, or dyslipidemia, the method comprising administering to a mammal in need thereof a therapeutically effective dose of a compound of claim 1.

17. The method of claim 16, wherein the disease state or condition is coronary artery disease or atherosclerosis.

18. A method for elevating serum levels of HDL cholesterol in a mammal, comprising administering to a mammal in need thereof a therapeutically effective dose of a compound of claim 1.

19. A method for promoting cholesterol efflux from cells in a mammal, comprising administering to a mammal in need thereof a therapeutically effective dose of a compound of claim 1.

20. A pharmaceutical composition comprising at least one pharmaceutically acceptable excipient and a therapeutically effective amount of a compound of claim 1.

* * * * *